US010577332B2

(12) United States Patent
Hoener et al.

(10) Patent No.: US 10,577,332 B2
(45) Date of Patent: Mar. 3, 2020

(54) TETRAZOLE DERIVATIVES

(71) Applicant: Hoffmann-La Roche Inc., Little Falls, NJ (US)

(72) Inventors: Marius Hoener, Basel (CH); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/569,349

(22) PCT Filed: Apr. 19, 2016

(86) PCT No.: PCT/EP2016/058594
§ 371 (c)(1),
(2) Date: Oct. 25, 2017

(87) PCT Pub. No.: WO2016/169902
PCT Pub. Date: Oct. 27, 2016

(65) Prior Publication Data
US 2018/0297961 A1    Oct. 18, 2018

(30) Foreign Application Priority Data
Apr. 23, 2015 (EP) .................... 15164885

(51) Int. Cl.
*C07D 409/12* (2006.01)
*A61K 31/41* (2006.01)
*C07D 257/04* (2006.01)
*C07D 257/06* (2006.01)

(52) U.S. Cl.
CPC ......... *C07D 257/04* (2013.01); *C07D 257/06* (2013.01); *C07D 409/12* (2013.01)

(58) Field of Classification Search
None
See application file for complete search history.

(56) References Cited

U.S. PATENT DOCUMENTS

| 5,882,926 | A | 3/1999 | Amara et al. |
| 10,005,736 | B1 | 6/2018 | Hoener et al. |
| 10,029,989 | B2 | 7/2018 | Hoener et al. |
| 10,092,546 | B2 | 10/2018 | Hoener et al. |
| 10,273,217 | B2 | 4/2019 | Hoener et al. |
| 10,457,644 | B2 | 10/2019 | Hoener et al. |
| 10,457,663 | B2 | 10/2019 | Hoener et al. |
| 2009/0163499 | A1 | 6/2009 | Chen et al. |
| 2015/0191487 | A1* | 7/2015 | Dillon ............ C07D 257/04 544/58.2 |

FOREIGN PATENT DOCUMENTS

| JP | 2006-151954 A | 6/2006 |
| JP | 2010-540585 A | 12/2010 |
| JP | 2011-528658 A | 11/2011 |
| WO | 2007/042545 A1 | 4/2007 |
| WO | 2008/000645 A1 | 1/2008 |
| WO | 2009/043780 A1 | 4/2009 |
| WO | 2009/077365 A1 | 6/2009 |
| WO | 2009/077366 A1 | 6/2009 |
| WO | 2009/077367 A1 | 6/2009 |
| WO | 2010/009062 A1 | 1/2010 |
| WO | 2010/033168 A2 | 3/2010 |
| WO | 2010/051188 A1 | 5/2010 |

(Continued)

OTHER PUBLICATIONS

ISR of PCT/EP2016/058594 (dated Jun. 24, 2016).
Aoyama et al., "Neuronal glutathione deficiency and age-dependent neurodegeneration in the EAAC1 deficient mouse." Nat Neurosci. 9(1):119-126 (2006).
Bridges Richard J. et al., "The excitatory amino acid transporters: pharmacological insights on substrate and inhibitor specificity of the EAAT subtypes" Pharmacology & Therapeutics 107(3):271-285 (Sep. 1, 2005).
Greenfield Alexander et al., "Synthesis and biological activities of aryl-ether-, biaryl-, and fluorene-aspartic acid and diaminopropionic acid analogs as potent inhibitors of the high-affinity glutamate transporter EAAT-2" Bioorganic & Medicinal Chemistry Letters 15(22):4985-4988 (Nov. 14, 2005).

(Continued)

*Primary Examiner* — Alicia L Otton
(74) *Attorney, Agent, or Firm* — Mark D. Kafka

(57) ABSTRACT

The present invention relates to compounds of formula I

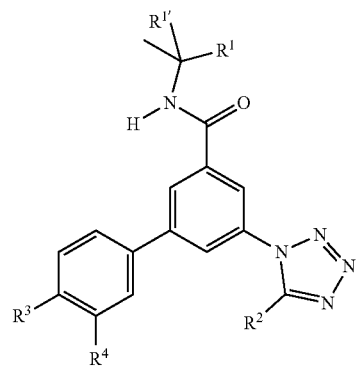

wherein
$R^{1'}$ is $CH_3$
$R^1$ is methyl, ethyl, $CF_3$, $CH_2OH$, cyclopropyl or cyano, or $R^{1'}$ and $R^1$ may form together a 1,1-dioxo-tetrahydro-thiophen-3-yl ring;
$R^2$ is hydrogen, methyl, ethyl, isopropyl, tertbutyl, cyclopropyl or $CF_3$;
$R^3$ is Cl, F, $CF_3$, methyl, methoxy, isopropyl or cyclopropyl;
$R^4$ is hydrogen, methyl, F or Cl;
or to a pharmaceutically acceptable salt or acid addition salt, to a racemic mixture, or to its corresponding enantiomer and/or optical isomer and/or stereoisomer thereof for use in the treatment of schizophrenia, bipolar disorder, obsessive-compulsive disorder or autism spectrum disorder.

4 Claims, No Drawings

(56) References Cited

FOREIGN PATENT DOCUMENTS

| WO | 2016/169902 A1 | 10/2016 |
| WO | 2016/193235 A1 | 12/2016 |
| WO | 2017/009274 | 1/2017 |
| WO | 2017/072083 A1 | 5/2017 |

OTHER PUBLICATIONS

International Preliminary Report on Patentability (IPRP) for PCT/EP2017/075875 dated Apr. 16, 2019.
International Search Report for PCT/EP2017/075875 dated Dec. 12, 2017.
ISR of PCT/EP2016/062204 (Completed on Jul. 27, 2016).
ISR of PCT/EP2016/073589 (Completed Nov. 7, 2016).
ISR of PCT/EP2016/075590 (Completed on Jan. 19, 2017).
ISR of PCT/EP2017/051873 (Completed on Feb. 27, 2017).
ISR of PCT/EP2017/062512 (Completed on Jul. 11, 2017).
Jarzylo et al., "Parasynaptic NMDA Receptor Signaling Couples Neuronal Glutamate Transporter Function to AMPA Receptor Synaptic Distribution and Stability" The Journal of Neuroscience 32(7):2552-2563 (2012).
Jensen et al., "Excitatory amino acid transporters: recent insights into molecular mechanisms, novel modes of modulation and new therapeutic possibilities" Current Opinion in Pharmacology 20:116-123 (Feb. 1, 2015).
Jing et al. et al., "GFRα-2 and GFRα-3 Are Two New Receptors for Ligands of the GDNF Family" J Biol Chem 272(52):33111-33117 (Dec. 26, 1997).
Mavencamp Terri L. et al., "Synthesis and preliminary pharmacological evaluation of novel derivatives of L-β-threo-benzylaspartate as inhibitors of the neuronal glutamate transporter EAAT3" Bioorganic & Medicinal Chemistry 16(16):7740-7748 (Aug. 15, 2008).
Nieoullon et al., "The neuronal exeitatory amino acid transporter EAAC1/EAAT3: does it represent a major actor at the brain exeitatory synapse?" Journal of Neurochemistry 98: 1007-1018 (2006).
Product Sheets R&D Systems, Human FGF R3 (IIIb) Antibody, Monoclonal Mouse IgG$_1$ Clone #133111, MAB765 (downloaded Aug. 31, 2011).
Scimemi et al., "Neuronal Transporters Regulate Glutamate Clearance, NMDA Receptor Activation, and Synaptic Plasticity in the Hippocampus" The Journal of Neuroscience 29(46):14581-14595 (2009).
Wendland et al., "A Haplotype Containing Quantitative Trait Loci for SLC1A1 Gene Expression and Its Association With Obsessive-Compulsive Disorder" Arch Gen Psychiatry 66(4):408-416 (2009).

* cited by examiner

TETRAZOLE DERIVATIVES

CROSS REFERENCE TO RELATED APPLICATIONS

This application is a 371 national phase application of International Patent Application No. PCT/EP2016/058594, filed Apr. 19, 2016, and claims priority to European Patent Application No. 15164885.4, filed on Apr. 23, 2015, the entire contents of each of which are incorporated herein by reference.

The present invention relates to compounds of formula I

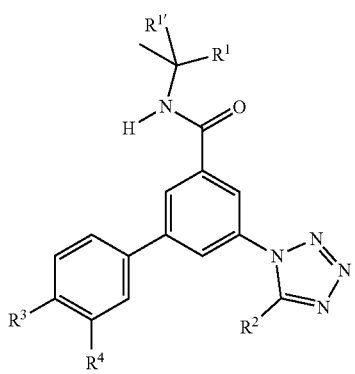

wherein
$R^{1'}$ is $CH_3$
$R^1$ is methyl, ethyl, $CF_3$, $CH_2OH$, cyclopropyl or cyano, or $R^{1'}$ and $R^1$ may form together a 1,1-dioxo-tetrahydro-thiophen-3-yl ring;
$R^2$ is hydrogen, methyl, ethyl, isopropyl, tertbutyl, cyclopropyl or $CF_3$;
$R^3$ is Cl, F, $CF_3$, methyl, methoxy, isopropyl or cyclopropyl;
$R^4$ is hydrogen, methyl, F or Cl;
or to a pharmaceutically acceptable salt or acid addition salt, to a racemic mixture, or to its corresponding enantiomer and/or optical isomer and/or stereoisomer thereof for use in the treatment of psychiatric disorders such as schizophrenia, bipolar disorder, obsessive-compulsive disorder or autism spectrum disorder.

It has been surprisingly been found that the compounds of general formula I are EAAT3 inhibitors.

The excitatory amino acid transporter 3 (EAAT3), also referred to in human studies as solute carrier family 1, member 1 (systematic gene name: SLC1A1) and in rodents as excitatory amino acid carrier 1 (EAAC1), is a high-affinity anionic amino acid transporter found in neurons throughout the cortex and in the hippocampus, basal ganglia (striatum, thalamus), and the olfactory bulb. EAAT3 functions to buffer local glutamate concentrations at excitatory synapses, for example in the hippocampus, and modulates the differential recruitment of glutamate receptor subtypes at extrasynaptic sites. Furthermore, EAAT3 is thought to be involved in facilitating GABA and glutathione biosynthesis. EAAT3 is a member of the EAAT family that mediates the uptake of glutamate into neuronal and glial cells of the mammalian CNS. Two transporters expressed primarily in glia, EAAT1 and EAAT2, are crucial for glutamate homeostasis in the adult mammalian brain and for rapid clearance of glutamate from the synaptic cleft. Three neuronal transporters (EAAT3, EAAT4, and EAAT5) appear to have additional functions in regulating and processing cellular excitability with EAAT3 being abundantly expressed throughout the CNS (EAAT4 is unique to Purkinje cells of the cerebellum and EAAT5 is expressed in rod photoreceptor and bipolar cells of the retina).

EAATs are assembled as trimers, and the existence of multiple isoforms raises the question of whether certain isoforms can form hetero-oligomers. In the mammalian brain, the specificity of excitatory synaptic transmission depends on rapid diffusion of glutamate away from active synapses and the powerful uptake capacity of glutamate transporters in astrocytes. The extent to which neuronal glutamate transporters influence the lifetime of glutamate in the extracellular space remains unclear, but it is thought to be minor. EAAT3, the predominant neuronal glutamate transporter at excitatory synapses in hippocampal area CA1, buffers glutamate released during synaptic events and prolongs the time course of its clearance by astrocytes. EAAT3 does not significantly alter activation of receptors in the synaptic cleft. Instead, it reduces recruitment of perisynaptic/extrasynaptic NR2B-containing NMDARs, thereby facilitating induction of long-term potentiation by short bursts of high-frequency stimulation. Specific EAAT3 inhibitors may have the potential to locally and specifically strengthen particular synapses.

Obsessive-compulsive disorder (OCD) is among the most common mental disorders (prevalence 1-3%), and is at least as prevalent as schizophrenia and bipolar disorder. In the United States, one in 50 adults suffers from OCD. OCD affects children and adolescents as well as adults. Roughly one third to one half of adults with OCD reports a childhood onset of the disorder, and the disorder is typically chronic in nature. Treatment consists of predominantly serotonergic TCAs (clomipramine) or SSRIs in combination with cognitive-behavioral therapy (CBT). Overall, response to these interventions is of some but still limited benefit (approximately comparable to antidepressant response in MDD), and given the chronicity of OCD, the unmet medical need remains very high. OCD has been linked to serotonin and glutamate abnormalities. The hypothesis of glutamate signaling dysfunction in OCD is based on findings from neuroimaging, animal models, positional cloning and treatment studies.

The obsessive-compulsive symptomatology in OCD has considerable phenomenological, epidemiological and possibly (aetio)-pathophysiological overlap with a core autism spectrum disorder criterion: "restricted, repetitive patterns of behavior, interests, or activities" (taken from proposed DSM-5 revision). In support of this notion, human genetics studies have linked both the serotonin transporter and EAAT3 (SLC1A1) genes to autism spectrum disorder (ASD) or rigid-compulsive behavior in ASD and to OCD.

In addition, obsessive-compulsive symptoms induced by antipsychotics in schizophrenic bipolar disorder patients have been linked to EAAT3 (SLC1A1) gene variants. Post-mortem brain studies have shown that both classic and atypical antipsychotics reduce EAAT3, suggesting an involvement of this transporter in neuroleptic mechanisms beyond dopamine and serotonin modulation. Moreover, genetic variation in the human gene EAAT3 (SLC1A1) has been associated with antipsychotic drug response.

There is converging evidence from neurobiological data, human genetics, imaging studies and experimental treatments that EAAT3 is a key pathophysiological element in OCD and rigid-compulsive behavior in autism and in schizophrenia.

Curr. Opin. Pharmacol. 20, 116-123, 2015
J. Neurosci., 32, 2552-2563, 2012

J. Neurosci 29, 14581-14595, 2009
Arch. Gen. Psychiatry, 66, 408-416, 2009
Pharmacol. Ther. 107, 271-285, 2005
J. Neurochem. 98, 1007-1018, 2006
Nat. Neurosci., 9, 119-126, 2006

Compounds of formula I are distinguished by having valuable therapeutic properties. They can be used in the treatment or prevention of disorders, relating to EAAT3 inhibitors. The most preferred indications for compounds which are EAAT3 inhibitors are psychiatric disorders such as schizophrenia, bipolar disorder, obsessive-compulsive disorder or autism spectrum disorder.

The present invention relates to compounds of formula I and to their pharmaceutically acceptable salts for use in the treatment of psychiatric disorders such as schizophrenia, bipolar disorder, obsessive-compulsive disorder or autism spectrum disorder, to compounds of formula IA as pharmaceutically active substances, to the processes for their production as well as to their use in the treatment or prevention of disorders, relating to EAAT3 inhibitors, such as schizophrenia, bipolar disorder, obsessive-compulsive disorder or autism spectrum disorder and to pharmaceutical compositions containing the compounds of formula IA A further object of the present invention is a method for the treatment or prophylaxis of psychiatric disorder such as schizophrenia, bipolar disorder, obsessive-compulsive disorder or autism spectrum disorder, which method comprises administering an effective amount of a compound of formula I or IA to a mammal in need.

Furthermore, the invention includes all racemic mixtures, all their corresponding enantiomers and/or optical isomers, or analogues containing isotopes of hydrogen, fluorine, carbon, oxygen or nitrogen.

One object of the present invention are novel compounds of formula IA,

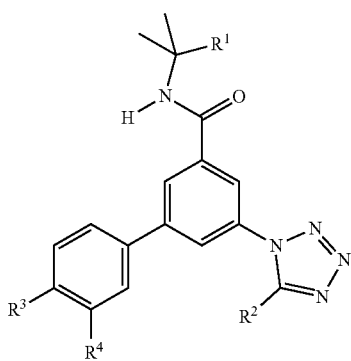

IA wherein
$R^1$ is methyl, ethyl, $CF_3$, $CH_2OH$, cyclopropyl or cyano;
$R^2$ is hydrogen, methyl, ethyl, isopropyl, tertbutyl, cyclopropyl or $CF_3$;
$R^3$ is Cl, F, $CF_3$, methyl, methoxy, isopropyl or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof.

One further object of the invention are compounds of formula IA-1,

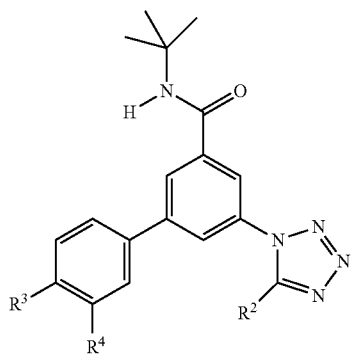

wherein
$R^2$ is hydrogen, methyl, ethyl, isopropyl, tertbutyl, cyclopropyl or $CF_3$;
$R^3$ is Cl, F, $CF_3$, methyl, methoxy, isopropyl or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compounds N-tert-Butyl-3-(tetrazol-1-yl)-5-[4-(trifluoromethyl)phenyl]-benzamide
N-tert-Butyl-3-(4-chlorophenyl)-5-(tetrazol-1-yl)-benzamide
N-tert-Butyl-3-(4-methylphenyl)-5-(5-methyltetrazol-1-yl)-benzamide
N-tert-Butyl-3-(5-cyclopropyltetrazol-1-yl)-5-(4-methylphenyl)-benzamide
N-tert-Butyl-3-(5-ethyltetrazol-1-yl)-5-(4-methylphenyl)-benzamide
N-tert-Butyl-3-(4-chlorophenyl)-5-(5-propan-2-yltetrazol-1-yl)-benzamide
N-tert-Butyl-3-(5-propan-2-yltetrazol-1-yl)-5-[4-(trifluoromethyl)-phenyl]-benzamide
N-tert-Butyl-3-(4-chlorophenyl)-5-(5-cyclopropyltetrazol-1-yl)-benzamide
N-tert-Butyl-3-(4-fluorophenyl)-5-(5-propan-2-yltetrazol-1-yl)-benzamide
N-tert-Butyl-3-(4-chlorophenyl)-5-(5-methyltetrazol-1-yl)-benzamide
N-tert-Butyl-3-(5-cyclopropyltetrazol-1-yl)-5-(4-fluorophenyl)-benzamide
N-tert-Butyl-3-(4-chlorophenyl)-5-[5-(trifluoromethyl)-tetrazol-1-yl]-benzamide
N-tert-Butyl-3-(4-fluorophenyl)-5-(5-methyltetrazol-1-yl)-benzamide
N-tert-Butyl-3-(5-tert-butyltetrazol-1-yl)-5-(4-chlorophenyl)-benzamide
N-tert-Butyl-3-(5-tert-butyltetrazol-1-yl)-5-(4-fluorophenyl)-benzamide
N-tert-Butyl-3-(5-tert-butyltetrazol-1-yl)-5-(4-methylphenyl)-benzamide
N-tert-Butyl-3-(5-tert-butyltetrazol-1-yl)-5-(4-fluoro-3-methylphenyl)-benzamide
N-tert-Butyl-3-(5-tert-butyltetrazol-1-yl)-5-[4-(trifluoromethyl)-phenyl]-benzamide
N-tert-Butyl-3-(5-tert-butyltetrazol-1-yl)-5-(4-chloro-3-fluorophenyl)-benzamide
N-tert-Butyl-3-(5-tert-butyltetrazol-1-yl)-5-(3,4-difluorophenyl)-benzamide
N-tert-Butyl-3-(5-tert-butyltetrazol-1-yl)-5-(4-cyclopropylphenyl)-benzamide or N-tert-Butyl-3-(5-tert-butyltetrazol-1-yl)-5-(3-fluoro-4-methylphenyl)-benzamide.

One further object of the present invention are compounds of formula IA-2

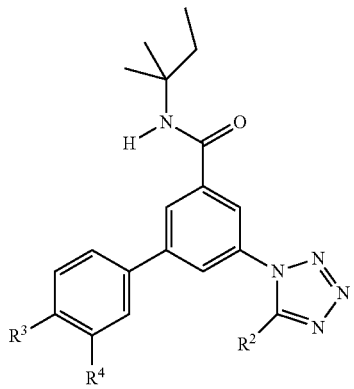

IA-2 wherein
$R^2$ is hydrogen, methyl, ethyl, isopropyl, tertbutyl, cyclopropyl or $CF_3$;
$R^3$ is Cl, F, $CF_3$, methyl, methoxy, isopropyl or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compounds 3-(4-Fluorophenyl)-N-(2-methylbutan-2-yl)-5-(tetrazol-1-yl)-benzamide
N-(2-Methylbutan-2-yl)-3-(tetrazol-1-yl)-5-[4-(trifluoromethyl)phenyl]-benzamide
3-(3-Fluoro-4-methylphenyl)-N-(2-methylbutan-2-yl)-5-(tetrazol-1-yl)-benzamide
3-(4-Fluoro-3-methylphenyl)-N-(2-methylbutan-2-yl)-5-(tetrazol-1-yl)-benzamide
3-(4-Methoxyphenyl)-N-(2-methylbutan-2-yl)-5-(tetrazol-1-yl)-benzamide
N-(2-Methylbutan-2-yl)-3-(4-propan-2-ylphenyl)-5-(tetrazol-1-yl)-benzamide
3-(4-Cyclopropylphenyl)-N-(2-methylbutan-2-yl)-5-(tetrazol-1-yl)-benzamide
N-(2-Methylbutan-2-yl)-3-(4-methylphenyl)-5-(5-propan-2-yltetrazol-1-yl)-benzamide
3-(4-Chlorophenyl)-N-(2-methylbutan-2-yl)-5-(tetrazol-1-yl)-benzamide
N-(2-methylbutan-2-yl)-3-(4-methylphenyl)-5-(5-methyltetrazol-1-yl)-benzamide
3-(5-Cyclopropyltetrazol-1-yl)-N-(2-methylbutan-2-yl)-5-(4-methylphenyl)-benzamide
3-(5-Ethyltetrazol-1-yl)-N-(2-methylbutan-2-yl)-5-(4-methylphenyl)-benzamide
3-(4-Chloro-3-fluorophenyl)-N-(2-methylbutan-2-yl)-5-(tetrazol-1-yl)-benzamide
3-(3,4-Dichlorophenyl)-N-(2-methylbutan-2-yl)-5-(tetrazol-1-yl)-benzamide
3-(3,4-Difluorophenyl)-N-(2-methylbutan-2-yl)-5-(tetrazol-1-yl)-benzamide
3-(3-Chloro-4-fluorophenyl)-N-(2-methylbutan-2-yl)-5-(tetrazol-1-yl)-benzamide
3-(4-Chlorophenyl)-N-(2-methylbutan-2-yl)-5-(5-propan-2-yltetrazol-1-yl)-benzamide
N-(2-Methylbutan-2-yl)-3-(5-propan-2-yltetrazol-1-yl)-5-[4-(trifluoro-methyl)-phenyl]-benzamide
3-(4-Chlorophenyl)-5-(5-cyclopropyltetrazol-1-yl)-N-(2-methylbutan-2-yl)-benzamide
3-(4-Fluorophenyl)-N-(2-methylbutan-2-yl)-5-(5-propan-2-yltetrazol-1-yl)-benzamide
3-(4-Chlorophenyl)-N-(2-methylbutan-2-yl)-5-(5-methyl-tetrazol-1-yl)-benzamide
3-(5-Cyclopropyltetrazol-1-yl)-5-(4-fluorophenyl)-N-(2-methylbutan-2-yl)-benzamide
3-(4-Chlorophenyl)-N-(2-methylbutan-2-yl)-5-[5-(trifluoromethyl)-tetrazol-1-yl]-benzamide
3-(4-Fluorophenyl)-N-(2-methylbutan-2-yl)-5-(5-methyltetrazol-1-yl)-benzamide
3-(5-tert-Butyltetrazol-1-yl)-5-(4-chlorophenyl)-N-(2-methylbutan-2-yl)-benzamide
3-(5-tert-Butyltetrazol-1-yl)-5-(4-fluorophenyl)-N-(2-methylbutan-2-yl)-benzamide One further object of the invention are compounds of formula IA-3

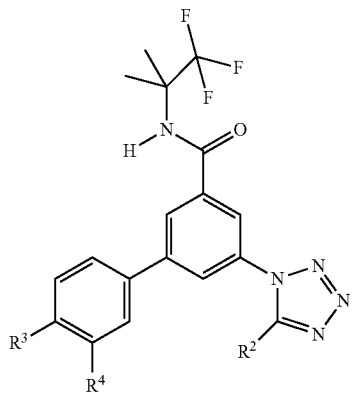

IA-3 wherein
$R^2$ is hydrogen, methyl, ethyl, isopropyl, tertbutyl, cyclopropyl or $CF_3$;
$R^3$ is Cl, F, $CF_3$, methyl, methoxy, isopropyl or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compounds 3-(4-Methylphenyl)-5-(tetrazol-1-yl)-N-(1,1,1-trifluoro-2-methylpropan-2-yl)-benzamide
3-(4-Fluorophenyl)-5-(tetrazol-1-yl)-N-(1,1,1-trifluoro-2-methylpropan-2-yl)-benzamide
3-(4-Methylphenyl)-5-(5-propan-2-yltetrazol-1-yl)-N-(1,1,1-trifluoro-2-methylpropan-2-yl)-benzamide
3-(5-Cyclopropyltetrazol-1-yl)-5-(4-methylphenyl)-N-(1,1,1-trifluoro-2-methylpropan-2-yl)-benzamide
3-(5-Ethyltetrazol-1-yl)-5-(4-methylphenyl)-N-(1,1,1-trifluoro-2-methylpropan-2-yl)-benzamide
3-(4-Chlorophenyl)-5-(tetrazol-1-yl)-N-(1,1,1-trifluoro-2-methylpropan-2-yl)-benzamide
3-(4-Chlorophenyl)-5-(5-propan-2-yltetrazol-1-yl)-N-(1,1,1-trifluoro-2-methylpropan-2-yl)-benzamide
3-(5-Propan-2-yltetrazol-1-yl)-5-[4-(trifluoromethyl)-phenyl]-N-(1,1,1-trifluoro-2-methylpropan-2-yl)-benzamide
3-(4-Chlorophenyl)-5-(5-cyclopropyltetrazol-1-yl)-N-(1,1,1-trifluoro-2-methylpropan-2-yl)-benzamide 3-(4-Fluorophenyl)-5-(5-propan-2-yltetrazol-1-yl)-N-(1,1,1-trifluoro-2-methylpropan-2-yl)-benzamide
3-(4-Chlorophenyl)-5-(5-methyltetrazol-1-yl)-N-(1,1,1-trifluoro-2-methylpropan-2-yl)-benzamide
3-(5-Cyclopropyltetrazol-1-yl)-5-(4-fluorophenyl)-N-(1,1,1-trifluoro-2-methylpropan-2-yl)-benzamide
3-(4-Chlorophenyl)-N-(1,1,1-trifluoro-2-methylpropan-2-yl)-5-[5-(trifluoromethyl)tetrazol-1-yl]-benzamide
3-(4-Fluorophenyl)-5-(5-methyltetrazol-1-yl)-N-(1,1,1-trifluoro-2-methylpropan-2-yl)-benzamide
3-(5-tert-Butyltetrazol-1-yl)-5-(4-chlorophenyl)-N-(1,1,1-trifluoro-2-methylpropan-2-yl)-benzamide
3-(5-tert-Butyltetrazol-1-yl)-5-(4-fluorophenyl)-N-(1,1,1-trifluoro-2-methylpropan-2-yl)-benzamide
3-(5-tert-Butyltetrazol-1-yl)-5-[4-(trifluoromethyl)-phenyl]-N-(1,1,1-trifluoro-2-methylpropan-2-yl)-benzamide
3-(5-tert-Butyltetrazol-1-yl)-5-(4-methylphenyl)-N-(1,1,1-trifluoro-2-methylpropan-2-yl)-benzamide
3-(5-tert-Butyltetrazol-1-yl)-5-(4-fluoro-3-methylphenyl)-N-(1,1,1-trifluoro-2-methylpropan-2-yl)-benzamide
3-(5-tert-Butyltetrazol-1-yl)-5-(4-chloro-3-fluorophenyl)-N-(1,1,1-trifluoro-2-methylpropan-2-yl)-benzamide or
3-(5-tert-Butyltetrazol-1-yl)-5-(3,4-difluorophenyl)-N-(1,1,1-trifluoro-2-methylpropan-2-yl)-benzamide.

One further object of the invention are compounds of formula IA-4

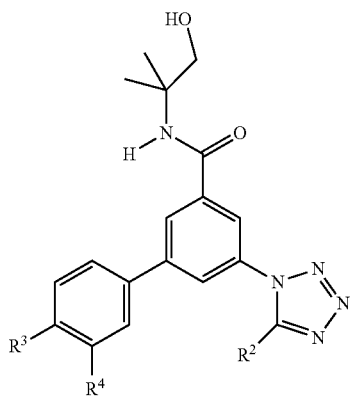

IA-4 wherein
R$^2$ is hydrogen, methyl, ethyl, isopropyl, tertbutyl, cyclopropyl or CF$_3$;
R$^3$ is Cl, F, CF$_3$, methyl, methoxy, isopropyl or cyclopropyl;
R$^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compounds
N-(1-Hydroxy-2-methylpropan-2-yl)-3-(4-methylphenyl)-5-(5-propan-2-yltetrazol-1-yl)-benzamide
3-(4-Chlorophenyl)-N-(1-hydroxy-2-methylpropan-2-yl)-5-(tetrazol-1-yl)-benzamide
3-(5-Cyclopropyltetrazol-1-yl)-N-(1-hydroxy-2-methylpropan-2-yl)-5-(4-methylphenyl)-benzamide
3-(4-Chlorophenyl)-N-(1-hydroxy-2-methylpropan-2-yl)-5-(5-propan-2-yltetrazol-1-yl)-benzamide
N-(1-Hydroxy-2-methylpropan-2-yl)-3-(5-propan-2-yltetrazol-1-yl)-5-[4-(trifluoromethyl)-phenyl]-benzamide
3-(4-Chlorophenyl)-5-(5-cyclopropyltetrazol-1-yl)-N-(1-hydroxy-2-methylpropan-2-yl)-benzamide
3-(4-Fluorophenyl)-N-(1-hydroxy-2-methylpropan-2-yl)-5-(5-propan-2-yltetrazol-1-yl)-benzamide
3-(4-Chlorophenyl)-N-(1-hydroxy-2-methylpropan-2-yl)-5-(5-methyl-tetrazol-1-yl)-benzamide
3-(5-Cyclopropyltetrazol-1-yl)-5-(4-fluorophenyl)-N-(1-hydroxy-2-methylpropan-2-yl)-benzamide
3-(4-Chlorophenyl)-N-(1-hydroxy-2-methylpropan-2-yl)-5-[5-(trifluoromethyl)-tetrazol-1-yl]-benzamide
3-(4-Fluorophenyl)-N-(1-hydroxy-2-methylpropan-2-yl)-5-(5-methyltetrazol-1-yl)-benzamide
3-(5-tert-Butyltetrazol-1-yl)-5-(4-chlorophenyl)-N-(1-hydroxy-2-methylpropan-2-yl)-benzamide or
3-(5-tert-Butyltetrazol-1-yl)-5-(4-fluorophenyl)-N-(1-hydroxy-2-methylpropan-2-yl)-benzamide.

One further object of the invention are compounds of formula IA-5

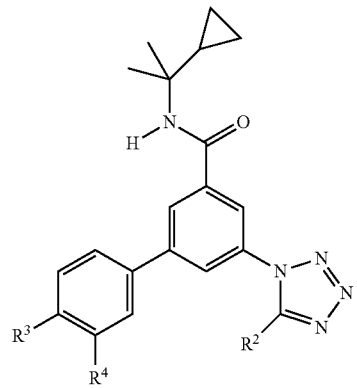

IA-5 wherein
R$^2$ is hydrogen, methyl, ethyl, isopropyl, tertbutyl, cyclopropyl or CF$_3$;
R$^3$ is Cl, F, CF$_3$, methyl, methoxy, isopropyl or cyclopropyl;
R$^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compounds
N-(2-Cyclopropylpropan-2-yl)-3-(4-methylphenyl)-5-(5-propan-2-yltetrazol-1-yl)-benzamide
N-(2-cyclopropylpropan-2-yl)-3-(4-fluorophenyl)-5-(tetrazol-1-yl)-benzamide
3-(4-Chlorophenyl)-N-(2-cyclopropylpropan-2-yl)-5-(tetrazol-1-yl)-benzamide
N-(2-Cyclopropylpropan-2-yl)-3-(5-cyclopropyltetrazol-1-yl)-5-(4-methylphenyl)-benzamide
N-(2-Cyclopropylpropan-2-yl)-3-(5-ethyltetrazol-1-yl)-5-(4-methylphenyl)-benzamide
3-(4-Chlorophenyl)-N-(2-cyclopropylpropan-2-yl)-5-(5-propan-2-yltetrazol-1-yl)-benzamide
N-(2-Cyclopropylpropan-2-yl)-3-(5-propan-2-yltetrazol-1-yl)-5-[4-(trifluoromethyl)phenyl]benzamide
N-(2-Cyclopropylpropan-2-yl)-3-(5-cyclopropyltetrazol-1-yl)-5-(4-fluorophenyl)-benzamide
3-(4-Chlorophenyl)-N-(2-cyclopropylpropan-2-yl)-5-(5-cyclopropyl-tetrazol-1-yl)-benzamide
N-(2-Cyclopropylpropan-2-yl)-3-(4-fluorophenyl)-5-(5-propan-2-yltetrazol-1-yl)-benzamide
3-(4-Chlorophenyl)-N-(2-cyclopropylpropan-2-yl)-5-(5-methyltetrazol-1-yl)-benzamide N-(2-Cyclopropylpropan-2-yl)-3-(4-fluorophenyl)-5-(5-methyltetrazol-1-yl)-benzamide 3-(5-tert-Butyltetrazol-1-yl)-5-(4-chlorophenyl)-N-(2-cyclopropylpropan-2-yl)-benzamide 3-(5-tert-Butyltetrazol-1-yl)-N-(2-cyclopropylpropan-2-yl)-5-(4-methylphenyl)-benzamide 3-(5-tert-Butyltetrazol-1-yl)-N-(2-cyclopropylpropan-2-yl)-5-(4-fluoro-3-methylphenyl)-benzamide 3-(5-tert-Butyltetrazol-1-yl)-N-(2-cyclopropylpropan-2-yl)-5-[4-(trifluoromethyl)-phenyl]-benzamide 3-(5-tert-Butyltetrazol-1-yl)-5-(4-chloro-3-fluorophenyl)-N-(2-cyclopropylpropan-2-yl)-benzamide 3-(5-tert-Butyltetrazol-1-yl)-N-(2-cyclopropylpropan-2-yl)-5-(3,4-difluorophenyl)-benzamide 3-(5-tert-Butyltetrazol-1-yl)-5-(4-cyclopropylphenyl)-N-(2-cyclopropylpropan-2-yl)-benzamide or 3-(5-tert-Butyltetrazol-1-yl)-N-(2-cyclopropylpropan-2-yl)-5-(3-fluoro-4-methylphenyl)-benzamide.

One further object of the invention are compounds of formula IA-6

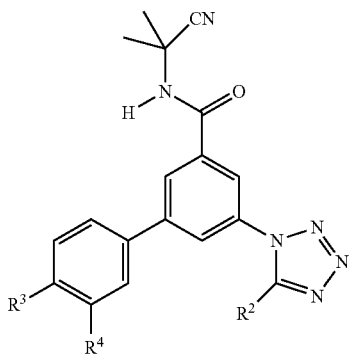

IA-6 wherein
$R^2$ is hydrogen, methyl, ethyl, isopropyl, tertbutyl, cyclopropyl or $CF_3$;
$R^3$ is Cl, F, $CF_3$, methyl, methoxy, isopropyl or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compounds 3-(5-tert-Butyltetrazol-1-yl)-N-(2-cyanopropan-2-yl)-5-(4-fluorophenyl)-benzamide 3-(4-Chlorophenyl)-N-(2-cyanopropan-2-yl)-5-(5-propan-2-yltetrazol-1-yl)-benzamide 3-(5-tert-Butyltetrazol-1-yl)-N-(2-cyanopropan-2-yl)-5-[4-(trifluoromethyl)-phenyl]benzamide 3-(5-tert-Butyltetrazol-1-yl)-5-(4-chloro-3-fluorophenyl)-N-(2-cyanopropan-2-yl)-benzamide or 3-(5-tert-Butyltetrazol-1-yl)-N-(2-cyanopropan-2-yl)-5-(3,4-difluorophenyl)-benzamide.

One further object of the invention are compounds of formula IA-7 for use in the treatment of schizophrenia, obsessive-compulsive disorder or autism

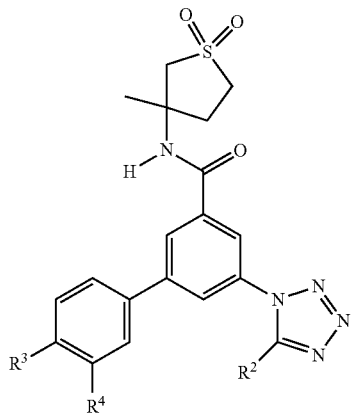

wherein
$R^2$ is hydrogen, methyl, ethyl, isopropyl, tertbutyl, cyclopropyl or $CF_3$;
$R^3$ is Cl, F, $CF_3$, methyl, methoxy, isopropyl or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the following compounds (RS)-3-(4-Fluorophenyl)-N-(3-methyl-1,1-dioxothiolan-3-yl)-5-(tetrazol-1-yl)-benzamide (RS)-3-(4-Chlorophenyl)-N-(3-methyl-1,1-dioxothiolan-3-yl)-5-(tetrazol-1-yl)-benzamide (RS)—N-(3-methyl-1,1-dioxothiolan-3-yl)-3-(4-methylphenyl)-5-(5-propan-2-yltetrazol-1-yl)-benzamide (RS)—N-(3-Methyl-1,1-dioxothiolan-3-yl)-3-(4-methylphenyl)-5-(5-methyltetrazol-1-yl)-benzamide (RS)-3-(5-Cyclopropyltetrazol-1-yl)-N-(3-methyl-,1-dioxothiolan-3-yl)-5-(4-methylphenyl)-benzamide (RS)-3-(5-Ethyltetrazol-1-yl)-N-(3-methyl-1,1-dioxothiolan-3-yl)-5-(4-methylphenyl)-benzamide (RS)-3-(4-Chlorophenyl)-N-(3-methyl-1,1-dioxothiolan-3-yl)-5-(5-propan-2-yltetrazol-1-yl)benzamide (RS)—N-(3-methyl-1,1-dioxothiolan-3-yl)-3-(5-propan-2-yltetrazol-1-yl)-5-[4-(trifluoromethyl)phenyl]benzamide (RS)-3-(4-Chlorophenyl)-5-(5-cyclopropyltetrazol-1-yl)-N-(3-methyl-1,1-dioxothiolan-3-yl)-benzamide (RS)-3-(4-Fluorophenyl)-N-(3-methyl-1,1-dioxothiolan-3-yl)-5-(5-propan-2-yltetrazol-1-yl)-benzamide (RS)-3-(4-Chlorophenyl)-N-(3-methyl-1,1-dioxothiolan-3-yl)-5-(5-methyltetrazol-1-yl)-benzamide (RS)-3-(5-Cyclopropyltetrazol-1-yl)-5-(4-fluorophenyl)-N-(3-methyl-1,1-dioxothiolan-3-yl)-benzamide (RS)-3-(4-Fluorophenyl)-N-(3-methyl-1,1-dioxothiolan-3-yl)-5-(5-methyltetrazol-1-yl)-benzamide (RS)-3-(5-tert-Butyltetrazol-1-yl)-5-(4-chlorophenyl)-N-(3-methyl-1,1-dioxothiolan-3-yl)benzamide or (RS)-3-(5-tert-Butyltetrazol-1-yl)-5-(4-fluorophenyl)-N-(3-methyl-1,1-dioxothiolan-3-yl)-benzamide.

The preparation of compounds of formula IA of the present invention may be carried out in sequential or convergent synthetic routes. Syntheses of the compounds of the invention are shown in the following schemes 1 and 2. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises a) reacting a compound of formula

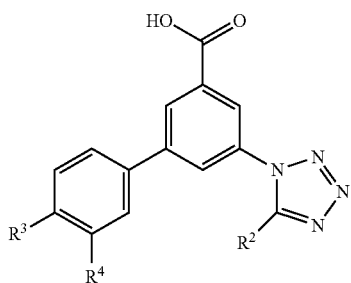

IX with a compound of formula

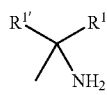

X to a compound of formula I

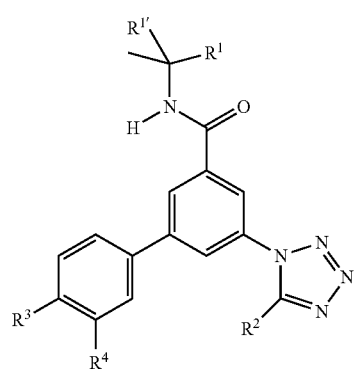

I wherein the substituents are as described above, or if desired, converting the compounds obtained into pharmaceutically acceptable acid addition salts.

b) reacting a compound of formula

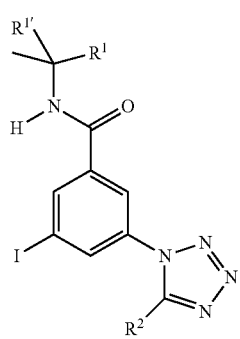

XIII with a compound of formula

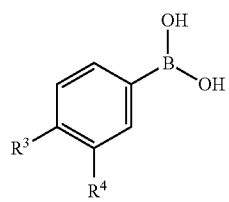

III to a compound of formula I

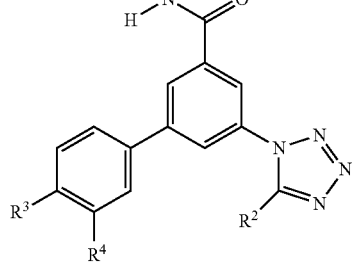

I wherein the substituents are described above, or if desired, converting the compounds obtained into pharmaceutically acceptable acid addition salts.

The preparation of compounds of formula I is further described in more detail in scheme 1 to 4 and in examples 1-123.

The tetrazole derivatives I can be prepared from the intermediate acids IX by amide formation with the commercially available amines X using standard reagents like N,N-diisopropylethyl amine and O-(benzotriazol-1-yl)-N,N,N',N'-tetramethyluronium tetrafluoroborate (TBTU).

Scheme 1

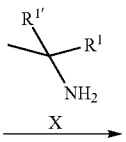

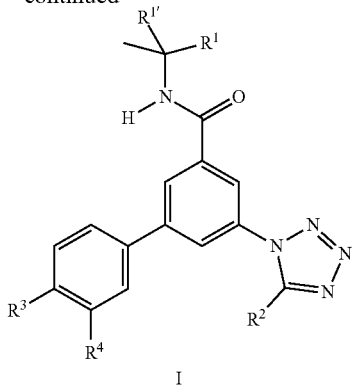

I

The acids IX can be prepared starting from commercially available 3-iodo-5-nitrobenzoic acid II. Coupling reaction with commercially available boronic acid derivatives III led to the acids IV which were subsequently esterified using standard procedure like thionyl chloride in methanol. The methyl esters V can be reduced with tin(II)chloride to yield the aniline derivatives VI. Tetrazole formation can be achieved using sodium azide and triethyl orthoformate in case of the unsubstituted derivatives VIIa, whereas for the substituted tetrazole derivatives VIIb the anilines VI can be transformed into the amides VIII using standard methods like acyl chlorides and triethylamine, and subsequent tetrazole formation can be achieved using sodium azide and silicium tetrachloride. Transformation of the esters VIIa/VIIb into the acids IX can be achieved by standard methods like lithium hydroxide in water/THF.

Scheme 2

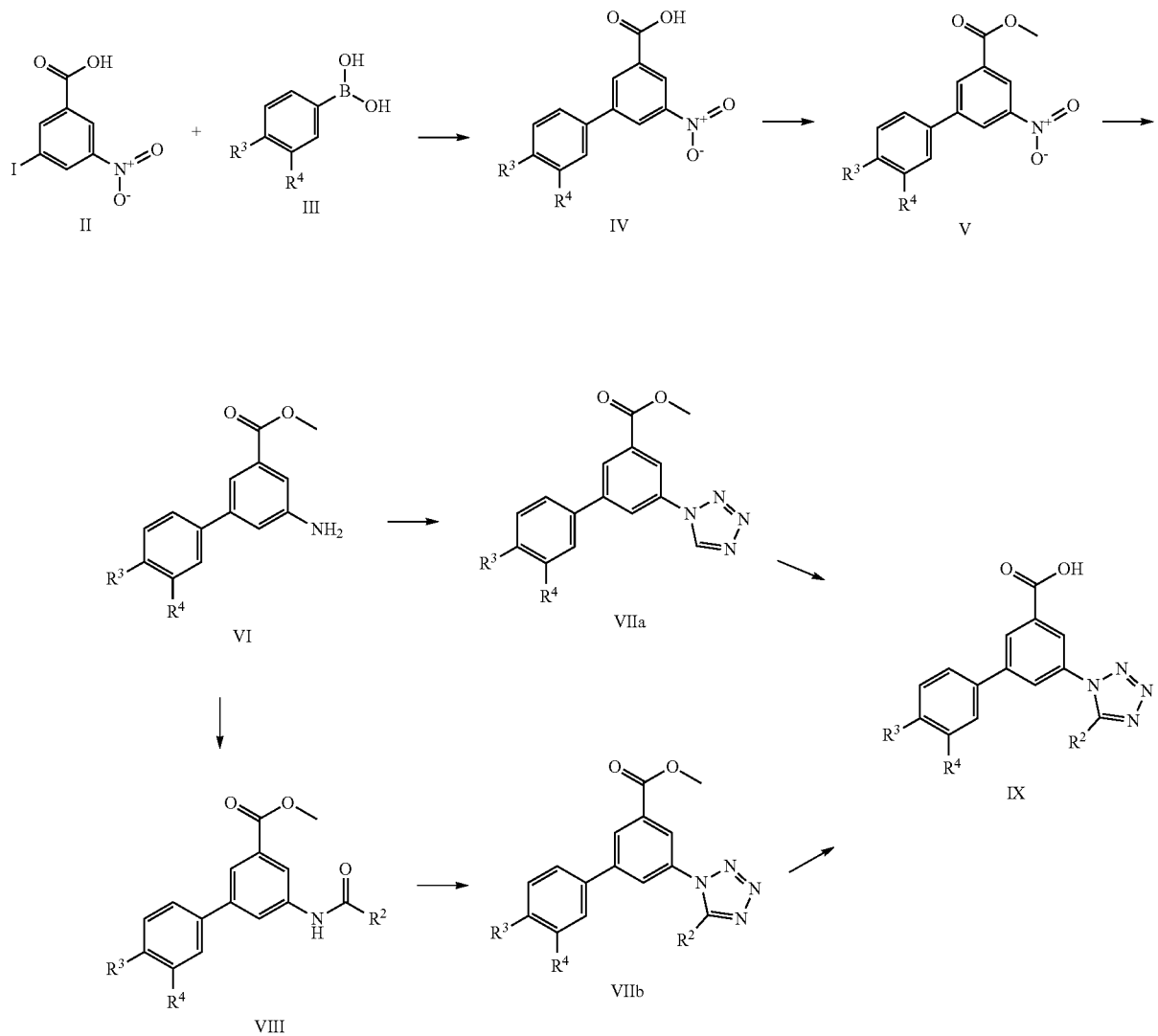

Another method to prepare the tetrazoles I can be the coupling reaction of the iodo- or bromo-derivatives XIII or XVI with the commercially available boronic acid derivatives III. The iodo derivatives XIII can be prepared starting from the commercially available 3-iodo-5-nitrobenzoic acid II. Amide formation with the commercially available amines X using standard conditions leads to the amides XI which can be reduced with tin(II)chloride to yield the aniline derivatives XII. Tetrazole formation can be achieved as described above for the derivatives VII to yield the iodo intermediates XIII.

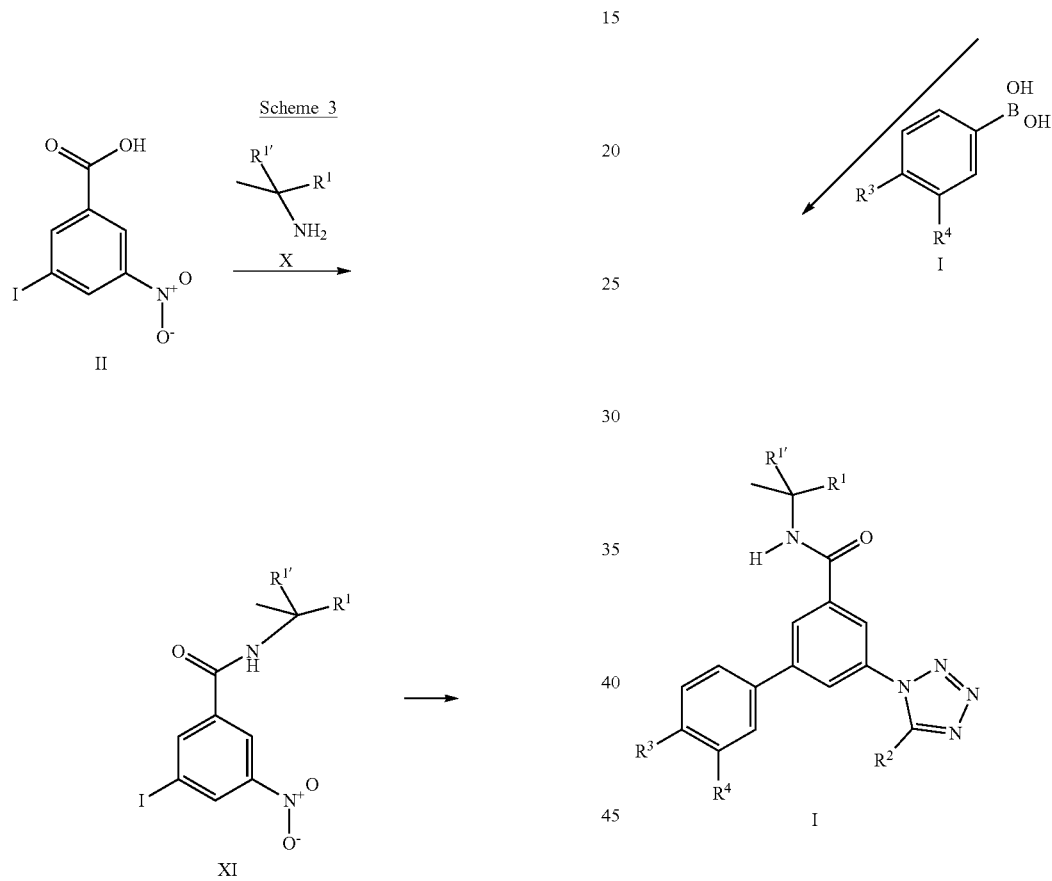

The corresponding bromo derivatives XVI can be prepared starting from commercially available 3-amino-5-bromobenzoic acid XIV which can be transformed into the bromo derivatives XVI via the amides XV as described above for the derivatives VII.

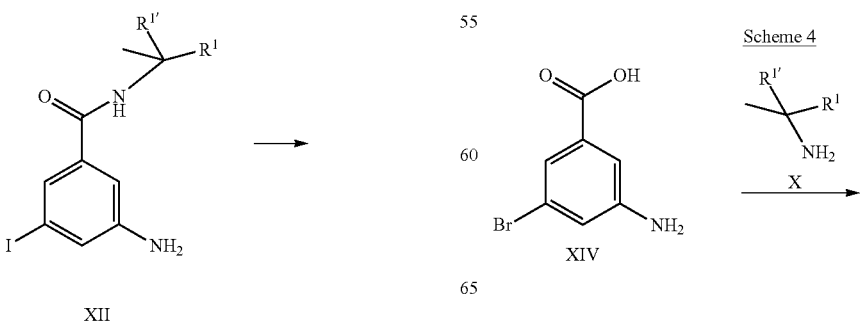

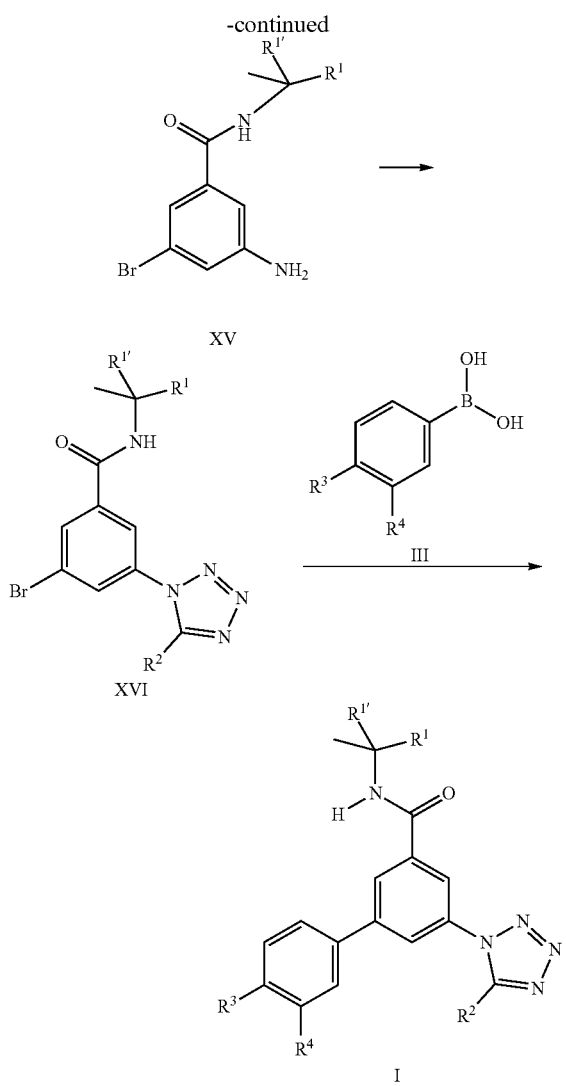

Generally speaking, the sequence of steps used to synthesize the compounds of formula I can also be modified in certain cases.

The compounds of formula I and their pharmaceutically usable addition salts possess valuable pharmaceutical properties. Specifically, it has been found that the compounds of the present invention are EAAT3 inhibitors for use in the treatment of schizophrenia, bipolar disorder, obsessive-compulsive disorder or autism spectrum disorders.

The compounds were investigated in accordance with the test given hereinafter.

Biological Assay and Data

The FLIPR Membrane Potential (FMP) Assay

HEK-293 cells stably expressing human EAAT3 were seeded at 55 000 cells/well in growth medium (DMEM glutamate free (Invitrogen 11960-044), 1% Pen Strep (10 ml/l GIBCO BRL No 15140-023), 10% FCS non dialysed heat inactivated, 5 mg/l puromycin) in poly-D-lysine treated 96-well black microtiter plates with clear-bottom. After 24 h, the growth medium was removed and 100 µl/well of Krebs buffer (140 mM NaCl, 4.7 mM KCl, 2.5 mM $CaCl_2$, 1.2 mM $MgCl_2$, 11 mM HEPES, 10 mM D-glucose, pH=7.4) added. The cells were then loaded by adding 100 µl/well FMP assay dye (FLIPR Membrane Potential assay reagent, Molecular Devices). The 96-well plates were then incubated at 37° C. for 1 h. The depolarization of the cells will cause more dye to enter in the cells, where it will bind to intracellular proteins and lipids and cause an increase in the fluorescence signal. Antagonist potency at human EAAT3 was determined by using L-glutamate as agonist at a concentration which gives 80% of the maximum response. The antagonists were applied 15 min before the application of the agonist L-glutamate. The assays were performed at room temperature and measurements done by using a Fluorometric Imaging Plate Reader (FLIPR, Molecular Devices) and filter #2. Responses were measured as peak increase in fluorescence minus basal (i.e. fluorescence without addition of L-glutamate). Kb was determined using the Cheng-Prusoff equation $Kb=IC_{50}/[1+(A/EC_{50})]$, where $IC_{50}$ is the concentration of the antagonist producing 50% inhibition, A is the concentration of the agonist against which the $IC_{50}$ is being determined (at $EC_{80}$) and $EC_{50}$ is the concentration of the agonist producing 50% inhibition.

List of Examples and Data

| | Structure | Name | EAAT3 Kb [uM] |
|---|---|---|---|
| 1 | 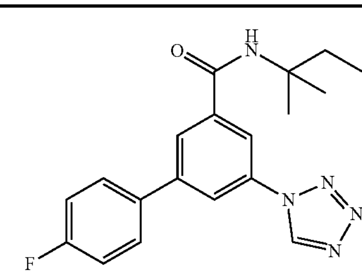 | 3-(4-Fluorophenyl)-N-(2-methylbutan-2-yl)-5-(tetrazol-1-yl)-benzamide | 0.145 |

-continued

| | Structure | Name | EAAT3 Kb [uM] |
|---|---|---|---|
| 2 | 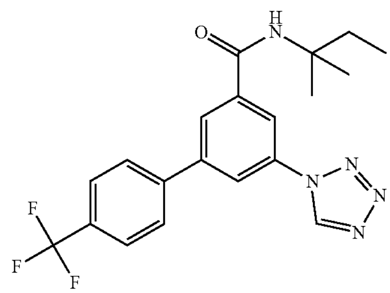 [SMILES: CCC(C)(C)NC(=O)c1cc(-c2ccc(C(F)(F)F)cc2)cc(-n2cnnn2)c1] | N-(2-Methylbutan-2-yl)-3-(tetrazol-1-yl)-5-[4-(trifluoromethyl)phenyl]-benzamide | 0.22 |
| 3 | 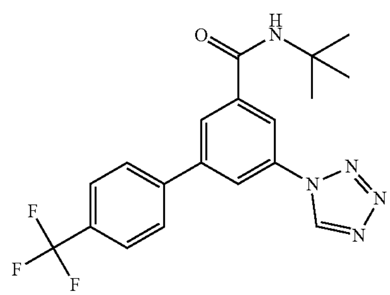 [SMILES: CC(C)(C)NC(=O)c1cc(-c2ccc(C(F)(F)F)cc2)cc(-n2cnnn2)c1] | N-tert-Butyl-3-(tetrazol-1-yl)-5-[4-(trifluoromethyl)phenyl]-benzamide | 0.47 |
| 4 | 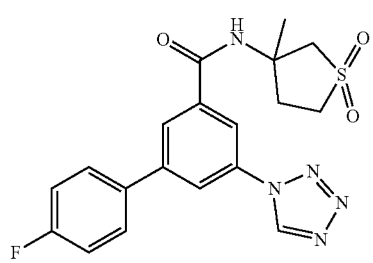 [SMILES: CC1(NC(=O)c2cc(-c3ccc(F)cc3)cc(-n3cnnn3)c2)CCS(=O)(=O)C1] | (RS)-3-(4-Fluorophenyl)-N-(3-methyl-1,1-dioxothiolan-3-yl)-5-(tetrazol-1-yl)-benzamide | 0.46 |
| 5 | 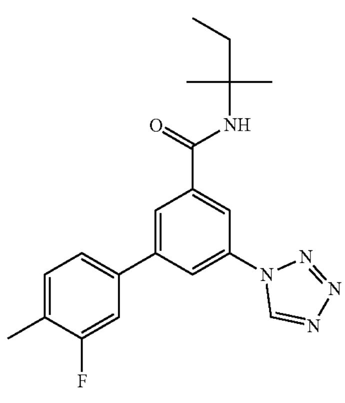 [SMILES: CCC(C)(C)NC(=O)c1cc(-c2ccc(C)c(F)c2)cc(-n2cnnn2)c1] | 3-(3-Fluoro-4-methylphenyl)-N-(2-methylbutan-2-yl)-5-(tetrazol-1-yl)-benzamide | 0.25 |

-continued

| | Structure | Name | EAAT3 Kb [uM] |
|---|---|---|---|
| 6 | 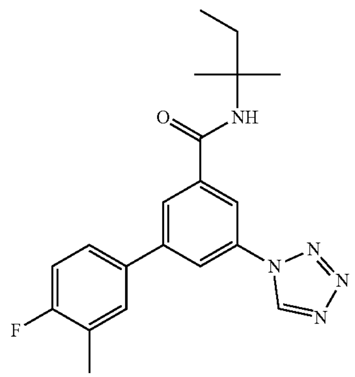 [SMILES: CCC(C)(C)NC(=O)c1cc(-c2ccc(F)c(C)c2)cc(-n2cnnn2)c1] | 3-(4-Fluoro-3-methylphenyl)-N-(2-methylbutan-2-yl)-5-(tetrazol-1-yl)-benzamide | 0.41 |
| 7 | 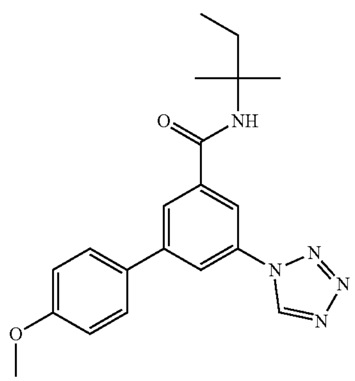 [SMILES: CCC(C)(C)NC(=O)c1cc(-c2ccc(OC)cc2)cc(-n2cnnn2)c1] | 3-(4-Methoxyphenyl)-N-(2-methylbutan-2-yl)-5-(tetrazol-1-yl)-benzamide | 0.41 |
| 8 | 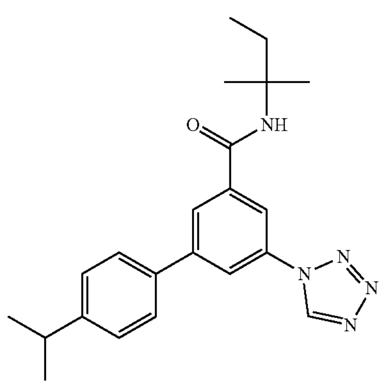 [SMILES: CCC(C)(C)NC(=O)c1cc(-c2ccc(C(C)C)cc2)cc(-n2cnnn2)c1] | N-(2-Methylbutan-2-yl)-3-(4-propan-2-ylphenyl)-5-(tetrazol-1-yl)-benzamide | 0.61 |
| 9 | 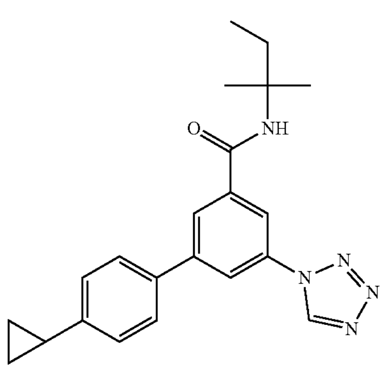 [SMILES: CCC(C)(C)NC(=O)c1cc(-c2ccc(C3CC3)cc2)cc(-n2cnnn2)c1] | 3-(4-Cyclopropylphenyl)-N-(2-methylbutan-2-yl)-5-(tetrazol-1-yl)-benzamide | 0.54 |

-continued

| | Structure | Name | EAAT3 Kb [uM] |
|---|---|---|---|
| 10 | 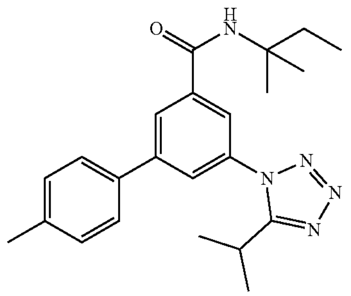 [SMILES: CCC(C)(C)NC(=O)c1cc(-c2ccc(C)cc2)cc(-n2nnnc2C(C)C)c1] | N-(2-Methylbutan-2-yl)-3-(4-methylphenyl)-5-(5-propan-2-yltetrazol-1-yl)-benzamide | 0.23 |
| 11 | 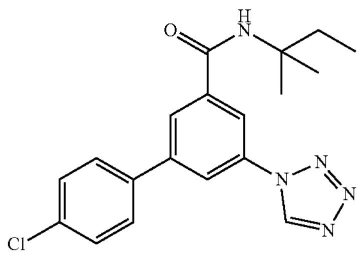 [SMILES: CCC(C)(C)NC(=O)c1cc(-c2ccc(Cl)cc2)cc(-n2cnnn2)c1] | 3-(4-Chlorophenyl)-N-(2-methylbutan-2-yl)-5-(tetrazol-1-yl)-benzamide | 0.076 |
| 12 | 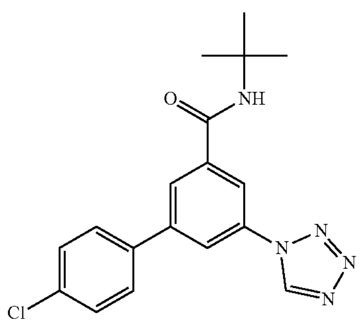 [SMILES: CC(C)(C)NC(=O)c1cc(-c2ccc(Cl)cc2)cc(-n2cnnn2)c1] | N-tert-Butyl-3-(4-chlorophenyl)-5-(tetrazol-1-yl)-benzamide | 0.35 |
| 13 | 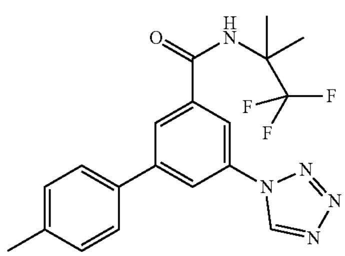 [SMILES: Cc1ccc(-c2cc(C(=O)NC(C)(C)C(F)(F)F)cc(-n3cnnn3)c2)cc1] | 3-(4-Methylphenyl)-5-(tetrazol-1-yl)-N-(1,1,1-trifluoro-2-methylpropan-2-yl)-benzamide | 0.65 |
| 14 | 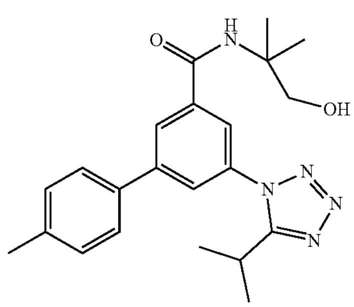 [SMILES: Cc1ccc(-c2cc(C(=O)NC(C)(C)CO)cc(-n3nnnc3C(C)C)c2)cc1] | N-(1-Hydroxy-2-methylpropan-2-yl)-3-(4-methylphenyl)-5-(5-propan-2-yltetrazol-1-yl)-benzamide | 0.65 |

-continued

| | Structure | Name | EAAT3 Kb [uM] |
|---|---|---|---|
| 15 | 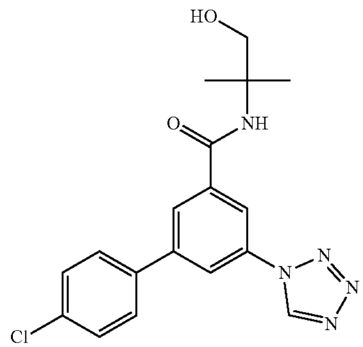 [SMILES: CC(C)(CO)NC(=O)c1cc(-c2ccc(Cl)cc2)cc(-n2cnnn2)c1] | 3-(4-Chlorophenyl)-N-(1-hydroxy-2-methylpropan-2-yl)-5-(tetrazol-1-yl)-benzamide | 0.8 |
| 16 | 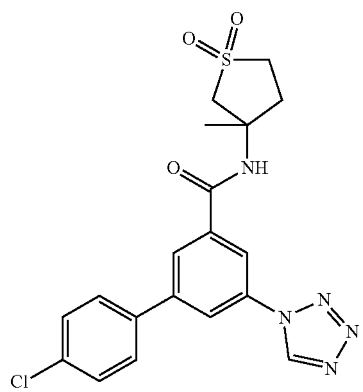 [SMILES: CC1(NC(=O)c2cc(-c3ccc(Cl)cc3)cc(-n3cnnn3)c2)CCS(=O)(=O)C1] | (RS)-3-(4-Chlorophenyl)-N-(3-methyl-1,1-dioxothiolan-3-yl)-5-(tetrazol-1-yl)-benzamide | 0.63 |
| 17 | 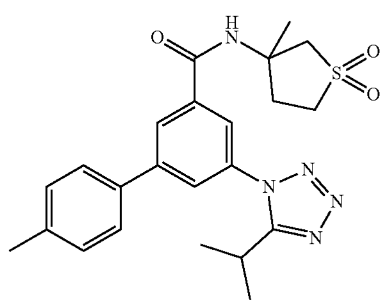 [SMILES: Cc1ccc(-c2cc(C(=O)NC3(C)CCS(=O)(=O)C3)cc(-n3nnnc3C(C)C)c2)cc1] | (RS)-N-(3-methyl-1,1-dioxothiolan-3-yl)-3-(4-methylphenyl)-5-(5-propan-2-yltetrazol-1-yl)-benzamide | 0.25 |
| 18 | 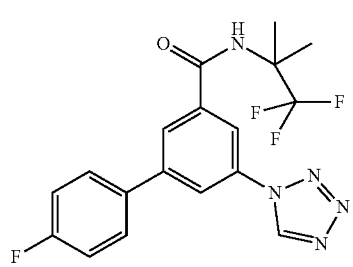 [SMILES: CC(C)(NC(=O)c1cc(-c2ccc(F)cc2)cc(-n2cnnn2)c1)C(F)(F)F] | 3-(4-Fluorophenyl)-5-(tetrazol-1-yl)-N-(1,1,1-trifluoro-2-methylpropan-2-yl)-benzamide | 0.43 |

| | Structure | Name | EAAT3 Kb [uM] |
|---|---|---|---|
| 19 | 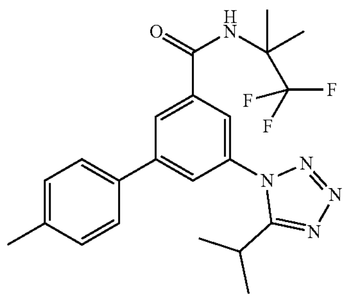 [SMILES: Cc1ccc(-c2cc(C(=O)NC(C)(C)C(F)(F)F)cc(-n3nnnc3C(C)C)c2)cc1] | 3-(4-Methylphenyl)-5-(5-propan-2-yltetrazol-1-yl)-N-(1,1,1-trifluoro-2-methylpropan-2-yl)-benzamide | 0.23 |
| 20 | 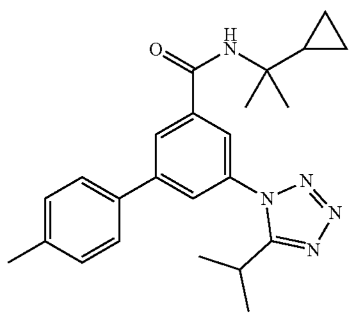 [SMILES: Cc1ccc(-c2cc(C(=O)NC(C)(C)C3CC3)cc(-n3nnnc3C(C)C)c2)cc1] | N-(2-Cyclopropylpropan-2-yl)-3-(4-methylphenyl)-5-(5-propan-2-yltetrazol-1-yl)-benzamide | 0.31 |
| 21 | 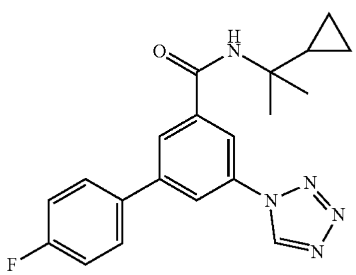 [SMILES: CC(C)(NC(=O)c1cc(-c2ccc(F)cc2)cc(-n2cnnn2)c1)C1CC1] | N-(2-cyclopropylpropan-2-yl)-3-(4-fluorophenyl)-5-(tetrazol-1-yl)-benzamide | 0.96 |
| 22 | 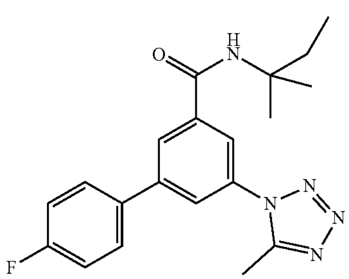 [SMILES: CCC(C)(C)NC(=O)c1cc(-c2ccc(F)cc2)cc(-n2nnnc2C)c1] | N-(2-methylbutan-2-yl)-3-(4-methylphenyl)-5-(5-methyltetrazol-1-yl)-benzamide | 0.15 |
| 23 | 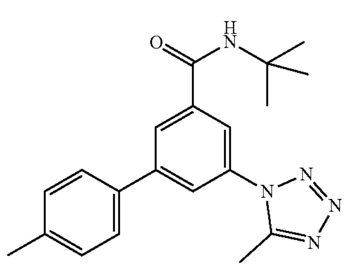 [SMILES: Cc1ccc(-c2cc(C(=O)NC(C)(C)C)cc(-n3nnnc3C)c2)cc1] | N-tert-Butyl-3-(4-methylphenyl)-5-(5-methyltetrazol-1-yl)-benzamide | 0.29 |

-continued

| | Structure | Name | EAAT3 Kb [uM] |
|---|---|---|---|
| 24 | 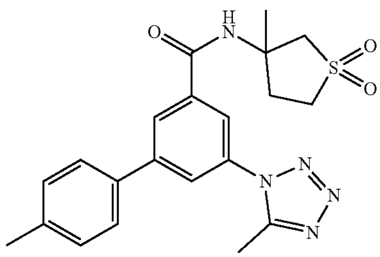 [SMILES: Cc1ccc(-c2cc(C(=O)NC3(C)CCS(=O)(=O)C3)cc(-n3nnnc3C)c2)cc1] | (RS)-N-(3-Methyl-1,1-dioxothiolan-3-yl)-3-(4-methylphenyl)-5-(5-methyltetrazol-1-yl)-benzamide | 0.38 |
| 25 | 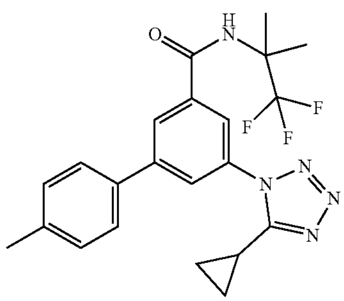 [SMILES: Cc1ccc(-c2cc(C(=O)NC(C)(C)C(F)(F)F)cc(-n3nnnc3C3CC3)c2)cc1] | 3-(5-Cyclopropyltetrazol-1-yl)-5-(4-methylphenyl)-N-(1,1,1-trifluoro-2-methylpropan-2-yl)-benzamide | 0.27 |
| 26 | 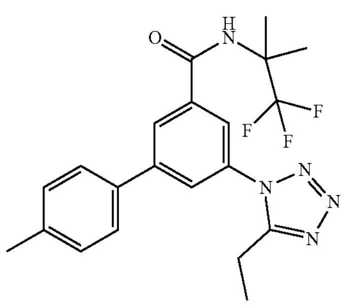 [SMILES: CCc1nnnn1-c1cc(C(=O)NC(C)(C)C(F)(F)F)cc(-c2ccc(C)cc2)c1] | 3-(5-Ethyltetrazol-1-yl)-5-(4-methylphenyl)-N-(1,1,1-trifluoro-2-methylpropan-2-yl)-benzamide | 0.3 |
| 27 | 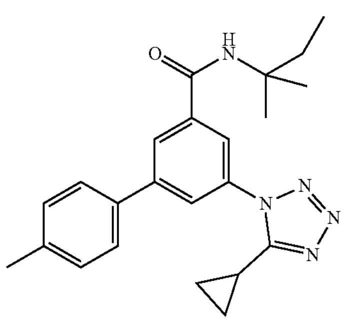 [SMILES: CCC(C)(C)NC(=O)c1cc(-c2ccc(C)cc2)cc(-n2nnnc2C2CC2)c1] | 3-(5-Cyclopropyltetrazol-1-yl)-N-(2-methylbutan-2-yl)-5-(4-methylphenyl)-benzamide | 0.2 |
| 28 | 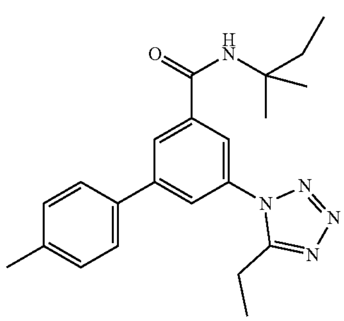 [SMILES: CCc1nnnn1-c1cc(C(=O)NC(C)(C)CC)cc(-c2ccc(C)cc2)c1] | 3-(5-Ethyltetrazol-1-yl)-N-(2-methylbutan-2-yl)-5-(4-methylphenyl)-benzamide | 0.14 |

-continued

| | Structure | Name | EAAT3 Kb [uM] |
|---|---|---|---|
| 29 | 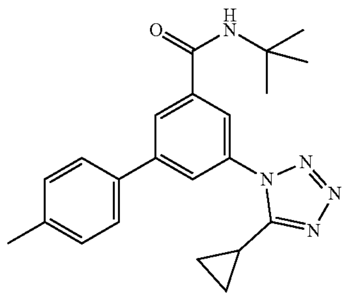 [SMILES: Cc1ccc(-c2cc(C(=O)NC(C)(C)C)cc(-n3nnnc3C3CC3)c2)cc1] | N-tert-Butyl-3-(5-cyclopropyltetrazol-1-yl)-5-(4-methylphenyl)-benzamide | 0.2 |
| 30 | 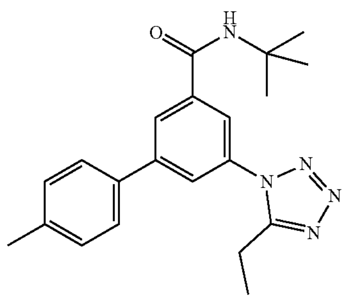 [SMILES: CCc1nnnn1-c1cc(C(=O)NC(C)(C)C)cc(-c2ccc(C)cc2)c1] | N-tert-Butyl-3-(5-ethyltetrazol-1-yl)-5-(4-methylphenyl)-benzamide | 0.21 |
| 31 | 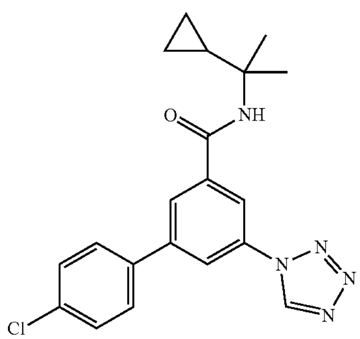 [SMILES: CC(C)(NC(=O)c1cc(-c2ccc(Cl)cc2)cc(-n2cnnn2)c1)C1CC1] | 3-(4-Chlorophenyl)-N-(2-cyclopropylpropan-2-yl)-5-(tetrazol-1-yl)-benzamide | 0.21 |
| 32 | 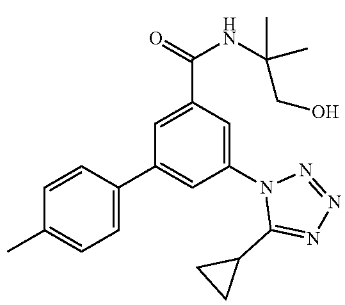 [SMILES: Cc1ccc(-c2cc(C(=O)NC(C)(C)CO)cc(-n3nnnc3C3CC3)c2)cc1] | 3-(5-Cyclopropyltetrazol-1-yl)-N-(1-hydroxy-2-methylpropan-2-yl)-5-(4-methylphenyl)-benzamide | 0.43 |
| 33 | 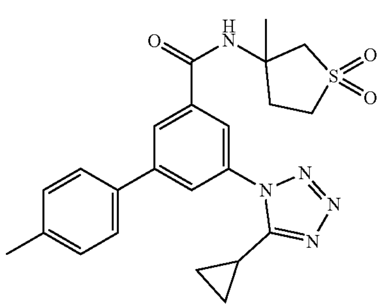 [SMILES: Cc1ccc(-c2cc(C(=O)NC3(C)CCS(=O)(=O)C3)cc(-n3nnnc3C3CC3)c2)cc1] | (RS)-3-(5-Cyclopropyltetrazol-1-yl)-N-(3-methyl-1,1-dioxothiolan-3-yl)-5-(4-methylphenyl)-benzamide | 0.3 |

| | Structure | Name | EAAT3 Kb [uM] |
|---|---|---|---|
| 34 | 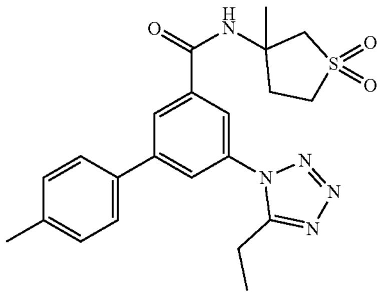 [SMILES: CCc1nnnn1-c1cc(C(=O)NC2(C)CCS(=O)(=O)C2)cc(-c2ccc(C)cc2)c1] | (RS)-3-(5-Ethyltetrazol-1-yl)-N-(3-methyl-1,1-dioxothiolan-3-yl)-5-(4-methylphenyl)-benzamide | 0.27 |
| 35 | 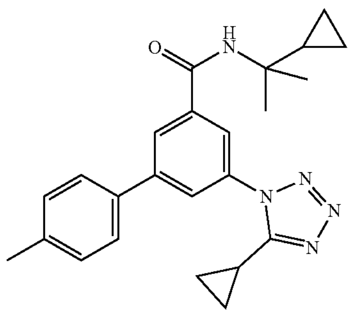 [SMILES: Cc1ccc(-c2cc(C(=O)NC(C)(C)C3CC3)cc(-n3nnnc3C3CC3)c2)cc1] | N-(2-Cyclopropylpropan-2-yl)-3-(5-cyclopropyltetrazol-1-yl)-5-(4-methylphenyl)-benzamide | 0.45 |
| 36 | 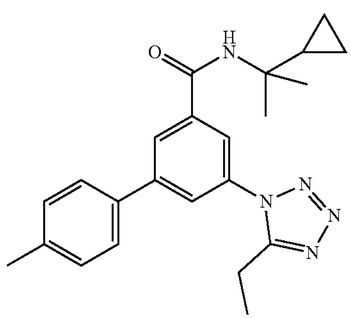 [SMILES: CCc1nnnn1-c1cc(C(=O)NC(C)(C)C2CC2)cc(-c2ccc(C)cc2)c1] | N-(2-Cyclopropylpropan-2-yl)-3-(5-ethyltetrazol-1-yl)-5-(4-methylphenyl)-benzamide | 0.35 |
| 37 | 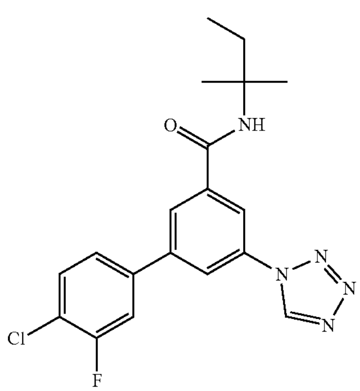 [SMILES: CCC(C)(C)NC(=O)c1cc(-c2ccc(Cl)c(F)c2)cc(-n2cnnn2)c1] | 3-(4-Chloro-3-fluorophenyl)-N-(2-methylbutan-2-yl)-5-(tetrazol-1-yl)-benzamide | 0.24 |

| | Structure | Name | EAAT3 Kb [uM] |
|---|---|---|---|
| 38 | 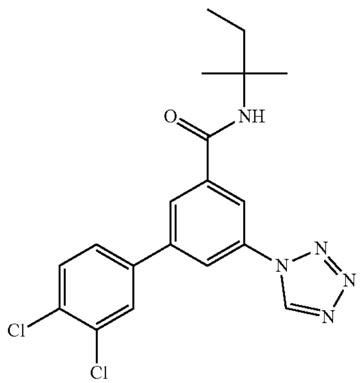 [SMILES: CCC(C)(C)NC(=O)c1cc(-c2ccc(Cl)c(Cl)c2)cc(-n2cnnn2)c1] | 3-(3,4-Dichlorophenyl)-N-(2-methylbutan-2-yl)-5-(tetrazol-1-yl)-benzamide | 0.7 |
| 39 | 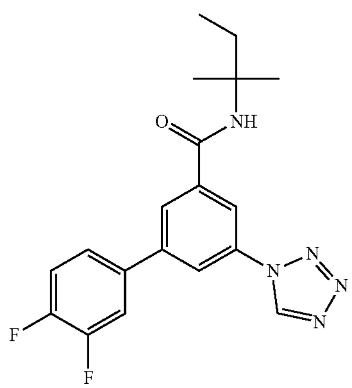 [SMILES: CCC(C)(C)NC(=O)c1cc(-c2ccc(F)c(F)c2)cc(-n2cnnn2)c1] | 3-(3,4-Difluorophenyl)-N-(2-methylbutan-2-yl)-5-(tetrazol-1-yl)-benzamide | 0.2 |
| 40 | 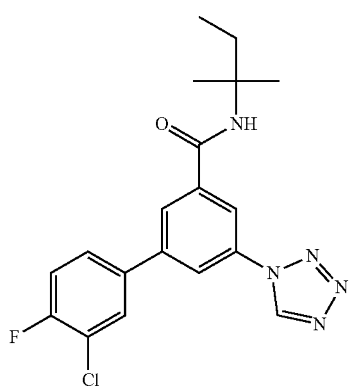 [SMILES: CCC(C)(C)NC(=O)c1cc(-c2ccc(F)c(Cl)c2)cc(-n2cnnn2)c1] | 3-(3-Chloro-4-fluorophenyl)-N-(2-methylbutan-2-yl)-5-(tetrazol-1-yl)-benzamide | 0.57 |
| 41 | 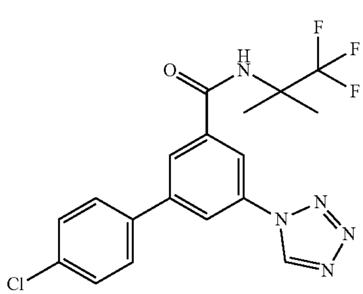 [SMILES: CC(C)(NC(=O)c1cc(-c2ccc(Cl)cc2)cc(-n2cnnn2)c1)C(F)(F)F] | 3-(4-Chlorophenyl)-5-(tetrazol-1-yl)-N-(1,1,1-trifluoro-2-methylpropan-2-yl)-benzamide | 0.35 |

-continued

| | Structure | Name | EAAT3 Kb [uM] |
|---|---|---|---|
| 42 | 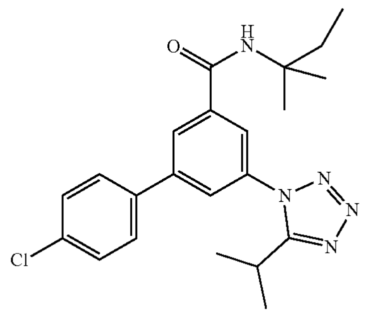 [SMILES: CCC(C)(C)NC(=O)c1cc(-c2ccc(Cl)cc2)cc(-n2nnnc2C(C)C)c1] | 3-(4-Chlorophenyl)-N-(2-methylbutan-2-yl)-5-(5-propan-2-yltetrazol-1-yl)-benzamide | 0.16 |
| 43 | 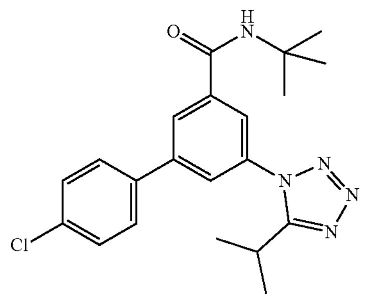 [SMILES: CC(C)c1nnnn1-c1cc(C(=O)NC(C)(C)C)cc(-c2ccc(Cl)cc2)c1] | N-tert-Butyl-3-(4-chlorophenyl)-5-(5-propan-2-yltetrazol-1-yl)-benzamide | 0.089 |
| 44 | 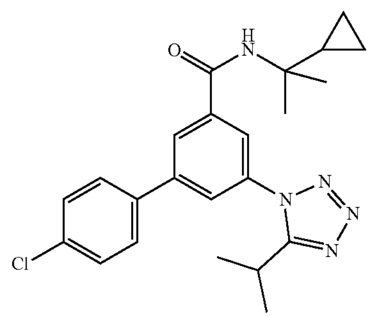 [SMILES: CC(C)c1nnnn1-c1cc(C(=O)NC(C)(C)C2CC2)cc(-c2ccc(Cl)cc2)c1] | 3-(4-Chlorophenyl)-N-(2-cyclopropylpropan-2-yl)-5-(5-propan-2-yltetrazol-1-yl)-benzamide | 0.21 |
| 45 | 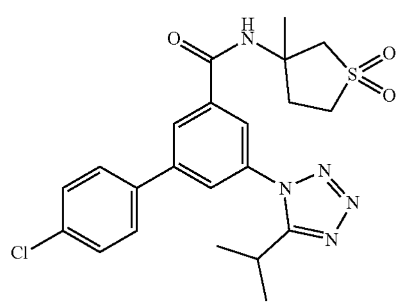 [SMILES: CC(C)c1nnnn1-c1cc(C(=O)NC2(C)CCS(=O)(=O)C2)cc(-c2ccc(Cl)cc2)c1] | (RS)-3-(4-Chlorophenyl)-N-(3-methyl-1,1-dioxothiolan-3-yl)-5-(5-propan-2-yltetrazol-1-yl)benzamide | 0.26 |
| 46 | 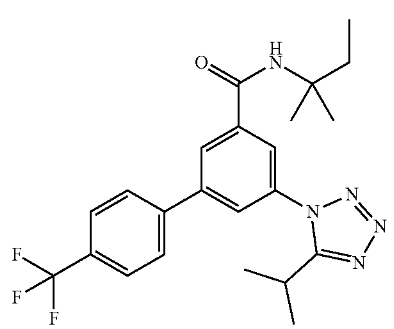 [SMILES: CCC(C)(C)NC(=O)c1cc(-c2ccc(C(F)(F)F)cc2)cc(-n2nnnc2C(C)C)c1] | N-(2-Methylbutan-2-yl)-3-(5-propan-2-yltetrazol-1-yl)-5-[4-(trifluoro-methyl)-phenyl]-benzamide | 0.19 |

-continued

| | Structure | Name | EAAT3 Kb [uM] |
|---|---|---|---|
| 47 | 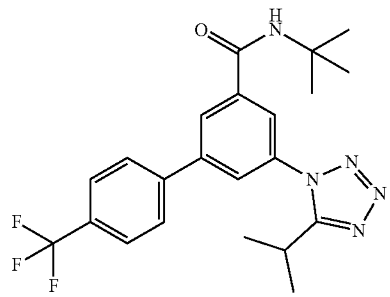 [SMILES: CC(C)c1nnnn1-c1cc(C(=O)NC(C)(C)C)cc(-c2ccc(C(F)(F)F)cc2)c1] | N-tert-Butyl-3-(5-propan-2-yltetrazol-1-yl)-5-[4-(trifluoromethyl)-phenyl]-benzamide | 0.27 |
| 48 | 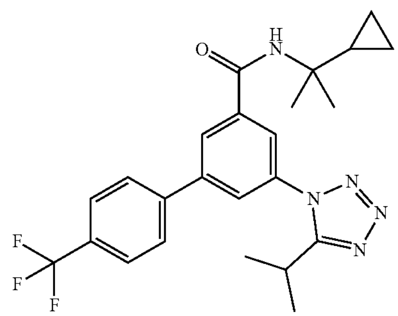 [SMILES: CC(C)c1nnnn1-c1cc(C(=O)NC(C)(C)C2CC2)cc(-c2ccc(C(F)(F)F)cc2)c1] | N-(2-Cyclopropylpropan-2-yl)-3-(5-propan-2-yltetrazol-1-yl)-5-[4-(trifluoromethyl)phenyl]benzamide | 0.42 |
| 49 | 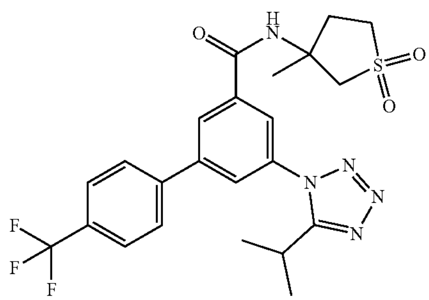 [SMILES: CC(C)c1nnnn1-c1cc(C(=O)NC2(C)CCS(=O)(=O)C2)cc(-c2ccc(C(F)(F)F)cc2)c1] | (RS)-N-(3-methyl-1,1-dioxothiolan-3-yl)-3-(5-propan-2-yltetrazol-1-yl)-5-[4-(trifluoromethyl)phenyl]benzamide | 0.33 |
| 50 | 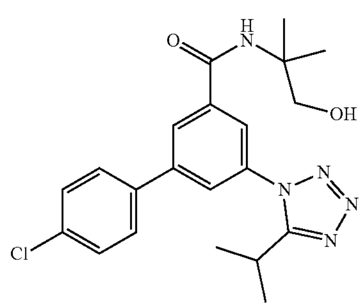 [SMILES: CC(C)c1nnnn1-c1cc(C(=O)NC(C)(C)CO)cc(-c2ccc(Cl)cc2)c1] | 3-(4-Chlorophenyl)-N-(1-hydroxy-2-methylpropan-2-yl)-5-(5-propan-2-yltetrazol-1-yl)-benzamide | 0.26 |
| 51 | 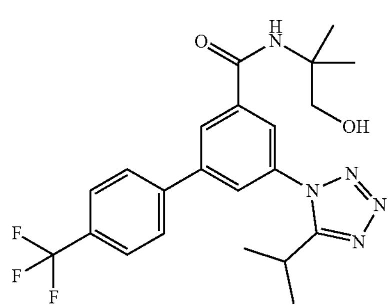 [SMILES: CC(C)c1nnnn1-c1cc(C(=O)NC(C)(C)CO)cc(-c2ccc(C(F)(F)F)cc2)c1] | N-(1-Hydroxy-2-methylpropan-2-yl)-3-(5-propan-2-yltetrazol-1-yl)-5-[4-(trifluoromethyl)-phenyl]-benzamide | 0.37 |

-continued

| | Structure | Name | EAAT3 Kb [uM] |
|---|---|---|---|
| 52 | 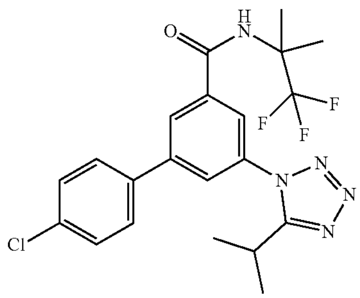 [SMILES: CC(C)c1nnnn1-c1cc(C(=O)NC(C)(C)C(F)(F)F)cc(-c2ccc(Cl)cc2)c1] | 3-(4-Chlorophenyl)-5-(5-propan-2-yltetrazol-1-yl)-N-(1,1,1-trifluoro-2-methylpropan-2-yl)-benzamide | 0.34 |
| 53 | 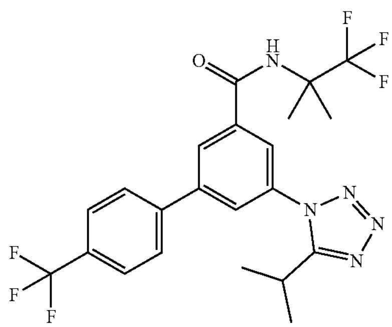 [SMILES: CC(C)c1nnnn1-c1cc(C(=O)NC(C)(C)C(F)(F)F)cc(-c2ccc(C(F)(F)F)cc2)c1] | 3-(5-Propan-2-yltetrazol-1-yl)-5-[4-(trifluoromethyl)-phenyl]-N-(1,1,1-trifluoro-2-methylpropan-2-yl)-benzamide | 0.48 |
| 54 | 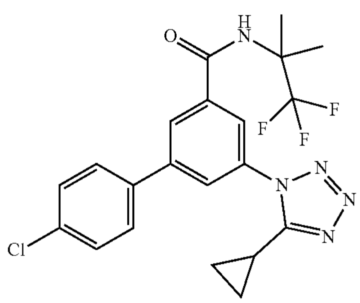 [SMILES: CC(C)(NC(=O)c1cc(-c2ccc(Cl)cc2)cc(-n2nnnc2C2CC2)c1)C(F)(F)F] | 3-(4-Chlorophenyl)-5-(5-cyclopropyltetrazol-1-yl)-N-(1,1,1-trifluoro-2-methylpropan-2-yl)-benzamide | 0.21 |
| 55 | 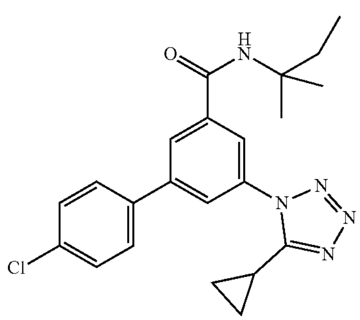 [SMILES: CCC(C)(C)NC(=O)c1cc(-c2ccc(Cl)cc2)cc(-n2nnnc2C2CC2)c1] | 3-(4-Chlorophenyl)-5-(5-cyclopropyltetrazol-1-yl)-N-(2-methylbutan-2-yl)-benzamide | 0.48 |
| 56 | 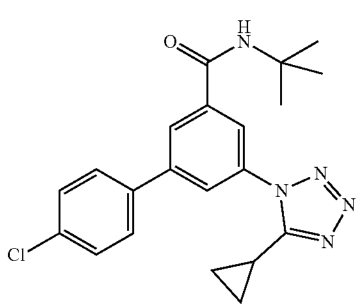 [SMILES: CC(C)(C)NC(=O)c1cc(-c2ccc(Cl)cc2)cc(-n2nnnc2C2CC2)c1] | N-tert-Butyl-3-(4-chlorophenyl)-5-(5-cyclopropyltetrazol-1-yl)-benzamide | 0.18 |

-continued

| | Structure | Name | EAAT3 Kb [uM] |
|---|---|---|---|
| 57 | 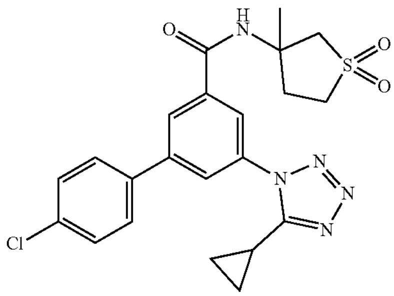 [SMILES: CC1(NC(=O)c2cc(-c3ccc(Cl)cc3)cc(-n3nnnc3C3CC3)c2)CCS(=O)(=O)C1] | (RS)-3-(4-Chlorophenyl)-5-(5-cyclopropyltetrazol-1-yl)-N-(3-methyl-1,1-dioxothiolan-3-yl)-benzamide | 0.35 |
| 58 | 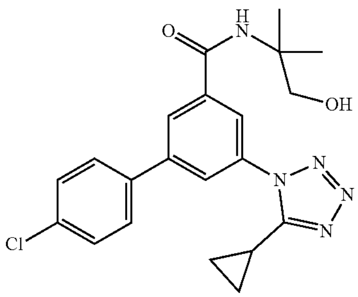 [SMILES: CC(C)(CO)NC(=O)c1cc(-c2ccc(Cl)cc2)cc(-n2nnnc2C2CC2)c1] | 3-(4-Chlorophenyl)-5-(5-cyclopropyltetrazol-1-yl)-N-(1-hydroxy-2-methylpropan-2-yl)-benzamide | 0.36 |
| 59 | 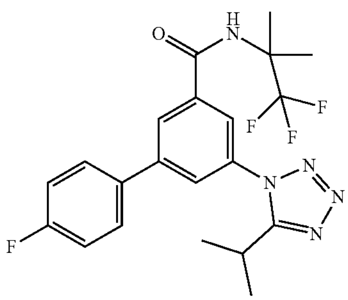 [SMILES: CC(C)c1nnnn1-c1cc(C(=O)NC(C)(C)C(F)(F)F)cc(-c2ccc(F)cc2)c1] | 3-(4-Fluorophenyl)-5-(5-propan-2-yltetrazol-1-yl)-N-(1,1,1-trifluoro-2-methylpropan-2-yl)-benzamide | 0.31 |
| 60 | 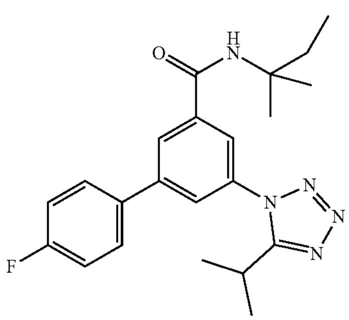 [SMILES: CCC(C)(C)NC(=O)c1cc(-c2ccc(F)cc2)cc(-n2nnnc2C(C)C)c1] | 3-(4-Fluorophenyl)-N-(2-methylbutan-2-yl)-5-(5-propan-2-yltetrazol-1-yl)-benzamide | 0.21 |
| 61 | 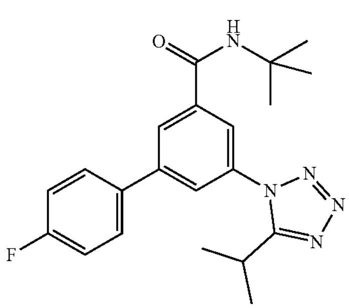 [SMILES: CC(C)c1nnnn1-c1cc(C(=O)NC(C)(C)C)cc(-c2ccc(F)cc2)c1] | N-tert-Butyl-3-(4-fluorophenyl)-5-(5-propan-2-yltetrazol-1-yl)-benzamide | 0.23 |

| | Structure | Name | EAAT3 Kb [uM] |
|---|---|---|---|
| 62 | 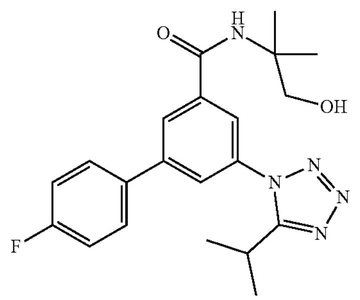 [SMILES: CC(C)c1nnnn1-c1cc(C(=O)NC(C)(C)CO)cc(-c2ccc(F)cc2)c1] | 3-(4-Fluorophenyl)-N-(1-hydroxy-2-methylpropan-2-yl)-5-(5-propan-2-yltetrazol-1-yl)-benzamide | 0.55 |
| 63 | 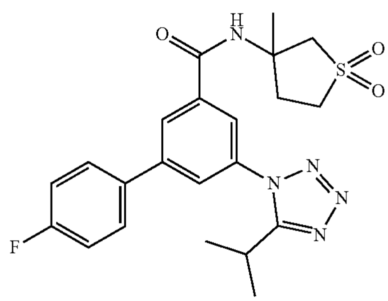 [SMILES: CC(C)c1nnnn1-c1cc(C(=O)NC2(C)CCS(=O)(=O)C2)cc(-c2ccc(F)cc2)c1] | (RS)-3-(4-Fluorophenyl)-N-(3-methyl-1,1-dioxothiolan-3-yl)-5-(5-propan-2-yltetrazol-1-yl)-benzamide | 0.65 |
| 64 | 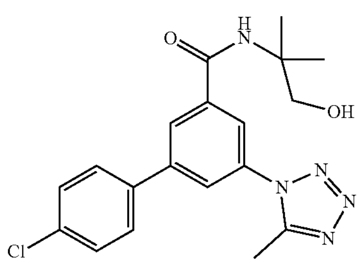 [SMILES: Cc1nnnn1-c1cc(C(=O)NC(C)(C)CO)cc(-c2ccc(Cl)cc2)c1] | 3-(4-Chlorophenyl)-N-(1-hydroxy-2-methylpropan-2-yl)-5-(5-methyl-tetrazol-1-yl)-benzamide | 0.42 |
| 65 | 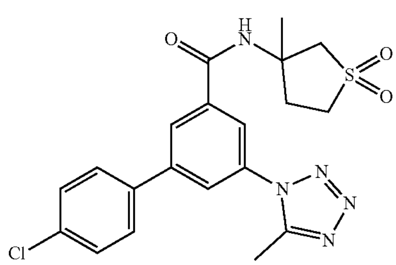 [SMILES: Cc1nnnn1-c1cc(C(=O)NC2(C)CCS(=O)(=O)C2)cc(-c2ccc(Cl)cc2)c1] | (RS)-3-(4-Chlorophenyl)-N-(3-methyl-1,1-dioxothiolan-3-yl)-5-(5-methyltetrazol-1-yl)-benzamide | 0.36 |
| 66 | 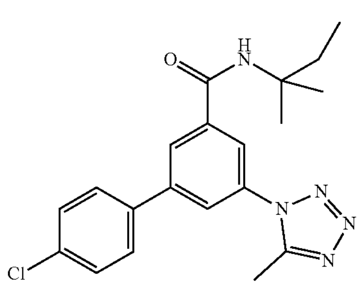 [SMILES: CCC(C)(C)NC(=O)c1cc(-c2ccc(Cl)cc2)cc(-n2nnnc2C)c1] | 3-(4-Chlorophenyl)-N-(2-methylbutan-2-yl)-5-(5-methyltetrazol-1-yl)-benzamide | 0.17 |

-continued

| | Structure | Name | EAAT3 Kb [uM] |
|---|---|---|---|
| 67 | 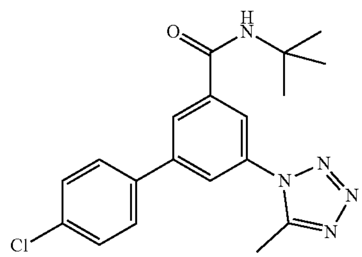 [SMILES: Cc1nnnn1-c1cc(C(=O)NC(C)(C)C)cc(-c2ccc(Cl)cc2)c1] | N-tert-Butyl-3-(4-chlorophenyl)-5-(5-methyltetrazol-1-yl)-benzamide | 0.24 |
| 68 | 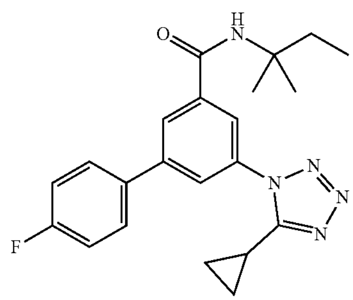 [SMILES: CCC(C)(C)NC(=O)c1cc(-c2ccc(F)cc2)cc(-n2nnnc2C2CC2)c1] | 3-(5-Cyclopropyltetrazol-1-yl)-5-(4-fluorophenyl)-N-(2-methylbutan-2-yl)-benzamide | 0.18 |
| 69 | 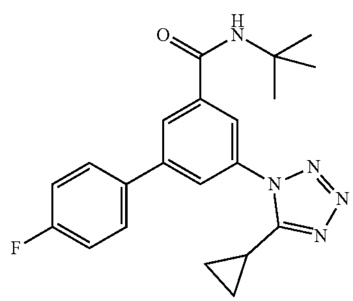 [SMILES: CC(C)(C)NC(=O)c1cc(-c2ccc(F)cc2)cc(-n2nnnc2C2CC2)c1] | N-tert-Butyl-3-(5-cyclopropyltetrazol-1-yl)-5-(4-fluorophenyl)-benzamide | 0.15 |
| 70 | 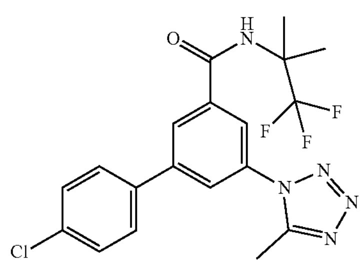 [SMILES: Cc1nnnn1-c1cc(C(=O)NC(C)(C)C(F)(F)F)cc(-c2ccc(Cl)cc2)c1] | 3-(4-Chlorophenyl)-5-(5-methyltetrazol-1-yl)-N-(1,1,1-trifluoro-2-methylpropan-2-yl)-benzamide | 0.23 |
| 71 | 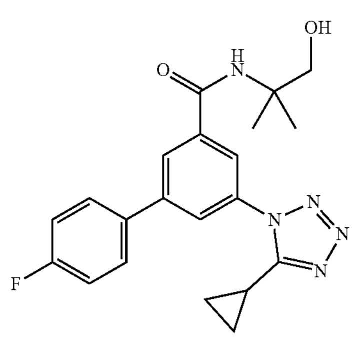 [SMILES: CC(C)(CO)NC(=O)c1cc(-c2ccc(F)cc2)cc(-n2nnnc2C2CC2)c1] | 3-(5-Cyclopropyltetrazol-1-yl)-5-(4-fluorophenyl)-N-(1-hydroxy-2-methylpropan-2-yl)-benzamide | 0.41 |

| | Structure | Name | EAAT3 Kb [uM] |
|---|---|---|---|
| 72 | 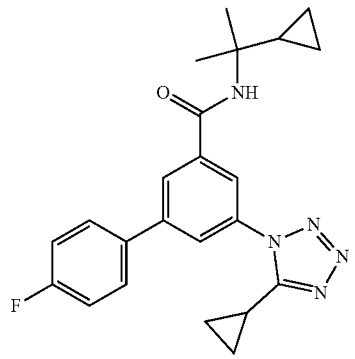 [SMILES: CC(C)(NC(=O)c1cc(-c2ccc(F)cc2)cc(-n2nnnc2C2CC2)c1)C1CC1] | N-(2-Cyclopropylpropan-2-yl)-3-(5-cyclopropyltetrazol-1-yl)-5-(4-fluorophenyl)-benzamide | 0.38 |
| 73 | 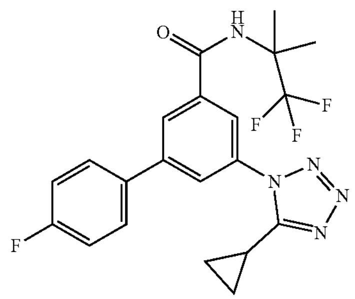 [SMILES: CC(C)(NC(=O)c1cc(-c2ccc(F)cc2)cc(-n2nnnc2C2CC2)c1)C(F)(F)F] | 3-(5-Cyclopropyltetrazol-1-yl)-5-(4-fluorophenyl)-N-(1,1,1-trifluoro-2-methylpropan-2-yl)-benzamide | 0.11 |
| 74 | 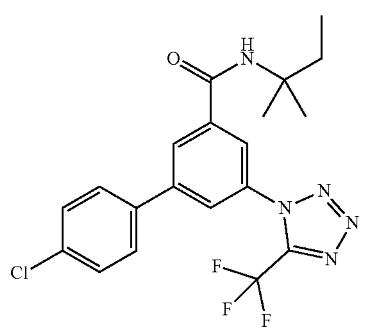 [SMILES: CCC(C)(C)NC(=O)c1cc(-c2ccc(Cl)cc2)cc(-n2nnnc2C(F)(F)F)c1] | 3-(4-Chlorophenyl)-N-(2-methylbutan-2-yl)-5-[5-(trifluoromethyl)-tetrazol-1-yl]-benzamide | 0.18 |
| 75 | 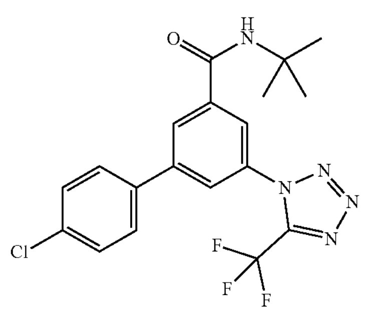 [SMILES: CC(C)(C)NC(=O)c1cc(-c2ccc(Cl)cc2)cc(-n2nnnc2C(F)(F)F)c1] | N-tert-Butyl-3-(4-chlorophenyl)-5-[5-(trifluoromethyl)-tetrazol-1-yl]-benzamide | 0.11 |

-continued

| | Structure | Name | EAAT3 Kb [uM] |
|---|---|---|---|
| 76 | 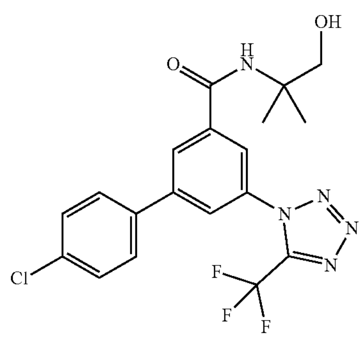 [SMILES: CC(C)(CO)NC(=O)c1cc(-c2ccc(Cl)cc2)cc(-n2nnnc2C(F)(F)F)c1] | 3-(4-Chlorophenyl)-N-(1-hydroxy-2-methylpropan-2-yl)-5-[5-(trifluoromethyl)-tetrazol-1-yl]-benzamide | 0.3 |
| 77 | 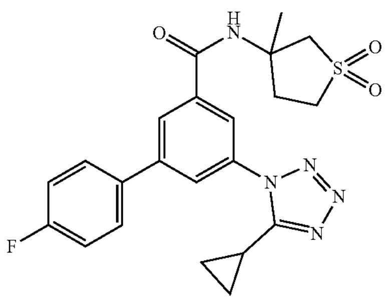 [SMILES: CC1(NC(=O)c2cc(-c3ccc(F)cc3)cc(-n3nnnc3C3CC3)c2)CCS(=O)(=O)C1] | (RS)-3-(5-Cyclopropyltetrazol-1-yl)-5-(4-fluorophenyl)-N-(3-methyl-1,1-dioxothiolan-3-yl)-benzamide | 0.25 |
| 78 | 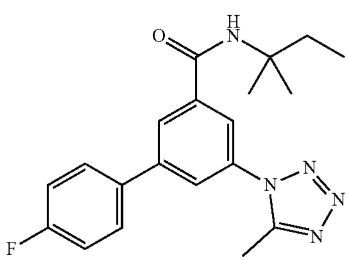 [SMILES: CCC(C)(C)NC(=O)c1cc(-c2ccc(F)cc2)cc(-n2nnnc2C)c1] | 3-(4-Fluorophenyl)-N-(2-methylbutan-2-yl)-5-(5-methyltetrazol-1-yl)-benzamide | 0.11 |
| 79 | 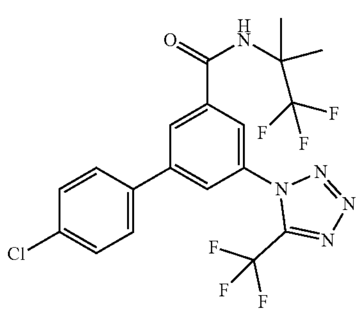 [SMILES: CC(C)(NC(=O)c1cc(-c2ccc(Cl)cc2)cc(-n2nnnc2C(F)(F)F)c1)C(F)(F)F] | 3-(4-Chlorophenyl)-N-(1,1,1-trifluoro-2-methylpropan-2-yl)-5-[5-(trifluoromethyl)tetrazol-1-yl]-benzamide | 0.2 |
| 80 | 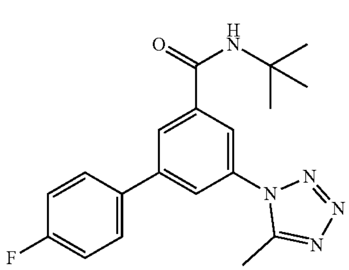 [SMILES: Cc1nnnn1-c1cc(C(=O)NC(C)(C)C)cc(-c2ccc(F)cc2)c1] | N-tert-Butyl-3-(4-fluorophenyl)-5-(5-methyltetrazol-1-yl)-benzamide | 0.18 |

-continued

| | Structure | Name | EAAT3 Kb [uM] |
|---|---|---|---|
| 81 | 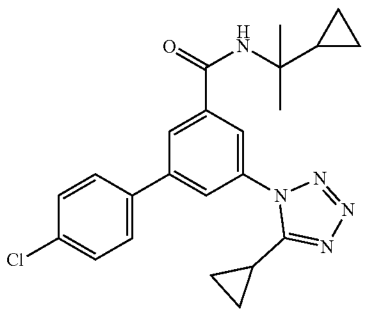 [SMILES: CC(C)(NC(=O)c1cc(-c2ccc(Cl)cc2)cc(-n2nnnc2C2CC2)c1)C1CC1] | 3-(4-Chlorophenyl)-N-(2-cyclopropylpropan-2-yl)-5-(5-cyclopropyl-tetrazol-1-yl)-benzamide | 0.21 |
| 82 | 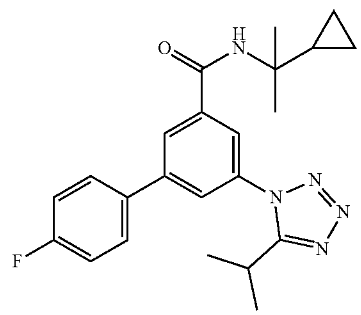 [SMILES: CC(C)c1nnnn1-c1cc(C(=O)NC(C)(C)C2CC2)cc(-c2ccc(F)cc2)c1] | N-(2-Cyclopropylpropan-2-yl)-3-(4-fluorophenyl)-5-(5-propan-2-yltetrazol-1-yl)-benzamide | 0.16 |
| 83 | 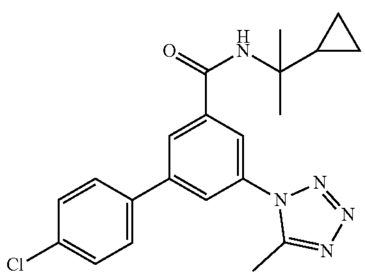 [SMILES: Cc1nnnn1-c1cc(C(=O)NC(C)(C)C2CC2)cc(-c2ccc(Cl)cc2)c1] | 3-(4-Chlorophenyl)-N-(2-cyclopropylpropan-2-yl)-5-(5-methyltetrazol-1-yl)-benzamide | 0.18 |
| 84 | 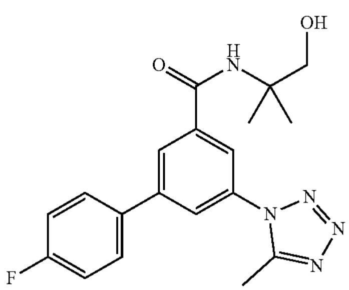 [SMILES: Cc1nnnn1-c1cc(C(=O)NC(C)(C)CO)cc(-c2ccc(F)cc2)c1] | 3-(4-Fluorophenyl)-N-(1-hydroxy-2-methylpropan-2-yl)-5-(5-methyltetrazol-1-yl)-benzamide | 0.78 |
| 85 | 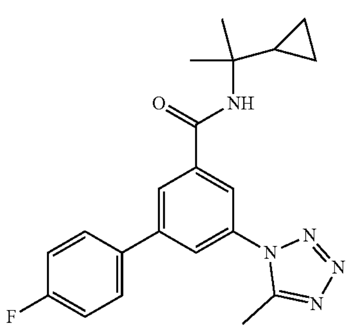 [SMILES: Cc1nnnn1-c1cc(C(=O)NC(C)(C)C2CC2)cc(-c2ccc(F)cc2)c1] | N-(2-Cyclopropylpropan-2-yl)-3-(4-fluorophenyl)-5-(5-methyltetrazol-1-yl)-benzamide | 0.29 |

| | Structure | Name | EAAT3 Kb [uM] |
|---|---|---|---|
| 86 | 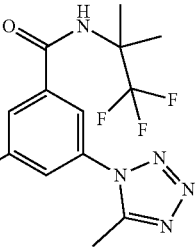 | 3-(4-Fluorophenyl)-5-(5-methyltetrazol-1-yl)-N-(1,1,1-trifluoro-2-methylpropan-2-yl)-benzamide | 0.2 |
| 87 | 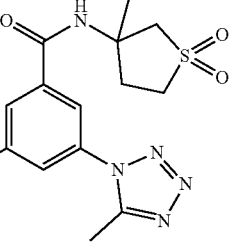 | (RS)-3-(4-Fluorophenyl)-N-(3-methyl-1,1-dioxothiolan-3-yl)-5-(5-methyltetrazol-1-yl)-benzamide | 0.29 |
| 88 | 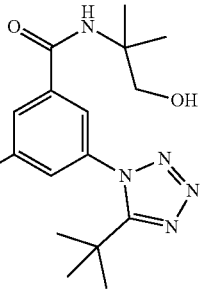 | 3-(5-tert-Butyltetrazol-1-yl)-5-(4-chlorophenyl)-N-(1-hydroxy-2-methylpropan-2-yl)-benzamide | 0.15 |
| 89 | 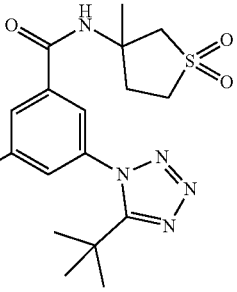 | (RS)-3-(5-tert-Butyltetrazol-1-yl)-5-(4-chlorophenyl)-N-(3-methyl-1,1-dioxothiolan-3-yl)benzamide | 0.25 |
| 90 | 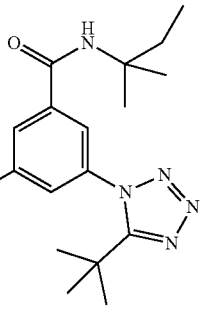 | 3-(5-tert-Butyltetrazol-1-yl)-5-(4-chlorophenyl)-N-(2-methylbutan-2-yl)-benzamide | 0.17 |

-continued

| | Structure | Name | EAAT3 Kb [uM] |
|---|---|---|---|
| 91 | 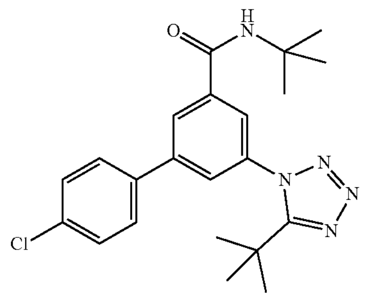 [SMILES: CC(C)(C)NC(=O)c1cc(-c2ccc(Cl)cc2)cc(-n2nnnc2C(C)(C)C)c1] | N-tert-Butyl-3-(5-tert-butyltetrazol-1-yl)-5-(4-chlorophenyl)-benzamide | 0.087 |
| 92 | 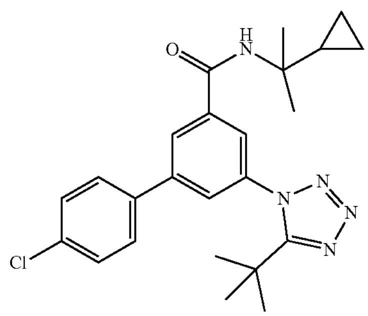 [SMILES: CC(C)(C)c1nnnn1-c1cc(C(=O)NC(C)(C)C2CC2)cc(-c2ccc(Cl)cc2)c1] | 3-(5-tert-Butyltetrazol-1-yl)-5-(4-chlorophenyl)-N-(2-cyclopropylpropan-2-yl)-benzamide | 0.3 |
| 93 | 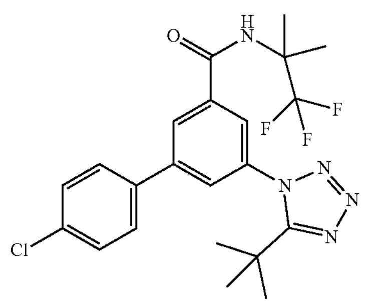 [SMILES: CC(C)(C)c1nnnn1-c1cc(C(=O)NC(C)(C)C(F)(F)F)cc(-c2ccc(Cl)cc2)c1] | 3-(5-tert-Butyltetrazol-1-yl)-5-(4-chlorophenyl)-N-(1,1,1-trifluoro-2-methylpropan-2-yl)-benzamide | 0.26 |
| 94 | 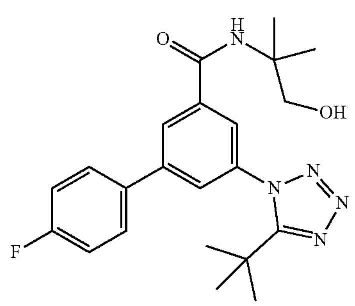 [SMILES: CC(C)(CO)NC(=O)c1cc(-c2ccc(F)cc2)cc(-n2nnnc2C(C)(C)C)c1] | 3-(5-tert-Butyltetrazol-1-yl)-5-(4-fluorophenyl)-N-(1-hydroxy-2-methylpropan-2-yl)-benzamide | 0.25 |
| 95 | 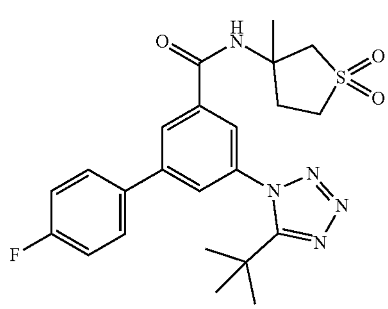 [SMILES: CC1(NC(=O)c2cc(-c3ccc(F)cc3)cc(-n3nnnc3C(C)(C)C)c2)CCS(=O)(=O)C1] | (RS)-3-(5-tert-Butyltetrazol-1-yl)-5-(4-fluorophenyl)-N-(3-methyl-1,1-dioxothiolan-3-yl)-benzamide | 0.35 |

| | Structure | Name | EAAT3 Kb [uM] |
|---|---|---|---|
| 96 | 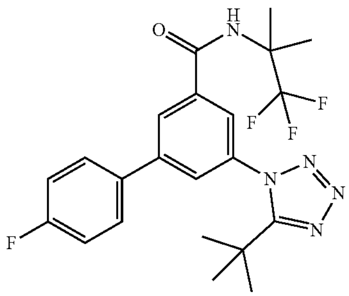 [SMILES: CC(C)(C)c1nnnn1-c1cc(C(=O)NC(C)(C)C(F)(F)F)cc(-c2ccc(F)cc2)c1] | 3-(5-tert-Butyltetrazol-1-yl)-5-(4-fluorophenyl)-N-(1,1,1-trifluoro-2-methylpropan-2-yl)-benzamide | 0.26 |
| 97 | 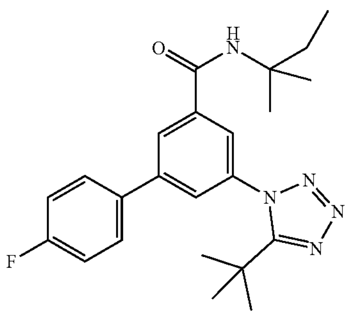 [SMILES: CCC(C)(C)NC(=O)c1cc(-c2ccc(F)cc2)cc(-n2nnnc2C(C)(C)C)c1] | 3-(5-tert-Butyltetrazol-1-yl)-5-(4-fluorophenyl)-N-(2-methylbutan-2-yl)-benzamide | 0.12 |
| 98 | 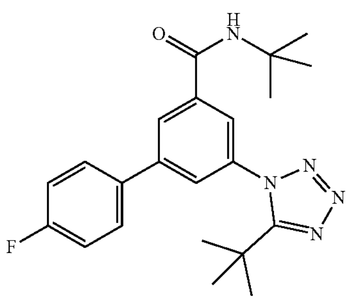 [SMILES: CC(C)(C)NC(=O)c1cc(-c2ccc(F)cc2)cc(-n2nnnc2C(C)(C)C)c1] | N-tert-Butyl-3-(5-tert-butyltetrazol-1-yl)-5-(4-fluorophenyl)-benzamide | 0.1 |
| 99 | 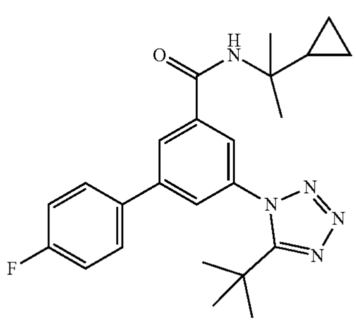 [SMILES: CC(C)(C)c1nnnn1-c1cc(C(=O)NC(C)(C)C2CC2)cc(-c2ccc(F)cc2)c1] | 3-(5-tert-Butyltetrazol-1-yl)-N-(2-cyclopropylpropan-2-yl)-5-(4-fluorophenyl)-benzamide | 0.2 |
| 100 | 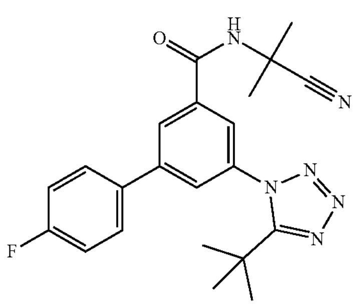 [SMILES: CC(C)(C#N)NC(=O)c1cc(-c2ccc(F)cc2)cc(-n2nnnc2C(C)(C)C)c1] | 3-(5-tert-Butyltetrazol-1-yl)-N-(2-cyanopropan-2-yl)-5-(4-fluorophenyl)-benzamide | 0.23 |

-continued

| | Structure | Name | EAAT3 Kb [uM] |
|---|---|---|---|
| 101 | 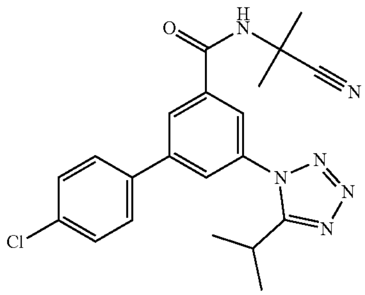 [SMILES: CC(C)c1nnnn1-c1cc(C(=O)NC(C)(C)C#N)cc(-c2ccc(Cl)cc2)c1] | 3-(4-Chlorophenyl)-N-(2-cyanopropan-2-yl)-5-(5-propan-2-yltetrazol-1-yl)-benzamide | 0.205 |
| 102 | 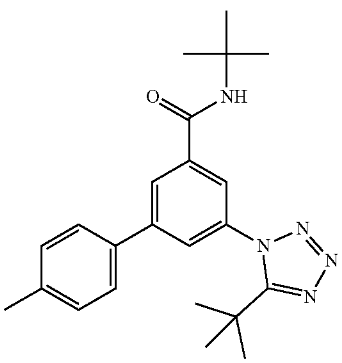 [SMILES: Cc1ccc(-c2cc(C(=O)NC(C)(C)C)cc(-n3nnnc3C(C)(C)C)c2)cc1] | N-tert-Butyl-3-(5-tert-butyltetrazol-1-yl)-5-(4-methylphenyl)-benzamide | 0.12 |
| 103 | 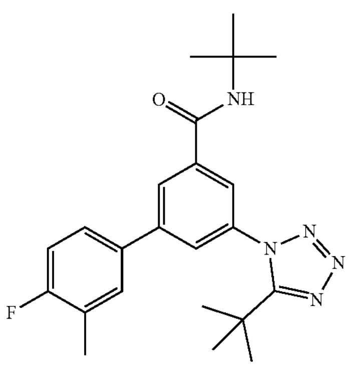 [SMILES: Cc1cc(-c2cc(C(=O)NC(C)(C)C)cc(-n3nnnc3C(C)(C)C)c2)ccc1F] | N-tert-Butyl-3-(5-tert-butyltetrazol-1-yl)-5-(4-fluoro-3-methylphenyl)-benzamide | 0.26 |
| 104 | 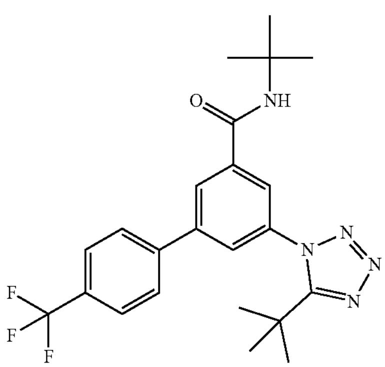 [SMILES: CC(C)(C)NC(=O)c1cc(-c2ccc(C(F)(F)F)cc2)cc(-n2nnnc2C(C)(C)C)c1] | N-tert-Butyl-3-(5-tert-butyltetrazol-1-yl)-5-[4-(trifluoromethyl)-phenyl]-benzamide | 0.19 |

-continued
| | Structure | Name | EAAT3 Kb [uM] |
|---|---|---|---|
| 105 | 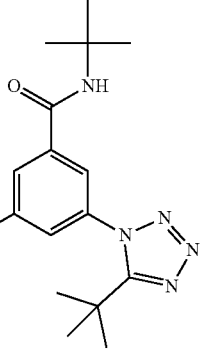 | N-tert-Butyl-3-(5-tert-butyltetrazol-1-yl)-5-(4-chloro-3-fluorophenyl)-benzamide | 0.29 |
| 106 | 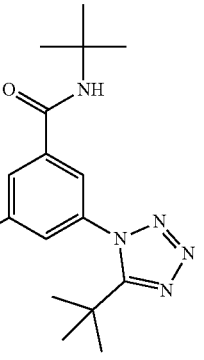 | N-tert-Butyl-3-(5-tert-butyltetrazol-1-yl)-5-(3,4-difluorophenyl)-benzamide | 0.26 |
| 107 | 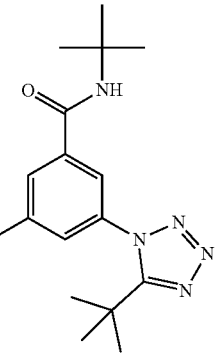 | N-tert-Butyl-3-(5-tert-butyltetrazol-1-yl)-5-(4-cyclopropylphenyl)-benzamide | 0.28 |
| 108 | 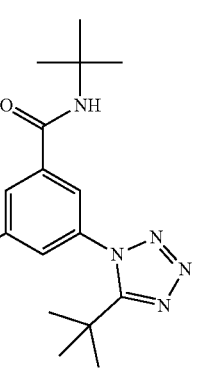 | N-tert-Butyl-3-(5-tert-butyltetrazol-1-yl)-5-(3-fluoro-4-methylphenyl)-benzamide | 0.42 |

| | Structure | Name | EAAT3 Kb [uM] |
|---|---|---|---|
| 109 | 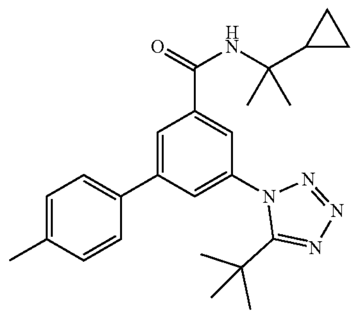 [SMILES: Cc1ccc(-c2cc(C(=O)NC(C)(C)C3CC3)cc(-n3nnnc3C(C)(C)C)c2)cc1] | 3-(5-tert-Butyltetrazol-1-yl)-N-(2-cyclopropylpropan-2-yl)-5-(4-methylphenyl)-benzamide | 0.37 |
| 110 | 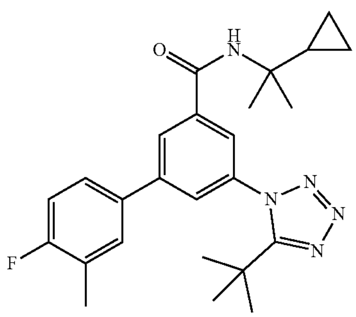 [SMILES: Cc1cc(-c2cc(C(=O)NC(C)(C)C3CC3)cc(-n3nnnc3C(C)(C)C)c2)ccc1F] | 3-(5-tert-Butyltetrazol-1-yl)-N-(2-cyclopropylpropan-2-yl)-5-(4-fluoro-3-methylphenyl)-benzamide | 0.49 |
| 111 | 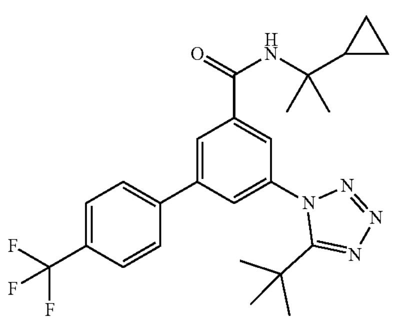 [SMILES: CC(C)(C)c1nnnn1-c1cc(C(=O)NC(C)(C)C2CC2)cc(-c2ccc(C(F)(F)F)cc2)c1] | 3-(5-tert-Butyltetrazol-1-yl)-N-(2-cyclopropylpropan-2-yl)-5-[4-(trifluoromethyl)-phenyl]-benzamide | 0.5 |
| 112 | 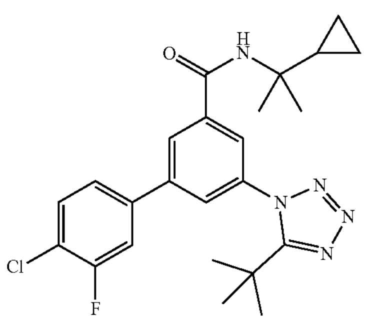 [SMILES: CC(C)(C)c1nnnn1-c1cc(C(=O)NC(C)(C)C2CC2)cc(-c2ccc(Cl)c(F)c2)c1] | 3-(5-tert-Butyltetrazol-1-yl)-5-(4-chloro-3-fluorophenyl)-N-(2-cyclopropylpropan-2-yl)-benzamide | 0.53 |

-continued
| | Structure | Name | EAAT3 Kb [uM] |
|---|---|---|---|
| 113 | 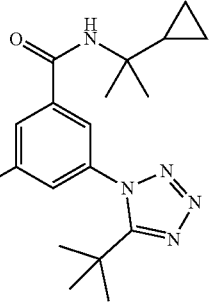 | 3-(5-tert-Butyltetrazol-1-yl)-N-(2-cyclopropylpropan-2-yl)-5-(3,4-difluorophenyl)-benzamide | 0.35 |
| 114 | 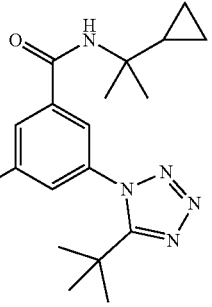 | 3-(5-tert-Butyltetrazol-1-yl)-5-(4-cyclopropylphenyl)-N-(2-cyclopropylpropan-2-yl)-benzamide | 0.62 |
| 115 | 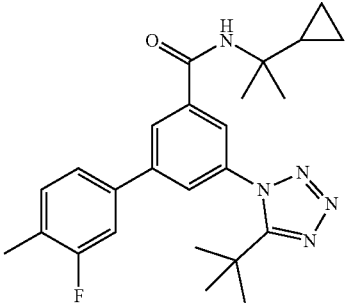 [SMILES: Cc1ccc(-c2cc(C(=O)NC(C)(C)C3CC3)cc(-n3nnnc3C(C)(C)C)c2)cc1F] | 3-(5-tert-Butyltetrazol-1-yl)-N-(2-cyclopropylpropan-2-yl)-5-(3-fluoro-4-methylphenyl)-benzamide | 0.52 |
| 116 | 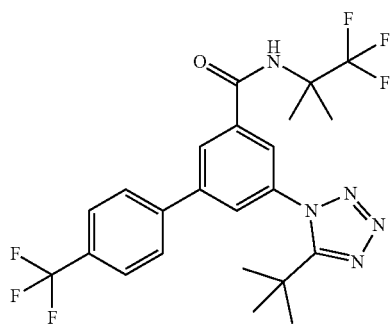 [SMILES: CC(C)(C)c1nnnn1-c1cc(C(=O)NC(C)(C)C(F)(F)F)cc(-c2ccc(C(F)(F)F)cc2)c1] | 3-(5-tert-Butyltetrazol-1-yl)-5-[4-(trifluoromethyl)-phenyl]-N-(1,1,1-trifluoro-2-methylpropan-2-yl)-benzamide | 0.55 |

-continued

| | Structure | Name | EAAT3 Kb [uM] |
|---|---|---|---|
| 117 | 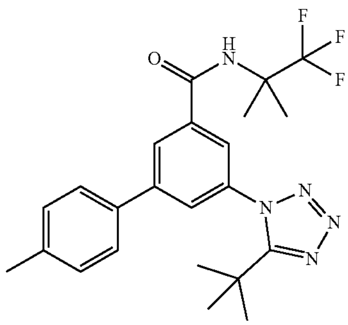 [SMILES: Cc1ccc(-c2cc(C(=O)NC(C)(C)C(F)(F)F)cc(-n3nnnc3C(C)(C)C)c2)cc1] | 3-(5-tert-Butyltetrazol-1-yl)-5-(4-methylphenyl)-N-(1,1,1-trifluoro-2-methylpropan-2-yl)-benzamide | 0.28 |
| 118 | 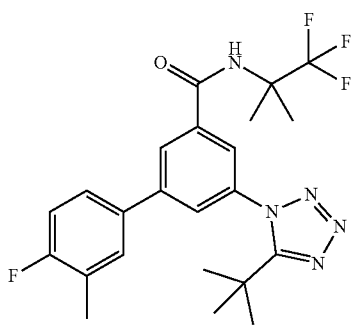 [SMILES: Cc1cc(-c2cc(C(=O)NC(C)(C)C(F)(F)F)cc(-n3nnnc3C(C)(C)C)c2)ccc1F] | 3-(5-tert-Butyltetrazol-1-yl)-5-(4-fluoro-3-methylphenyl)-N-(1,1,1-trifluoro-2-methylpropan-2-yl)-benzamide | 0.54 |
| 119 | 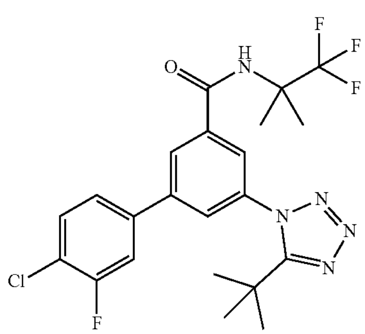 [SMILES: CC(C)(C)c1nnnn1-c1cc(C(=O)NC(C)(C)C(F)(F)F)cc(-c2ccc(Cl)c(F)c2)c1] | 3-(5-tert-Butyltetrazol-1-yl)-5-(4-chloro-3-fluorophenyl)-N-(1,1,1-trifluoro-2-methylpropan-2-yl)-benzamide | 0.35 |
| 120 | 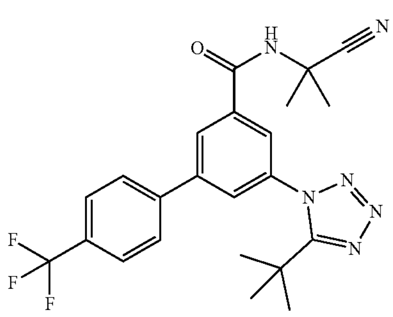 [SMILES: CC(C)(C#N)NC(=O)c1cc(-c2ccc(C(F)(F)F)cc2)cc(-n2nnnc2C(C)(C)C)c1] | 3-(5-tert-Butyltetrazol-1-yl)-N-(2-cyanopropan-2-yl)-5-[4-(trifluoromethyl)-phenyl]benzamide | 0.3 |

| | Structure | Name | EAAT3 Kb [uM] |
|---|---|---|---|
| 121 | 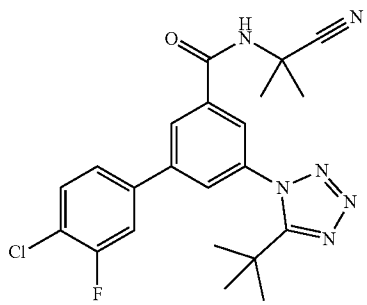 [SMILES: CC(C)(C#N)NC(=O)c1cc(-c2ccc(Cl)c(F)c2)cc(-n2nnnc2C(C)(C)C)c1] | 3-(5-tert-Butyltetrazol-1-yl)-5-(4-chloro-3-fluorophenyl)-N-(2-cyanopropan-2-yl)-benzamide | 0.21 |
| 122 | 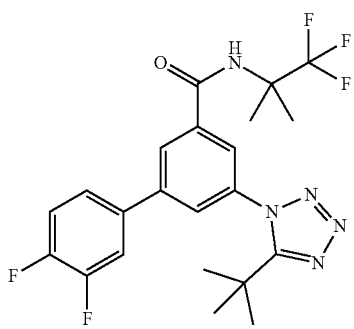 [SMILES: CC(C)(C)c1nnnn1-c1cc(C(=O)NC(C)(C)C(F)(F)F)cc(-c2ccc(F)c(F)c2)c1] | 3-(5-tert-Butyltetrazol-1-yl)-5-(3,4-difluorophenyl)-N-(1,1,1-trifluoro-2-methylpropan-2-yl)-benzamide | 0.36 |
| 123 | 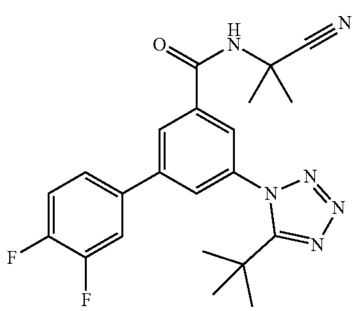 [SMILES: CC(C)(C#N)NC(=O)c1cc(-c2ccc(F)c(F)c2)cc(-n2nnnc2C(C)(C)C)c1] | 3-(5-tert-Butyltetrazol-1-yl)-N-(2-cyanopropan-2-yl)-5-(3,4-difluorophenyl)-benzamide | 0.22 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention Tablets of the following composition are manufactured in the usual manner:

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXPERIMENTAL SECTION

Intermediates

Intermediate 1: 3-(4-Fluorophenyl)-5-(tetrazol-1-yl)-benzoic acid

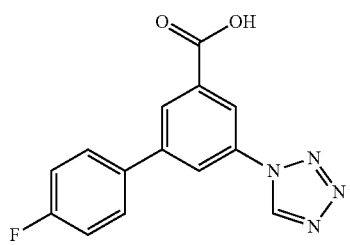 [SMILES: O=C(O)c1cc(-c2ccc(F)cc2)cc(-n2cnnn2)c1]

Step A

To a stirred solution of commercially available 3-iodo-5-nitrobenzoic acid (3.67 g, 12.5 mmol) and Pd(Ph$_3$P)$_4$ (463 mg, 401 µmol) in toluene (71.3 ml) and ethanol (11.9 ml) was added at room temperature commercially available 4-fluoro-phenylboronic acid (1.93 g, 13.8 mmol) and a solution of Cs$_2$CO$_3$ (4.49 g, 13.8 mmol) in water (4.78 ml). The reaction mixture was stirred under reflux conditions for 18 h and then cooled to room temperature. To the mixture was added 2N NaOH (52 ml), and the reaction mixture was stirred for 30 min at room temperature. Some precipitated material was collected by filtration. The organic layer was separated, and to the water layer together with the precipitated material was added conc. hydrochloric acid (19 ml) to reach pH<4. The mixture was extracted with ethyl acetate (2×75 ml), the combined organic layers were washed with brine, dried (MgSO$_4$) and evaporated to yield crude 3-(4-fluorophenyl)-5-nitrobenzoic acid (3.73 g) as brown solid, MS (ISN) m/z=260.1 [(M–H)$^+$], which was subsequently dissolved in methanol (35.1 ml). To the stirred solution was added dropwise thionyl chloride (1.87 g, 1.14 ml, 15.7 mmol) at 0° C. The reaction mixture was allowed to warm to room temperature, and was afterwards stirred under reflux conditions for 2 h. The solvent was removed in vacuo to yield crude methyl 3-(4-fluorophenyl)-5-nitrobenzoate (3.65 g) as a light brown solid, MS (ISP) m/z=279.1 [(M+H)$^+$], which was subsequently dissolved in methanol (35.1 ml). To the stirred solution was added at room temperature tin(II) chloride (10.0 g, 52.9 mmol), the reaction mixture was stirred under reflux conditions for 3 h, evaporated, the residue was dissolved in water (200 ml) and basified to pH=9 by addition of Na$_2$CO$_3$. The mixture was extracted with dichloro-methane (3×75 ml), the combined organic layers were washed with water (150 ml), brine (150 ml), dried (MgSO$_4$) and evaporated to yield methyl 3-amino-5-(4-fluorophenyl)-benzoate (3.0 g, 98%) as a light yellow solid, MS (ISP) m/z=246.1 [(M+H)$^+$], mp 124° C.

Step B

To a stirred solution of methyl 3-amino-5-(4-fluorophenyl)-benzoate (2.99 g, 12.2 mmol) and sodium azide (1.47 g, 22.6 mmol) in AcOH (23.6 ml) was added at room temperature triethyl orthoformate (8.67 g, 9.74 ml, 58.5 mmol). The reaction mixture was stirred under reflux conditions for 2.5 h, poured into ice/water (100 ml) and extracted with dichloromethane (2×75 ml). The combined organic layers were washed with brine (75 ml), dried (MgSO$_4$) and evaporated. The crude product (3.93 g) was purified by flash chromatography on silica gel [heptane/ethyl acetate (20-100%)] and trituration in diethyl ether (10 ml) to yield methyl 3-(4-fluorophenyl)-5-(tetrazol-1-yl)-benzoate (3.17 g, 87%) as an off-white solid, MS (ISP) m/z=299.1 [(M+H)$^+$], mp 175° C.

Step C

A solution of lithium hydroxide monohydrate (578 mg, 13.8 mmol) in water (12.5 ml) was added dropwise to a stirred and cooled (0° C.) suspension of methyl 3-(4-fluorophenyl)-5-(tetrazol-1-yl)-benzoate (3.16 g, 10.6 mmol) in THF (7.8 ml). The reaction mixture was stirred at room temperature for 15 h resulting in a clear solution, THF was evaporated, and the aqueous solution was acidified by addition of 25% hydrochloric acid (pH=3). The resulting precipitate was collected by filtration and dried to yield the title compound (2.84 g, 94%) as white solid, MS (ISP) m/z=285.1 [(M+H)$^+$], mp 240° C.

Intermediate 2: 3-(Tetrazol-1-yl)-5-[4-(trifluoromethyl)-phenyl]-benzoic acid

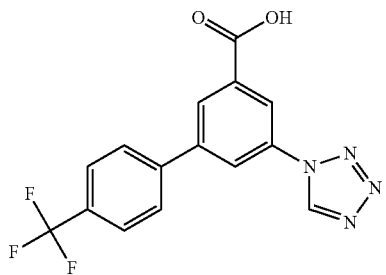 [SMILES: O=C(O)c1cc(-c2ccc(C(F)(F)F)cc2)cc(-n2cnnn2)c1]

Step A

Methyl 3-amino-5-[4-(trifluoromethyl)phenyl]-benzoate, orange solid (2.28 g, 63%), MS (ISP) m/z=296.1 [(M+H)$^+$], mp 117° C., was prepared in accordance with the general method of intermediate 1, step A, from commercially available 3-iodo-5-nitrobenzoic acid (3.6 g, 12.3 mmol) and commercially available 4-(trifluoromethyl)-phenylboronic acid (2.57 g, 13.5 mmol).

Step B

Methyl 3-(tetrazol-1-yl)-5-[4-(trifluoromethyl)-phenyl]-benzoate, off-white solid (1.11 g, 94%), MS (ISP) m/z=349.1 [(M+H)$^+$], mp 193° C., was prepared in accordance with the general method of intermediate 1, step B, from methyl 3-amino-5-[4-(trifluoromethyl)-phenyl]-benzoate (1.0 g, 3.39 mmol).

Step C

The title compound, off-white solid (1.02 g, 96%), MS (ISN) m/z=333.2 [(M−H)$^−$], mp 208° C., was prepared in accordance with the general method of intermediate 1, step C, from methyl 3-(tetrazol-1-yl)-5-[4-(trifluoromethyl)-phenyl]-benzoate (1.11 g, 3.19 mmol).

Intermediate 3: 3-Iodo-N-(2-methylbutan-2-yl)-5-(tetrazol-1-yl)-benzamide

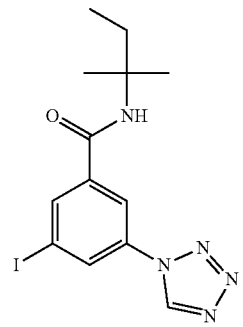 [SMILES: CCC(C)(C)NC(=O)c1cc(I)cc(-n2cnnn2)c1]

Step A

1-Ethyl-3-(3-dimethylaminopropyl)-carbodiimide (EDCI) (2.94 g, 15.4 mmol) was added in one portion to a stirred and cooled (0° C.) solution of commercially available 3-iodo-5-nitrobenzoic acid (3 g, 10.2 mmol), hydroxybenzotriazole (HOBT) (2.08 g, 15.4 mmol), 2-methylbutan-2-amine (911 mg, 1.22 ml, 10.2 mmol) and N-methyl-2-pyrrolidone (NMP) (1.53 g, 1.49 ml, 15.4 mmol) in dichloromethane (50 ml) and DMF (4.2 ml). The reaction mixture was allowed to stir for 15 h at room temperature, washed with 2N NaOH (30 ml), water (30 ml) and brine (30 ml), dried (MgSO$_4$) and evaporated. The crude product (4 g brown oil) was purified by flash chromatography on silica gel [heptane/ethyl acetate (10-60%)] to yield 3-iodo-N-(2-methylbutan-2-yl)-5-nitrobenzamide (2.38 g, 64%) as an off white solid, MS (ISP) m/z=363.1 [(M+H)$^+$], mp 117° C.

Step B

To a stirred solution of 3-iodo-N-(2-methylbutan-2-yl)-5-nitrobenzamide (2.38 g, 6.57 mmol) in methanol (50 ml) was added at room temperature tin(II)chloride (5.93 g, 26.3 mmol). The reaction mixture was stirred under reflux conditions for 3 hours, evaporated and the residue was dissolved in water (150 ml), basified (pH=9) by addition of Na$_2$CO$_3$, and extracted with dichloromethane (2×75 ml). The combined organic layers were washed with water (75 ml) and brine (75 ml), dried (MgSO$_4$) and evaporated to yield 3-amino-5-iodo-N-(2-methylbutan-2-yl)-benzamide (2.18 g, 100%) as a colorless oil, MS (ISP) m/z=333.2 [(M+H)$^+$].

Step C

The title compound, off-white foam (2.25 g, 89%), MS (ISP) m/z=386.2 [(M+H)$^+$], was prepared in accordance with the general method of intermediate 1, step B, from 3-amino-5-iodo-N-(2-methylbutan-2-yl)-benzamide (2.18 g, 6.56 mmol).

Intermediate 4: 3-(4-Methylphenyl)-5-(5-propan-2-yltetrazol-1-yl)-benzoic acid

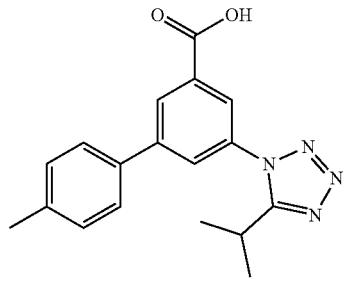 [SMILES: Cc1ccc(-c2cc(C(=O)O)cc(-n3nnnc3C(C)C)c2)cc1]

Step A

To a stirred solution of methyl 3-amino-5-(4-methylphenyl)-benzoate [CAS No. 1000587-31-4] (2.13 g, 8.83 mmol) and triethylamine (2.68 g, 3.69 ml, 26.5 mmol) in dichloromethane (46.4 ml) was added at room temperature isobutyryl chloride (1.15 g, 1.14 ml, 10.6 mmol), the reaction mixture was stirred for additional 2 h, water (50 ml) was added, and the solution was extracted with dichloromethane (2×50 ml). The combined organic layers were washed with brine (50 ml), dried (MgSO$_4$) and evaporated. The crude product (3.21 g) was purified by flash chromatography on silica gel [heptane/ethyl acetate (20-100%)] to yield methyl 3-(4-methylphenyl)-5-(2-methylpropanoylamino)-benzoate (2.66 g, 97%) as an off-white solid, MS (ISP) m/z=312.1 [(M+H)$^+$], mp 152° C.

Step B

To a stirred solution of methyl 3-(4-methylphenyl)-5-(2-methylpropanoylamino)-benzoate (2.65 g, 8.51 mmol) in acetonitrile (21 ml) sodium azide (553 mg, 8.51 mmol) and SiCl$_4$ (3.73 g, 2.52 ml, 21.3 mmol) were added at room temperature. The reaction mixture was stirred at 60° C. for 36 h. Since TLC showed that the reaction was not finished, sodium azide (277 mg, 4.26 mmol) and SiCl$_4$ (1.87 mg, 1.26 ml, 10.6 mmol) were added, and the reaction was stirred for additional 18 h at 60° C. The reaction mixture was poured into cold saturated NaHCO$_3$ solution (100 ml) and extracted with ethyl acetate (2×75 ml). The combined organic layers were washed with brine (75 ml), dried (MgSO$_4$) and evaporated. The crude product (2.64 g) was purified by flash chromatography on silica gel [dichloromethane/dichloromethane-MeOH 9:1 (0-25%)] and trituration from diethyl ether (3 ml) to yield methyl 3-(4-methylphenyl)-5-(5-propan-2-yltetrazol-1-yl)-benzoate (2.11 g, 74%) as a white solid, MS (ISP) m/z=337.2 [(M+H)$^+$], mp 157° C.

Step C

The title compound, white solid (1.95 g, 97%), MS (ISP) m/z=323.1 [(M+H)$^+$], mp 225° C., was prepared in accordance with the general method of intermediate 1, step C, from methyl 3-(4-methylphenyl)-5-(5-propan-2-yltetrazol-1-yl)-benzoate (2.1 g, 6.24 mmol).

Intermediate 5: 3-(5-Cyclopropyltetrazol-1-yl)-5-(4-methylphenyl)-benzoic acid

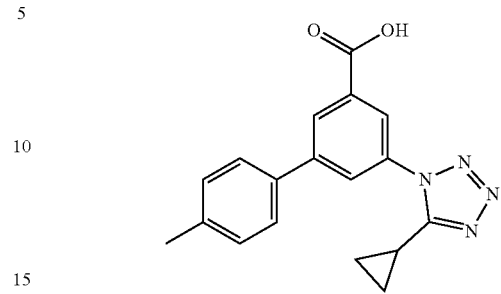

Step A

Methyl 5-(2-cyclopropanecarbonylamino)-3-(4-methylphenyl)-benzoate, off-white solid (2.31 g, 90%), MS (ISP) m/z=310.2 [(M+H)$^+$], was prepared in accordance with the general method of intermediate 4, step A, from 3-amino-5-(4-methylphenyl)-benzoate [CAS No. 1000587-31-4] (2.0 g, 8.29 mmol) and cyclopropanecarbonyl chloride (1.04 g, 9.95 mmol).

Step B

Methyl 3-(5-cyclopropyltetrazol-1-yl)-5-(4-methylphenyl)benzoate, light brown solid (2.43 g, 97%), MS (ISP) m/z=335.2 [(M+H)$^+$], was prepared in accordance with the general method of intermediate 4, step B, from methyl 5-(2-cyclopropane-carbonylamino)-3-(4-methyl-phenyl)-benzoate (2.31 g, 7.47 mmol).

Step C

The title compound, white solid (2.15 g, 93%), MS (ISP) m/z=321.2 [(M+H)$^+$], mp 183° C., was prepared in accordance with the general method of intermediate 1, step C, from methyl 3-(5-cyclopropyltetrazol-1-yl)-5-(4-methylphenyl)benzoate (2.42 g, 7.24 mmol).

Intermediate 6: 3-(5-Ethyltetrazol-1-yl)-5-(4-methylphenyl)benzoic acid

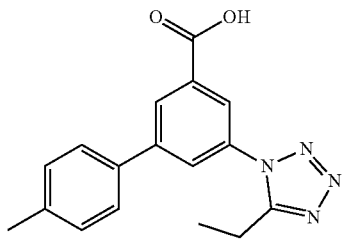 [SMILES: CCc1nnnn1-c1cc(C(=O)O)cc(-c2ccc(C)cc2)c1]

Step A

Methyl 3-(4-methylphenyl)-5-(propanoylamino)-benzoate, off-white solid (1.81 g, 82%), MS (ISP) m/z=298.2 [(M+H)$^+$], was prepared in accordance with the general method of intermediate 4, step A, from 3-amino-5-(4-methylphenyl)-benzoate [CAS No. 1000587-31-4] (1.79 g, 7.42 mmol) and propionyl chloride (824 mg, 721 µl, 8.9 mmol).

Step B

Methyl 3-(5-ethyltetrazol-1-yl)-5-(4-methylphenyl)benzoate, light yellow solid (1.86 g, 96%), MS (ISP) m/z=323.2 [(M+H)$^+$], mp 147.5° C., was prepared in accordance with the general method of intermediate 4, step B, from methyl 3-(4-methylphenyl)-5-(propanoylamino)-benzoate (1.79 g, 6.02 mmol).

Step C

The title compound, white solid (1.65 g, 93%), MS (ISP) m/z=309.2 [(M+H)$^+$], mp 195° C., was prepared in accordance with the general method of intermediate 1, step C, from methyl 3-(5-ethyltetrazol-1-yl)-5-(4-methylphenyl)-benzoate (1.86 g, 5.77 mmol).

Intermediate 7: 3-(4-Chlorophenyl)-5-(5-propan-2-yltetrazol-1-yl)benzoic acid

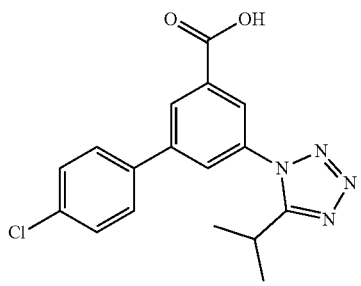 [SMILES: CC(C)c1nnnn1-c1cc(C(=O)O)cc(-c2ccc(Cl)cc2)c1]

Step A

Methyl 3-amino-5-(4-chlorophenyl)-benzoate, yellow solid (2.29 g, 71%), MS (ISP) m/z=262.1 [(M+H)$^+$], mp 120° C., was prepared in accordance with the general method of intermediate 1, step A, from commercially available 3-iodo-5-nitrobenzoic acid (3.6 g, 12.3 mmol) and commercially available 4-chloro-phenylboronic acid (2.11 g, 13.5 mmol).

Step B

Methyl 3-(4-chlorophenyl)-5-(2-methylpropanoylamino)-benzoate, light yellow oil (0.83 g, 91%), MS (ISP) m/z=332.1 [(M+H)$^+$], was prepared in accordance with the general method of intermediate 4, step A, from methyl 3-amino-5-(4-chlorophenyl)-benzoate (0.60 g, 2.29 mmol) and isobutyryl chloride (299 mg, 296 µl, 2.75 mmol).

Step C

Methyl 3-(4-chlorophenyl)-5-(5-propan-2-yltetrazol-1-yl)benzoate, light yellow solid (0.76 g, 94%), MS (ISP) m/z=357.1 [(M+H)$^+$], mp 167.5° C., was prepared in accordance with the general method of intermediate 4, step B, from methyl 3-(4-chlorophenyl)-5-(2-methylpropanoylamino)-benzoate (0.83 g, 2.28 mmol).

Step D

The title compound, white solid (0.68 g, 93%), MS (ISP) m/z=343.1 [(M+H)$^+$], mp 253° C., was prepared in accordance with the general method of intermediate 1, step C, from methyl 3-(4-chlorophenyl)-5-(5-propan-2-yltetrazol-1-yl)benzoate (0.76 g, 2.13 mmol).

Intermediate 8: 3-(5-Propan-2-yltetrazol-1-yl)-5-[4-(trifluoromethyl)-phenyl]-benzoic acid

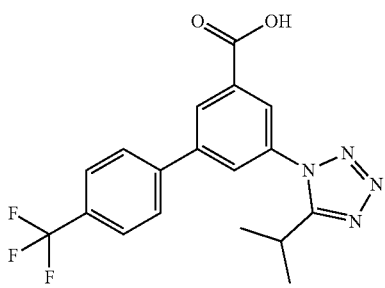 [SMILES: CC(C)c1nnnn1-c1cc(C(=O)O)cc(-c2ccc(C(F)(F)F)cc2)c1]

Step A

Methyl 3-(2-methylpropanoylamino)-5-[4-(trifluoromethyl)-phenyl]-benzoate, off-white solid (0.73 g, 98%), MS (ISP) m/z=366.1 [(M+H)$^+$], mp 165.5° C., was prepared in accordance with the general method of intermediate 4, step A, from methyl 3-amino-5-[4-(trifluoromethyl)-phenyl]-benzoate (intermediate 2, step A) (0.60 g, 2.03 mmol) and isobutyryl chloride (265 mg, 263 µl, 2.44 mmol).

Step B

Methyl 3-(5-propan-2-yltetrazol-1-yl)-5-[4-(trifluoromethyl)-phenyl]-benzoate, light yellow solid (0.73 g, 95%), MS (ISP) m/z=391.2 [(M+H)$^+$], mp 146° C., was prepared in accordance with the general method of intermediate 4, step B, from methyl 3-(2-methylpropanoylamino)-5-[4-(trifluoromethyl)-phenyl]-benzoate (0.72 g, 1.97 mmol).

Step C

The title compound, white solid (0.65 g, 92%), MS (ISP) m/z=377.1 [(M+H)$^+$], mp 251.5° C., was prepared in accordance with the general method of intermediate 1, step C, from methyl 3-(5-propan-2-yltetrazol-1-yl)-5-[4-(trifluoromethyl)-phenyl]-benzoate (0.73 g, 1.87 mmol).

Intermediate 9: 3-(4-Chlorophenyl)-5-(5-cyclopropyltetrazol-1-yl)-benzoic acid

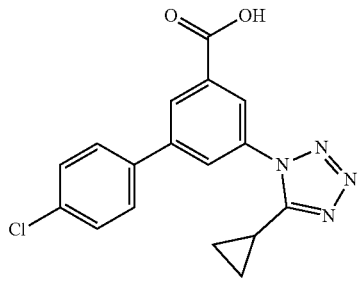 [SMILES: O=C(O)c1cc(-c2ccc(Cl)cc2)cc(-n2nnnc2C2CC2)c1]

Step A

Methyl 3-(4-chlorophenyl)-5-(cyclopropanecarbonylamino)-benzoate, white solid (0.83 g, 100%), MS (ISP) m/z=355.1 [(M+H)$^+$], mp 194.5° C., was prepared in accordance with the general method of intermediate 4, step A, from methyl 3-amino-5-(4-chlorophenyl)-benzoate (intermediate 8, step A) (0.66 g, 2.52 mmol) and cyclopropanecarbonyl chloride (323 mg, 283 µl, 3.03 mmol).

Step B

Methyl 3-(4-chlorophenyl)-5-(5-cyclopropyltetrazol-1-yl)-benzoate, white solid (0.79 g, 89%), MS (ISP) m/z=357.1 [(M+H)$^+$], mp 190.5° C., was prepared in accordance with the general method of intermediate 4, step B, from methyl 3-(4-chlorophenyl)-5-(cyclopropanecarbonylamino)-benzoate (0.83 g, 2.52 mmol).

Step C

The title compound, white solid (0.68 g, 90%), MS (ISP) m/z=341.1 [(M+H)$^+$], mp 230° C., was prepared in accordance with the general method of intermediate 1, step C, from methyl 3-(4-chlorophenyl)-5-(5-cyclopropyltetrazol-1-yl)-benzoate (0.79 g, 2.23 mmol).

Intermediate 10: 3-(4-Fluorophenyl)-5-(5-propan-2-yltetrazol-1-yl)-benzoic acid

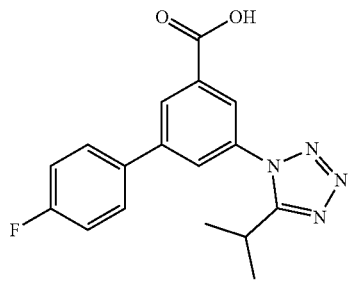 [SMILES: CC(C)c1nnnn1-c1cc(C(=O)O)cc(-c2ccc(F)cc2)c1]

Step A

Methyl 3-(4-fluorophenyl)-5-(2-methylpropanoylamino)-benzoate, white solid (0.66 g, 100%), MS (ISP) m/z=316.2 [(M+H)$^+$], mp 150° C., was prepared in accordance with the general method of intermediate 4, step A, from methyl 3-amino-5-(4-fluorophenyl)-benzoate (intermediate 1, step A) (0.515 g, 2.10 mmol) and isobutyryl chloride (274 mg, 272 µl, 2.52 mmol).

Step B

Methyl 3-(4-fluorophenyl)-5-(5-propan-2-yltetrazol-1-yl)-benzoate, off-white solid (0.70 g, 100%), MS (ISP) m/z=341.2 [(M+H)$^+$], mp 161.5° C., was prepared in accordance with the general method of intermediate 4, step B, from methyl 3-(4-fluorophenyl)-5-(2-methylpropanoylamino)-benzoate (0.65 g, 2.06 mmol).

Step C

The title compound, white solid (0.67 g, 100%), MS (ISP) m/z=327.1 [(M+H)$^+$], mp 240.5° C., was prepared in accordance with the general method of intermediate 1, step C, from methyl 3-(4-fluorophenyl)-5-(5-propan-2-yltetrazol-1-yl)-benzoate (0.70 g, 2.06 mmol).

Intermediate 11: 3-(5-Cyclopropyltetrazol-1-yl)-5-(4-fluorophenyl)-benzoic acid

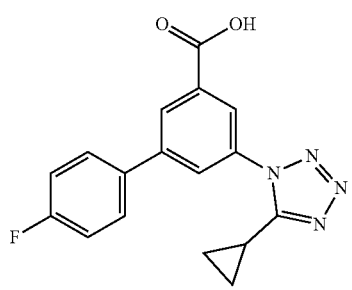 [SMILES: O=C(O)c1cc(-c2ccc(F)cc2)cc(-n2nnnc2C2CC2)c1]

Step A

Methyl 3-(cyclopropanecarbonylamino)-5-(4-fluorophenyl)-benzoate, off-white solid (0.76 g, 98%), MS (ISP) m/z=314.2 [(M+H)$^+$], mp 160° C., was prepared in accordance with the general method of intermediate 4, step A, from methyl 3-amino-5-(4-fluorophenyl)-benzoate (intermediate 1, step A) (0.61 g, 2.49 mmol) and cyclopropanecarbonyl chloride (318 mg, 279 µl, 2.98 mmol).

Step B

Methyl 3-(5-cyclopropyltetrazol-1-yl)-5-(4-fluorophenyl)-benzoate, light yellow solid (0.79 g, 96%), MS (ISP) m/z=339.2 [(M+H)$^+$], mp 122° C., was prepared in accordance with the general method of intermediate 4, step B, from methyl 3-(cyclopropanecarbonylamino)-5-(4-fluorophenyl)-benzoate (0.76 g, 2.43 mmol).

Step C

The title compound, white solid (0.76 g, 100%), MS (ISP) m/z=325.1 [(M+H)$^+$], mp 187° C., was prepared in accordance with the general method of intermediate 1, step C, from methyl 3-(5-cyclopropyltetrazol-1-yl)-5-(4-fluorophenyl)-benzoate (0.79 g, 2.33 mmol).

Intermediate 12: 3-(4-Fluorophenyl)-5-(5-methyltetrazol-1-yl)-benzoic acid

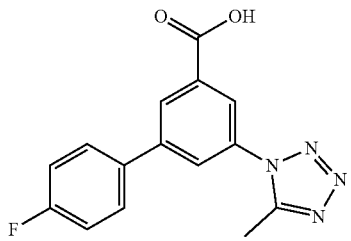 [SMILES: Cc1nnnn1-c1cc(C(=O)O)cc(-c2ccc(F)cc2)c1]

Step A

Methyl 3-acetamido-5-(4-fluorophenyl)-benzoate, light yellow solid (0.61 g, 99%), MS (ISP) m/z=288.1 [(M+H)$^+$], mp 122° C., was prepared in accordance with the general method of intermediate 4, step A, from methyl 3-amino-5-(4-fluorophenyl)-benzoate (intermediate 1, step A) (0.515 g, 2.10 mmol) and acetyl chloride (200 mg, 181 □l, 2.52 mmol).

Step B

Methyl 3-(4-fluorophenyl)-5-(5-methyltetrazol-1-yl)-benzoate, light yellow solid (0.70 g, 93%), MS (ISP) m/z=313.1 [(M+H)$^+$], mp 132° C., was prepared in accordance with the general method of intermediate 4, step B, from methyl 3-acetamido-5-(4-fluorophenyl)-benzoate (0.61 g, 2.06 mmol).

Step C

The title compound, off-white solid (0.56 g, 90%), MS (ISP) m/z=299.1 [(M+H)$^+$], mp 213.5° C., was prepared in accordance with the general method of intermediate 1, step C, from methyl 3-(4-fluorophenyl)-5-(5-methyltetrazol-1-yl)-benzoate (0.65 g, 2.08 mmol).

Intermediate 13: 3-(4-Chlorophenyl)-5-(5-methyltetrazol-1-yl)-benzoic acid

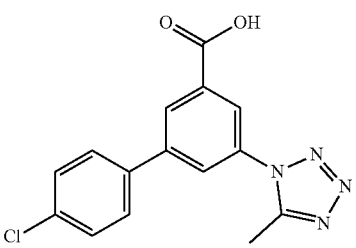 [SMILES: Cc1nnnn1-c1cc(C(=O)O)cc(-c2ccc(Cl)cc2)c1]

Step A

Methyl 3-acetamido-5-(4-chlorophenyl)-benzoate, light yellow solid (0.59 g, 93%), MS (ISP) m/z=304.1 [(M+H)$^+$], mp 151° C., was prepared in accordance with the general method of intermediate 4, step A, from methyl 3-amino-5-(4-chlorophenyl)-benzoate (intermediate 8, step A) (0.547 g, 2.09 mmol) and acetyl chloride (197 mg, 178 µl, 2.51 mmol).

Step B

Methyl 3-(4-chlorophenyl)-5-(5-methyltetrazol-1-yl)-benzoate, light brown solid (0.57 g, 89%), MS (ISP) m/z=329.1 [(M+H)$^+$], mp 147.5° C., was prepared in accordance with the general method of intermediate 4, step B, from methyl 3-acetamido-5-(4-chlorophenyl)-benzoate (0.59 g, 1.94 mmol).

Step C

The title compound, off-white solid (0.53 g, 99%), MS (ISP) m/z=315.1 [(M+H)$^+$], mp 216° C., was prepared in accordance with the general method of intermediate 1, step C, from methyl 3-(4-chlorophenyl)-5-(5-methyltetrazol-1-yl)-benzoate (0.56 g, 1.70 mmol).

Intermediate 14: 3-(4-Chlorophenyl)-5-[5-(trifluoromethyl)-tetrazol-1-yl]-benzoic acid

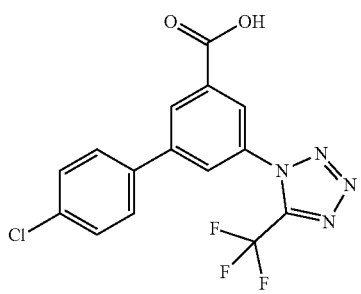 [SMILES: O=C(O)c1cc(-c2ccc(Cl)cc2)cc(-n2nnnc2C(F)(F)F)c1]

Step A

A mixture of 2,2,2-trifluoroacetic acid (257 mg, 174 µl, 2.25 mmol), triphenylphosphine (1.48 g, 5.64 mmol) and triethylamine (228 mg, 314 µl, 2.25 mmol) in carbon tetrachloride (3.6 ml) was stirred at 0° C. for 10 min, methyl 3-amino-5-(4-chlorophenyl)-benzoate (intermediate 7, step A) (590 mg, 2.25 mmol) was added, the reaction mixture was stirred under reflux conditions for 2 h, and purified by flash chromatography on silica gel [heptane/ethyl acetate (0-50%)] to yield (Z)-methyl 4'-chloro-5-((1-chloro-2,2,2-trifluoroethylidene)-amino)-[1,1'-biphenyl]-3-carboxylate (0.52 g, 1.38 mmol) as a yellow oil, which was subsequently dissolved in acetonitrile (3.7 ml). To the stirred solution was added at room temperature sodium azide (180 mg, 2.76 mmol), the reaction mixture was allowed to stir at room temperature for 15 h, poured into cold 2N Na$_2$CO$_3$ solution (50 ml) and extracted with ethyl acetate (2×50 ml). The combined organic layers were washed with brine (50 ml), dried (MgSO$_4$) and evaporated. The crude product (0.55 g) was purified by flash chromatography on silica gel [dichloromethane/dichloromethane-MeOH 9:1 (0-25%)] to yield methyl 3-(4-chlorophenyl)-5-[5-(trifluoromethyl)-tetrazol-1-yl]-benzoate (0.46 g, 53%) as an off-white solid, MS (ISP) m/z=383.0 [(M+H)$^+$], mp 195° C.

Step B

The title compound, white solid (0.42 g, 95%), MS (ISN) m/z=367.2 [(M−H)$^-$], mp 228° C., was prepared in accordance with the general method of intermediate 1, step C, from methyl 3-(4-chlorophenyl)-5-[5-(trifluoromethyl)-tetrazol-1-yl]-benzoate (0.46 g, 1.20 mmol).

Intermediate 15: 3-(5-tert-Butyltetrazol-1-yl)-5-(4-chlorophenyl)-benzoic acid

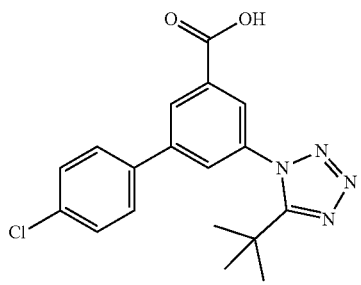 [SMILES: CC(C)(C)c1nnnn1-c1cc(C(=O)O)cc(-c2ccc(Cl)cc2)c1]

Step A

Methyl 3-(4-chlorophenyl)-5-(2,2-dimethylpropanoylamino)-benzoate, light yellow solid (0.64 g, 90%), MS (ISP) m/z=346.2 [(M+H)$^+$], mp 183° C., was prepared in accordance with the general method of intermediate 4, step A, from methyl 3-amino-5-(4-chlorophenyl)-benzoate (intermediate 8, step A) (0.54 g, 2.06 mmol) and pivaloyl chloride (298 mg, 304 µl, 2.47 mmol).

Step B

Methyl 3-(5-tert-butyltetrazol-1-yl)-5-(4-chlorophenyl)-benzoate, off-white solid (0.64 g, 93%), MS (ISP) m/z=371.2 [(M+H)$^+$], mp 195.5° C., was prepared in accordance with the general method of intermediate 4, step B, from methyl 3-(4-chlorophenyl)-5-(2,2-dimethylpropanoylamino)-benzoate (0.64 g, 1.85 mmol).

Step C

The title compound, off-white solid (0.61 g, 99%), MS (ISP) m/z=357.1 [(M+H)$^+$], mp 276.5° C., was prepared in accordance with the general method of intermediate 1, step C, from methyl 3-(5-tert-butyltetrazol-1-yl)-5-(4-chlorophenyl)-benzoate (0.64 g, 1.73 mmol).

Intermediate 16: 3-(5-tert-Butyltetrazol-1-yl)-5-(4-fluorophenyl)-benzoic acid

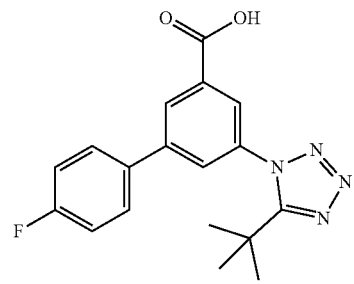 [SMILES: CC(C)(C)c1nnnn1-c1cc(C(=O)O)cc(-c2ccc(F)cc2)c1]

Step A

Methyl 3-(2,2-dimethylpropanoylamino)-5-(4-fluorophenyl)-benzoate, light yellow solid (0.78 g, 100%), MS (ISP) m/z=330.2 [(M+H)$^+$], mp 125.5° C., was prepared in accordance with the general method of intermediate 4, step A, from methyl 3-amino-5-(4-fluorophenyl)-benzoate (intermediate 1, step A) (0.58 g, 2.36 mmol) and pivaloyl chloride (342 mg, 349 µl, 2.84 mmol).

Step B

Methyl 3-(5-tert-butyltetrazol-1-yl)-5-(4-fluorophenyl)-benzoate, white solid (0.78 g, 93%), MS (ISP) m/z=355.1

[(M+H)⁺], mp 177.5° C., was prepared in accordance with the general method of intermediate 4, step B, from methyl 3-(2,2-dimethylpropanoylamino)-5-(4-fluorophenyl)-benzoate (0.78 g, 2.37 mmol).
Step C The title compound, white solid (0.75 g, 100%), MS (ISP) m/z=341.1 [(M+H)⁺], mp 241° C., was prepared in accordance with the general method of intermediate 1, step C, from methyl 3-(5-tert-butyltetrazol-1-yl)-5-(4-fluorophenyl)-benzoate (0.78 g, 2.20 mmol).

Intermediate 17: 3-Bromo-N-tert-butyl-5-(5-tert-butyltetrazol-1-yl)-benzamide

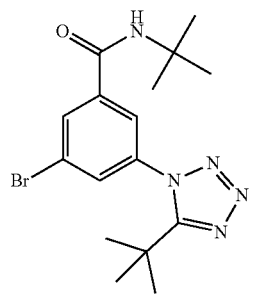 [SMILES: CC(C)(C)NC(=O)c1cc(Br)cc(-n2nnnc2C(C)(C)C)c1]

Step A

To a stirred solution of commercially available 3-amino-5-bromobenzoic acid (4 g, 18.5 mmol) in MeOH (45 ml) was added dropwise at 0° C. thionyl chloride (2.42 g, 1.49 ml, 20.4 mmol), the reaction mixture was allowed to warm to room temperature, afterwards stirred under reflux conditions for 2 h and evaporated. The crude product was acylated without further purification using pivaloyl chloride (2.66 g, 2.72 ml, 22.1 mmol) according to the general method of intermediate 4, step A, to yield methyl 3-bromo-5-pivalamidobenzoate as light yellow oil (5.81 g, 100%), MS (ISP) m/z=316.0 [(M+H)⁺].
Step B 3-Bromo-5-(5-(tert-butyl)-1H-tetrazol-1-yl)-benzoate, white solid (6.06 g, 97%), MS (ISP) m/z=339.0 [(M+H)⁺], mp 135.5° C., was prepared in accordance with the general method of intermediate 4, step B, from methyl 3-bromo-5-pivalamidobenzoate (5.81 g, 18.5 mmol).
Step C To a stirred solution of methyl 3-bromo-5-(5-(tert-butyl)-1H-tetrazol-1-yl)-benzoate (6.05 g, 17.8 mmol) in THF (29.7 ml), MeOH (29.7 ml) and water (29.7 ml), lithium hydroxide monohydrate (973 mg, 23.2 mmol) was added at room temperature, the reaction mixture was stirred at room temperature for 2.5 h, concentrated to one third and 2N hydrochloride solution (35.6 ml) was added. The precipitate was collected by filtration, washed with water (10 ml) and dried to yield 3-bromo-5-(5-(tert-butyl)-1H-tetrazol-1-yl)-benzoic acid as white solid (5.77 g, 99%), MS (ISP) m/z=325.0 [(M+H)⁺], mp 218° C.
Step D The title compound, white foam (1.17 g, 99%), MS (ISP) m/z=380.1 [(M+H)⁺], mp 99.5° C., was prepared in accordance with the general method of example 1 from 3-bromo-5-(5-(tert-butyl)-1H-tetrazol-1-yl)-benzoic acid (1.01 g, 3.10 mmol) and commercially available 2-methylpropan-2-amine (278 mg, 399 µl, 3.72 mmol).

Intermediate 18: 3-Bromo-5-(5-tert-butyltetrazol-1-yl)-N-(2-cyclopropylpropan-2-yl)benzamide

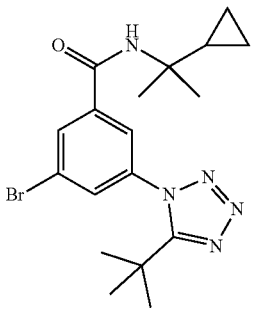 [SMILES: CC(C)(C)c1nnnn1-c1cc(Br)cc(C(=O)NC(C)(C)C2CC2)c1]

The title compound, white solid (1.19 g, 95%), MS (ISP) m/z=406.1 [(M+H)⁺], mp 164° C., was prepared in accordance with the general method of example 1 from 3-bromo-5-(5-(tert-butyl)-1H-tetrazol-1-yl)-benzoic acid (intermediate 16, step C) (1.01 g, 3.10 mmol) and commercially available 2-cyclopropylpropan-2-amine hydrochloride (505 mg, 3.72 mmol).

Intermediate 19: 3-Bromo-5-(5-tert-butyltetrazol-1-yl)-N-(1,1,1-trifluoro-2-methylpropan-2-yl)-benzamide

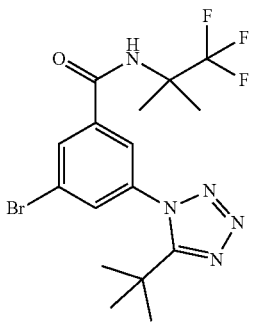 [SMILES: CC(C)(C)c1nnnn1-c1cc(Br)cc(C(=O)NC(C)(C)C(F)(F)F)c1]

The title compound, white solid (0.58 g, 86%), MS (ISP) m/z=434.1 [(M+H)⁺], mp 173° C., was prepared in accordance with the general method of example 1 from 3-bromo-5-(5-(tert-butyl)-1H-tetrazol-1-yl)-benzoic acid (intermediate 16, step C) (504 mg, 1.55 mmol) and commercially available 1,1,1-trifluoro-2-methylpropan-2-amine (241 mg, 1.86 mmol).

Intermediate 20: 3-Bromo-5-(5-tert-butyltetrazol-1-yl)-N-(2-cyanopropan-2-yl)-benzamide

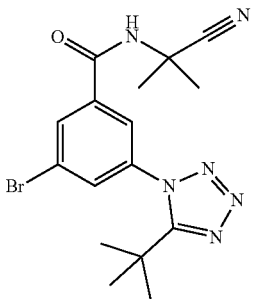 [SMILES: CC(C)(C#N)NC(=O)c1cc(Br)cc(-n2nnnc2C(C)(C)C)c1]

The title compound, yellow solid (0.38 g, 63%), MS (ISP) m/z=393.1 [(M+H)+], mp 175.5° C., was prepared in accordance with the general method of example 1 from 3-bromo-5-(5-(tert-butyl)-1H-tetrazol-1-yl)-benzoic acid (intermediate 16, step C) (504 mg, 1.55 mmol) and commercially available 2-amino-2-methyl-propanenitrile (156 mg, 1.86 mmol).

Example 1

3-(4-Fluorophenyl)-N-(2-methylbutan-2-yl)-5-(tetrazol-1-yl)-benzamide

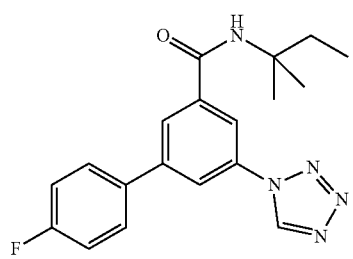 [SMILES: CCC(C)(C)NC(=O)c1cc(-c2ccc(F)cc2)cc(-n2cnnn2)c1]

To a stirred solution of commercially available 2-methylbutan-2-amine (21.8 mg, 29.2 µl, 0.25 mmol) in THF (1.8 ml) was added N,N-diisopropylethylamine (80.8 mg, 107 µl, 625 µmol), 3-(4-fluorophenyl)-5-(tetrazol-1-yl)-benzoic acid (intermediate 1) (85.3 mg, 0.30 mmol) and 0-(benzotriazol-1-yl)-N,N,N',N'-tetramethyluronium tetrafluoroborate (TBTU) (128 mg, 400 µmol). The reaction mixture was stirred at room temperature for 17 h and purified by flash chromatography on silica gel [heptane/ethyl acetate (0-100%)] and trituration from dichloromethane (1 ml) and heptane (15 ml) to yield the title compound (85 mg, 96%) as a white solid, MS (ISP) m/z=354.1 [(M+H)+], mp 200° C.

Example 2

N-(2-Methylbutan-2-yl)-3-(tetrazol-1-yl)-5-[4-(trifluoromethyl)phenyl]-benzamide

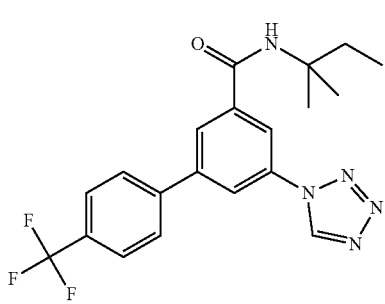 [SMILES: CCC(C)(C)NC(=O)c1cc(-c2ccc(C(F)(F)F)cc2)cc(-n2cnnn2)c1]

The title compound, off-white solid (57 mg, 71%), MS (ISP) m/z=404.2 [(M+H)+], mp 168° C., was prepared in accordance with the general method of example 1 from 3-(tetrazol-1-yl)-5-[4-(trifluoromethyl)-phenyl]-benzoic acid (intermediate 2) (80.2 mg, 0.24 mmol) and commercially available 2-methylbutan-2-amine (17.4 mg, 23.4 µl, 0.2 mmol).

Example 3

N-tert-Butyl-3-(tetrazol-1-yl)-5-[4-(trifluoromethyl)phenyl]-benzamide

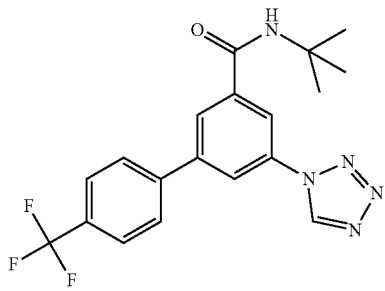

The title compound, off-white solid (48 mg, 62%), MS (ISP) m/z=390.2 [(M+H)+], mp 108° C., was prepared in accordance with the general method of example 1 from 3-(tetrazol-1-yl)-5-[4-(trifluoromethyl)-phenyl]-benzoic acid (intermediate 2) (80.2 mg, 0.24 mmol) and commercially available 2-methylpropan-2-amine (14.9 mg, 21.4 µl, 0.2 mmol).

Example 4

(RS)-3-(4-Fluorophenyl)-N-(3-methyl-1,1-dioxothiolan-3-yl)-5-(tetrazol-1-yl)-benzamide

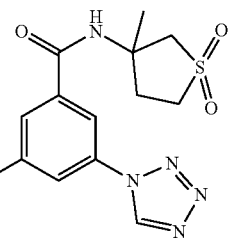

The title compound, white solid (100 mg, 96%), MS (ISP) m/z=416.2 [(M+H)+], mp 146.5° C., was prepared in accordance with the general method of example 1 from 3-(4-fluorophenyl)-5-(tetrazol-1-yl)-benzoic acid (intermediate 1) (85.3 mg, 0.30 mmol) and commercially available (RS)-3-amino-3-methyltetrahydrothiophene 1,1-dioxide hydrochloride (46.4 mg, 0.25 mmol).

Example 5

3-(3-Fluoro-4-methylphenyl)-N-(2-methylbutan-2-yl)-5-(tetrazol-1-yl)-benzamide

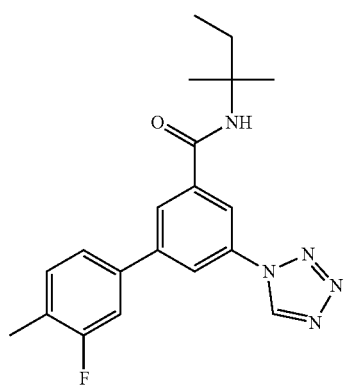 [SMILES: CCC(C)(C)NC(=O)c1cc(-c2ccc(C)c(F)c2)cc(-n2cnnn2)c1]

A mixture of 3-iodo-N-tert-pentyl-5-(1H-tetrazol-1-yl)-benzamide (intermediate 3) (96.3 mg, 0.25 mmol) and commercially available 3-fluoro-4-methylphenylboronic acid (50.0 mg, 325 μmol) in 1,2-dimethoxyethane (1.67 ml) and 2 M $Na_2CO_3$ solution (416 μl, 832 μmol) was purged with argon in an ultrasonic bath for 5 min, triphenylphosphine (13.1 mg, 50.0 μmol) and palladium(II)acetate (5.61 mg, 25.0 μmol) were added at room temperature, and afterwards the reaction mixture was stirred for 3 h under reflux conditions. The reaction mixture was cooled to room temperature and purified by flash chromatography on silica gel [heptane/ethyl acetate (10-50%)] and crystallization from dichloromethane/heptane to yield the title compound (63 mg, 69%) as a white solid, MS (ISP) m/z=368.2 [(M+H)+], mp 161° C.

Example 6

3-(4-Fluoro-3-methylphenyl)-N-(2-methylbutan-2-yl)-5-(tetrazol-1-yl)-benzamide

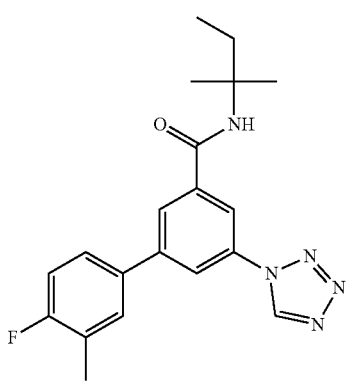

The title compound, off-white solid (61 mg, 66%), MS (ISP) m/z=368.2 [(M+H)+], mp 120° C., was prepared in accordance with the general method of example 7 from 3-iodo-N-tert-pentyl-5-(1H-tetrazol-1-yl)-benzamide (intermediate 3) (96.3 mg, 0.25 mmol) and commercially available 4-fluoro-3-methylphenylboronic acid (50.0 mg, 325 μmol).

Example 7

3-(4-Methoxyphenyl)-N-(2-methylbutan-2-yl)-5-(tetrazol-1-yl)-benzamide

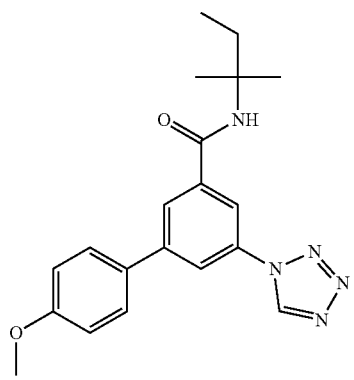 [SMILES: CCC(C)(C)NC(=O)c1cc(-c2ccc(OC)cc2)cc(-n2cnnn2)c1]

The title compound, light brown solid (66 mg, 72%), MS (ISP) m/z=366.2 [(M+H)+], mp 150° C., was prepared in accordance with the general method of example 7 from 3-iodo-N-tert-pentyl-5-(1H-tetrazol-1-yl)-benzamide (intermediate 3) (96.3 mg, 0.25 mmol) and commercially available 4-methoxyphenylboronic acid (49.4 mg, 325 μmol).

Example 8

N-(2-Methylbutan-2-yl)-3-(4-propan-2-ylphenyl)-5-(tetrazol-1-yl)-benzamide

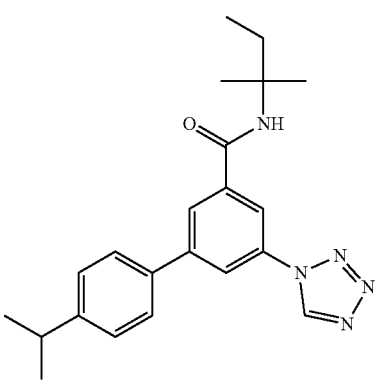 [SMILES: CCC(C)(C)NC(=O)c1cc(-c2ccc(C(C)C)cc2)cc(-n2cnnn2)c1]

The title compound, white foam (81 mg, 86%), MS (ISP) m/z=378.3 [(M+H)+], was prepared in accordance with the general method of example 7 from 3-iodo-N-tert-pentyl-5-(1H-tetrazol-1-yl)-benzamide (intermediate 3) (96.3 mg, 0.25 mmol) and commercially available 4-isopropylphenylboronic acid (53.3 mg, 325 μmol).

Example 9

3-(4-Cyclopropylphenyl)-N-(2-methylbutan-2-yl)-5-(tetrazol-1-yl)-benzamide

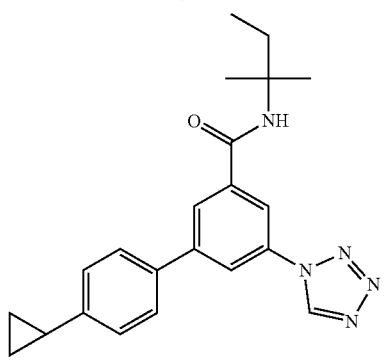 [SMILES: CCC(C)(C)NC(=O)c1cc(-c2ccc(C3CC3)cc2)cc(-n2cnnn2)c1]

The title compound, white foam (75 mg, 80%), MS (ISP) m/z=376.2 [(M+H)+], was prepared in accordance with the general method of example 7 from 3-iodo-N-tert-pentyl-5-(1H-tetrazol-1-yl)-benzamide (intermediate 3) (96.3 mg, 0.25 mmol) and commercially available 4-cyclopropylphenylboronic acid (52.6 mg, 325 µmol).

Example 10

N-(2-Methylbutan-2-yl)-3-(4-methylphenyl)-5-(5-propan-2-yltetrazol-1-yl)-benzamide

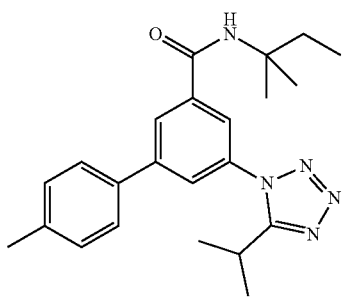 [SMILES: CCC(C)(C)NC(=O)c1cc(-c2ccc(C)cc2)cc(-n2nnnc2C(C)C)c1]

The title compound, white solid (81 mg, 83%), MS (ISP) m/z=392.3 [(M+H)+], mp 104° C., was prepared in accordance with the general method of example 1 from 3-(4-methylphenyl)-5-(5-propan-2-yltetrazol-1-yl)-benzoic acid (intermediate 4) (96.7 mg, 0.30 mmol) and commercially available 2-methylbutan-2-amine (21.8 mg, 29.2 µl, 0.25 mmol).

Example 11

3-(4-Chlorophenyl)-N-(2-methylbutan-2-yl)-5-(tetrazol-1-yl)-benzamide

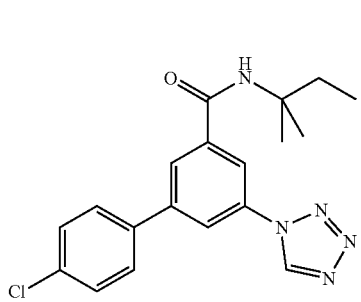 [SMILES: CCC(C)(C)NC(=O)c1cc(-c2ccc(Cl)cc2)cc(-n2cnnn2)c1]

The title compound, white solid (67 mg, 90%), MS (ISP) m/z=370.2 [(M+H)+], mp 206° C., was prepared in accordance with the general method of example 1 from 3-(4-chlorophenyl)-5-(tetrazol-1-yl)-benzoic acid [CAS No. 1138323-00-8] (72.2 mg, 0.24 mmol) and commercially available 2-methylbutan-2-amine (17.4 mg, 23.4 µl, 0.2 mmol).

Example 12

N-tert-Butyl-3-(4-chlorophenyl)-5-(tetrazol-1-yl)-benzamide

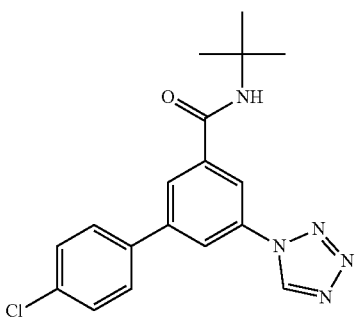 [SMILES: CC(C)(C)NC(=O)c1cc(-c2ccc(Cl)cc2)cc(-n2cnnn2)c1]

The title compound, white solid (50 mg, 70%), MS (ISP) m/z=356.2 [(M+H)+], mp 199° C., was prepared in accordance with the general method of example 1 from 3-(4-chlorophenyl)-5-(tetrazol-1-yl)-benzoic acid [CAS No. 1138323-00-8] (80.2 mg, 0.24 mmol) and commercially available 2-methylpropan-2-amine (14.9 mg, 21.4 µl, 0.2 mmol).

Example 13

3-(4-Methylphenyl)-5-(tetrazol-1-yl)-N-(1,1,1-trifluoro-2-methylpropan-2-yl)-benzamide

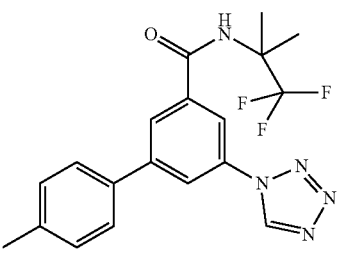 [SMILES: Cc1ccc(-c2cc(C(=O)NC(C)(C)C(F)(F)F)cc(-n3cnnn3)c2)cc1]

The title compound, white solid (65 mg, 67%), MS (ISP) m/z=390.2 [(M+H)+], mp 190.5° C., was prepared in accordance with the general method of example 1 from 3-(4-methylphenyl)-5-(tetrazol-1-yl)-benzoic acid [CAS No. 1000587-33-6] (70.1 mg, 0.25 mmol) and commercially available 1,1,1-trifluoro-2-methylpropan-2-amine (38.9 mg, 0.3 mmol).

Example 14

N-(1-Hydroxy-2-methylpropan-2-yl)-3-(4-methylphenyl)-5-(5-propan-2-yltetrazol-1-yl)-benzamide

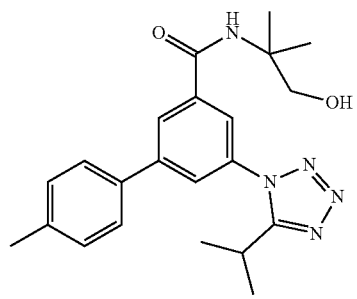 [SMILES: Cc1ccc(-c2cc(C(=O)NC(C)(C)CO)cc(-n3nnnc3C(C)C)c2)cc1]

The title compound, white foam (77 mg, 78%), MS (ISP) m/z=394.3 [(M+H)+], mp 75° C., was prepared in accordance with the general method of example 1 from 3-(4-methylphenyl)-5-(5-propan-2-yltetrazol-1-yl)-benzoic acid (intermediate 4) (96.7 mg, 0.30 mmol) and commercially available 2-amino-2-methylpropan-1-ol (22.3 mg, 24.0 µl, 0.25 mmol).

Example 15

3-(4-Chlorophenyl)-N-(1-hydroxy-2-methylpropan-2-yl)-5-(tetrazol-1-yl)-benzamide

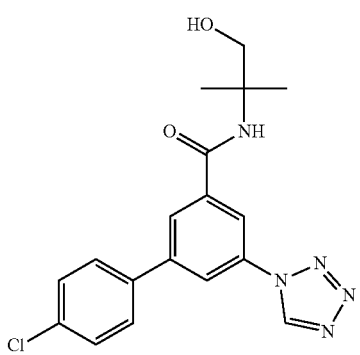 [SMILES: CC(C)(CO)NC(=O)c1cc(-c2ccc(Cl)cc2)cc(-n2cnnn2)c1]

The title compound, white solid (12 mg, 16%), MS (ISP) m/z=372.2 [(M+H)+], mp 137° C., was prepared in accordance with the general method of example 1 from 3-(4-chlorophenyl)-5-(tetrazol-1-yl)-benzoic acid [CAS No. 1138323-00-8] (80.2 mg, 0.24 mmol) and commercially available 2-amino-2-methylpropan-1-ol (22.3 mg, 24.0 µl, 0.25 mmol).

Example 16

(RS)-3-(4-Chlorophenyl)-N-(3-methyl-1,1-dioxothiolan-3-yl)-5-(tetrazol-1-yl)-benzamide

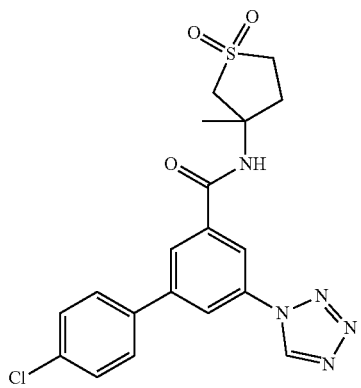 [SMILES: CC1(NC(=O)c2cc(-c3ccc(Cl)cc3)cc(-n3cnnn3)c2)CCS(=O)(=O)C1]

The title compound, white solid (61 mg, 71%), MS (ISP) m/z=432.2 [(M+H)+], mp 204° C., was prepared in accordance with the general method of example 1 from 3-(4-chlorophenyl)-5-(tetrazol-1-yl)-benzoic acid [CAS No. 1138323-00-8] (80.2 mg, 0.24 mmol) and commercially available (RS)-3-amino-3-methyltetrahydrothiophene 1,1-dioxide hydrochloride (37.1 mg, 0.2 mmol).

Example 17

(RS)—N-(3-methyl-1,1-dioxothiolan-3-yl)-3-(4-methylphenyl)-5-(5-propan-2-yltetrazol-1-yl)-benzamide

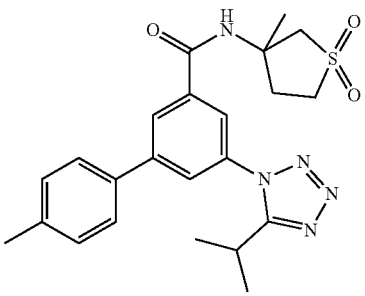 [SMILES: Cc1ccc(-c2cc(C(=O)NC3(C)CCS(=O)(=O)C3)cc(-n3nnnc3C(C)C)c2)cc1]

The title compound, white solid (100 mg, 88%), MS (ISP) m/z=454.3 [(M+H)+], mp 112° C., was prepared in accordance with the general method of example 1 from 3-(4-methylphenyl)-5-(5-propan-2-yltetrazol-1-yl)-benzoic acid (intermediate 4) (96.7 mg, 0.30 mmol) and commercially available (RS)-3-amino-3-methyltetrahydrothiophene 1,1-dioxide hydrochloride (46.4 mg, 0.25 mmol).

Example 18

3-(4-Fluorophenyl)-5-(tetrazol-1-yl)-N-(1,1,1-trifluoro-2-methylpropan-2-yl)-benzamide

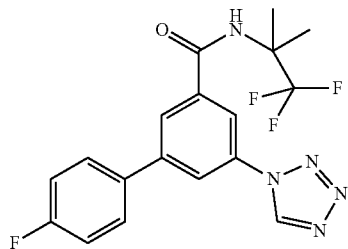 [SMILES: CC(C)(NC(=O)c1cc(-c2ccc(F)cc2)cc(-n2cnnn2)c1)C(F)(F)F]

The title compound, off-white solid (0.02 mg, 20%), MS (ISP) m/z=394.2 [(M+H)⁺], mp 175° C., was prepared in accordance with the general method of example 1 from 3-(4-fluorophenyl)-5-(tetrazol-1-yl)-benzoic acid (intermediate 1) (71.1 mg, 0.25 mmol) and commercially available 1,1,1-trifluoro-2-methylpropan-2-amine (38.9 mg, 0.3 mmol).

Example 19

3-(4-Methylphenyl)-5-(5-propan-2-yltetrazol-1-yl)-N-(1,1,1-trifluoro-2-methylpropan-2-yl)-benzamide

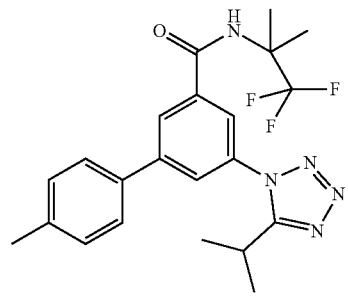 [SMILES: Cc1ccc(-c2cc(C(=O)NC(C)(C)C(F)(F)F)cc(-n3nnnc3C(C)C)c2)cc1]

The title compound, white foam (100 mg, 93%), MS (ISP) m/z=432.3 [(M+H)⁺], mp 79° C., was prepared in accordance with the general method of example 1 from 3-(4-methylphenyl)-5-(5-propan-2-yltetrazol-1-yl)-benzoic acid (intermediate 4) (80.6 mg, 0.25 mmol) and commercially available 1,1,1-trifluoro-2-methylpropan-2-amine (38.9 mg, 0.3 mmol).

Example 20

N-(2-Cyclopropylpropan-2-yl)-3-(4-methylphenyl)-5-(5-propan-2-yltetrazol-1-yl)-benzamide

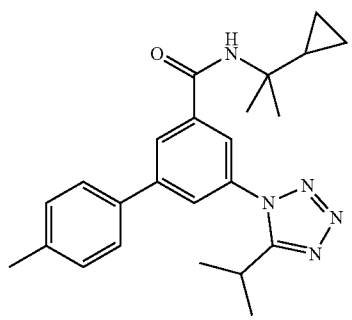 [SMILES: Cc1ccc(-c2cc(C(=O)NC(C)(C)C3CC3)cc(-n3nnnc3C(C)C)c2)cc1]

The title compound, white foam (95 mg, 94%), MS (ISP) m/z=404.3 [(M+H)⁺], mp 78° C., was prepared in accordance with the general method of example 1 from 3-(4-methylphenyl)-5-(5-propan-2-yltetrazol-1-yl)-benzoic acid (intermediate 4) (96.7 mg, 0.30 mmol) and commercially available 2-cyclopropylpropan-2-amine (24.8 mg, 0.25 mmol).

Example 21

N-(2-cyclopropylpropan-2-yl)-3-(4-fluorophenyl)-5-(tetrazol-1-yl)-benzamide

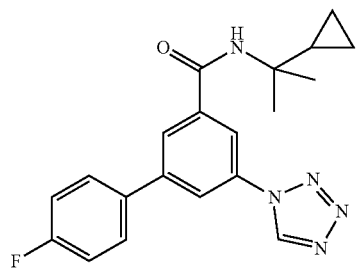 [SMILES: CC(C)(NC(=O)c1cc(-c2ccc(F)cc2)cc(-n2cnnn2)c1)C1CC1]

The title compound, white solid (85 mg, 93%), MS (ISP) m/z=366.2 [(M+H)⁺], mp 193° C., was prepared in accordance with the general method of example 1 from 3-(4-fluorophenyl)-5-(tetrazol-1-yl)-benzoic acid (intermediate 1) (85.3 mg, 0.30 mmol) and commercially available 2-cyclopropylpropan-2-amine (24.8 mg, 0.25 mmol).

Example 22

N-(2-methylbutan-2-yl)-3-(4-methylphenyl)-5-(5-methyltetrazol-1-yl)-benzamide

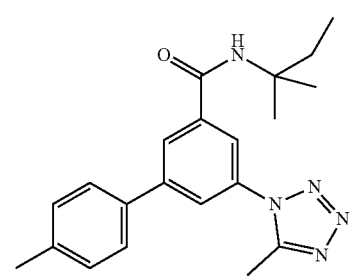 [SMILES: CCC(C)(C)NC(=O)c1cc(-c2ccc(C)cc2)cc(-n2nnnc2C)c1]

The title compound, white foam (89 mg, 98%), MS (ISP) m/z=364.3 [(M+H)⁺], mp 80° C., was prepared in accordance with the general method of example 1 from 3-(4-methylphenyl)-5-(5-methyltetrazol-1-yl)benzoic acid [CAS No. 1000587-69-8] (88.3 mg, 0.30 mmol) and commercially available 2-methylbutan-2-amine (21.8 mg, 29.2 µl, 0.25 mmol).

Example 23

N-tert-Butyl-3-(4-methylphenyl)-5-(5-methyltetrazol-1-yl)-benzamide

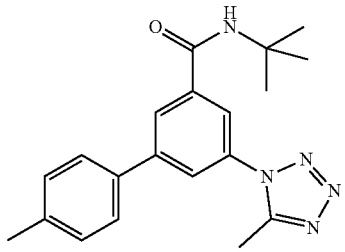 [SMILES: Cc1ccc(-c2cc(C(=O)NC(C)(C)C)cc(-n3nnnc3C)c2)cc1]

The title compound, white foam (85 mg, 97%), MS (ISP) m/z=350.3 [(M+H)+], mp 85° C., was prepared in accordance with the general method of example 1 from 3-(4-methylphenyl)-5-(5-methyltetrazol-1-yl)benzoic acid [CAS No. 1000587-69-8] (88.3 mg, 0.30 mmol) and commercially available 2-methylpropan-2-amine (18.6 mg, 26.7 µl, 0.25 mmol).

Example 24

(RS)—N-(3-Methyl-1,1-dioxothiolan-3-yl)-3-(4-methylphenyl)-5-(5-methyltetrazol-1-yl)-benzamide

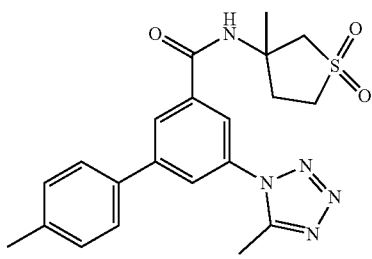 [SMILES: Cc1ccc(-c2cc(C(=O)NC3(C)CCS(=O)(=O)C3)cc(-n3nnnc3C)c2)cc1]

The title compound, off-white foam (100 mg, 94%), MS (ISP) m/z=426.2 [(M+H)+], mp 69° C., was prepared in accordance with the general method of example 1 from 3-(4-methylphenyl)-5-(5-methyltetrazol-1-yl)benzoic acid [CAS No. 1000587-69-8] (88.3 mg, 0.30 mmol) and commercially available (RS)-3-amino-3-methyltetrahydrothiophene 1,1-dioxide hydrochloride (46.4 mg, 0.25 mmol).

Example 25

3-(5-Cyclopropyltetrazol-1-yl)-5-(4-methylphenyl)-N-(1,1,1-trifluoro-2-methylpropan-2-yl)-benzamide

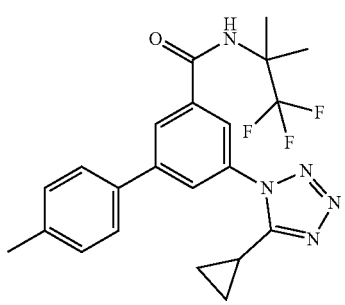 [SMILES: Cc1ccc(-c2cc(C(=O)NC(C)(C)C(F)(F)F)cc(-n3nnnc3C3CC3)c2)cc1]

The title compound, white foam (90 mg, 84%), MS (ISP) m/z=430.3 [(M+H)+], mp 82° C., was prepared in accordance with the general method of example 1 from 3-(5-cyclopropyltetrazol-1-yl)-5-(4-methylphenyl)-benzoic acid (intermediate 5) (80.1 mg, 0.25 mmol) and commercially available 1,1,1-trifluoro-2-methylpropan-2-amine (38.9 mg, 0.3 mmol).

Example 26

3-(5-Ethyltetrazol-1-yl)-5-(4-methylphenyl)-N-(1,1,1-trifluoro-2-methylpropan-2-yl)-benzamide

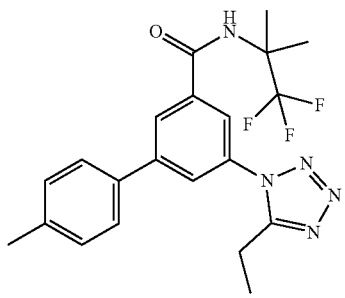 [SMILES: CCc1nnnn1-c1cc(C(=O)NC(C)(C)C(F)(F)F)cc(-c2ccc(C)cc2)c1]

The title compound, white foam (70 mg, 67%), MS (ISP) m/z=418.3 [(M+H)+], mp 78° C., was prepared in accordance with the general method of example 1 from 3-(5-ethyltetrazol-1-yl)-5-(4-methylphenyl)benzoic acid (intermediate 6) (77.1 mg, 0.25 mmol) and commercially available 1,1,1-trifluoro-2-methylpropan-2-amine (38.9 mg, 0.3 mmol).

Example 27

3-(5-Cyclopropyltetrazol-1-yl)-N-(2-methylbutan-2-yl)-5-(4-methylphenyl)-benzamide

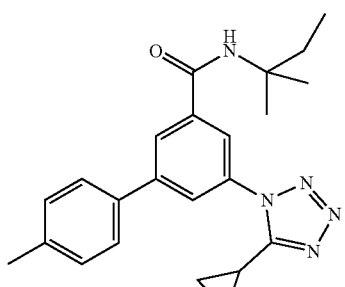

The title compound, white foam (95 mg, 98%), MS (ISP) m/z=390.3 [(M+H)+], mp 75° C., was prepared in accordance with the general method of example 1 from 3-(5-cyclopropyltetrazol-1-yl)-5-(4-methylphenyl)-benzoic acid (intermediate 5) (96.1 mg, 0.30 mmol) and commercially available 2-methylbutan-2-amine (21.8 mg, 29.2 µl, 0.25 mmol).

Example 28

3-(5-Ethyltetrazol-1-yl)-N-(2-methylbutan-2-yl)-5-(4-methylphenyl)-benzamide

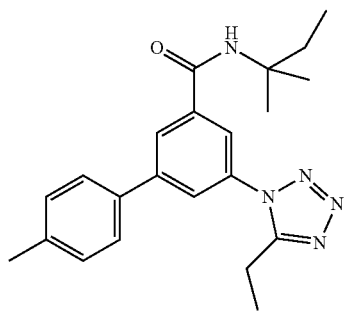 [SMILES: CCc1nnnn1-c1cc(C(=O)NC(C)(C)CC)cc(-c2ccc(C)cc2)c1]

The title compound, white foam (90 mg, 95%), MS (ISP) m/z=378.3 [(M+H)⁺], mp 71.5° C., was prepared in accordance with the general method of example 1 from 3-(5-ethyltetrazol-1-yl)-5-(4-methylphenyl)benzoic acid (intermediate 6) (92.5 mg, 0.30 mmol) and commercially available 2-methylbutan-2-amine (21.8 mg, 29.2 µl, 0.25 mmol).

Example 29

N-tert-Butyl-3-(5-cyclopropyltetrazol-1-yl)-5-(4-methylphenyl)-benzamide

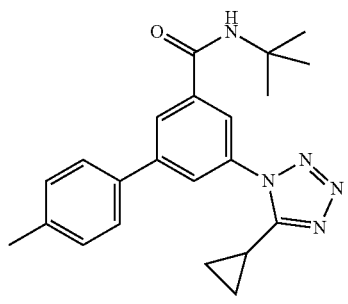 [SMILES: Cc1ccc(-c2cc(C(=O)NC(C)(C)C)cc(-n3nnnc3C3CC3)c2)cc1]

The title compound, white foam (60 mg, 64%), MS (ISP) m/z=376.3 [(M+H)⁺], mp 91° C., was prepared in accordance with the general method of example 1 from 3-(5-cyclopropyltetrazol-1-yl)-5-(4-methylphenyl)-benzoic acid (intermediate 5) (96.1 mg, 0.30 mmol) and commercially available 2-methylpropan-2-amine (18.6 mg, 26.7 µl, 0.25 mmol).

Example 30

N-tert-Butyl-3-(5-ethyltetrazol-1-yl)-5-(4-methylphenyl)-benzamide

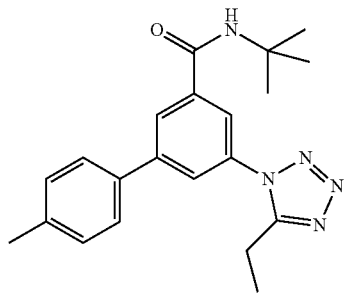 [SMILES: CCc1nnnn1-c1cc(C(=O)NC(C)(C)C)cc(-c2ccc(C)cc2)c1]

The title compound, white foam (90 mg, 99%), MS (ISP) m/z=364.3 [(M+H)⁺], mp 73° C., was prepared in accordance with the general method of example 1 from 3-(5-ethyltetrazol-1-yl)-5-(4-methylphenyl)benzoic acid (intermediate 6) (92.5 mg, 0.30 mmol) and commercially available 2-methylpropan-2-amine (18.6 mg, 26.7 µl, 0.25 mmol).

Example 31

3-(4-Chlorophenyl)-N-(2-cyclopropylpropan-2-yl)-5-(tetrazol-1-yl)-benzamide

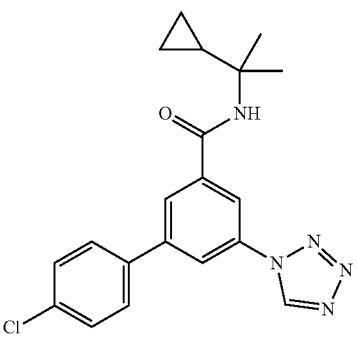 [SMILES: CC(C)(NC(=O)c1cc(-c2ccc(Cl)cc2)cc(-n2cnnn2)c1)C1CC1]

The title compound, white solid (40 mg, 53%), MS (ISP) m/z=382.3 [(M+H)⁺], mp 191° C., was prepared in accordance with the general method of example 1 from 3-(4-chlorophenyl)-5-(tetrazol-1-yl)-benzoic acid [CAS No. 1138323-00-8] (80.2 mg, 0.24 mmol) and commercially available 2-cyclopropylpropan-2-amine (19.8 mg, 0.20 mmol).

Example 32

3-(5-Cyclopropyltetrazol-1-yl)-N-(1-hydroxy-2-methylpropan-2-yl)-5-(4-methylphenyl)-benzamide

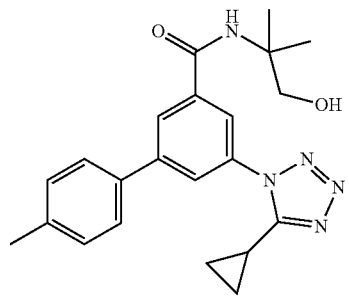 [SMILES: Cc1ccc(-c2cc(C(=O)NC(C)(C)CO)cc(-n3nnnc3C3CC3)c2)cc1]

The title compound, colorless oil (50 mg, 51%), MS (ISP) m/z=392.3 [(M+H)⁺], was prepared in accordance with the general method of example 1 from 3-(5-cyclopropyltetrazol-1-yl)-5-(4-methylphenyl)-benzoic acid (intermediate 5) (96.1 mg, 0.30 mmol) and commercially available 2-amino-2-methylpropan-1-ol (22.3 mg, 24.0 µl, 0.25 mmol).

Example 33

(RS)-3-(5-Cyclopropyltetrazol-1-yl)-N-(3-methyl-1,1-dioxothiolan-3-yl)-5-(4-methylphenyl)-benzamide

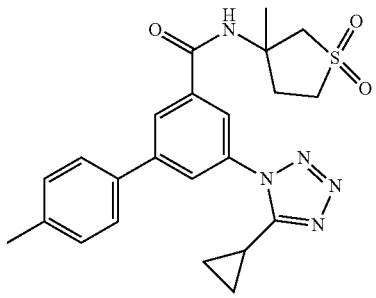 [SMILES: Cc1ccc(-c2cc(C(=O)NC3(C)CCS(=O)(=O)C3)cc(-n3nnnc3C3CC3)c2)cc1]

The title compound, white foam (100 mg, 89%), MS (ISP) m/z=452.3 [(M+H)+], mp 130.5° C., was prepared in accordance with the general method of example 1 from 3-(5-cyclopropyltetrazol-1-yl)-5-(4-methylphenyl)-benzoic acid (intermediate 5) (96.1 mg, 0.30 mmol) and commercially available (RS)-3-amino-3-methyltetrahydrothiophene 1,1-dioxide hydrochloride (46.4 mg, 0.25 mmol).

Example 34

(RS)-3-(5-Ethyltetrazol-1-yl)-N-(3-methyl-1,1-dioxothiolan-3-yl)-5-(4-methylphenyl)-benzamide

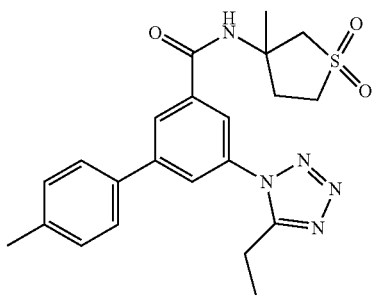 [SMILES: CCc1nnnn1-c1cc(C(=O)NC2(C)CCS(=O)(=O)C2)cc(-c2ccc(C)cc2)c1]

The title compound, white foam (100 mg, 91%), MS (ISP) m/z=440.3 [(M+H)+], mp 122° C., was prepared in accordance with the general method of example 1 from 3-(5-ethyltetrazol-1-yl)-5-(4-methylphenyl)benzoic acid (intermediate 6) (92.5 mg, 0.30 mmol) and commercially available (RS)-3-amino-3-methyltetrahydrothiophene 1,1-dioxide hydrochloride (46.4 mg, 0.25 mmol).

Example 35

N-(2-Cyclopropylpropan-2-yl)-3-(5-cyclopropyltetrazol-1-yl)-5-(4-methylphenyl)-benzamide

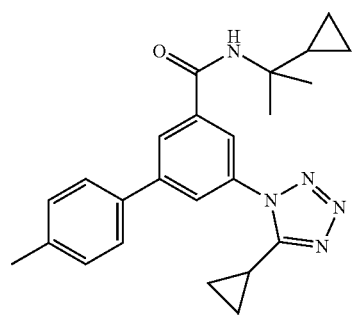 [SMILES: Cc1ccc(-c2cc(C(=O)NC(C)(C)C3CC3)cc(-n3nnnc3C3CC3)c2)cc1]

The title compound, white foam (70 mg, 70%), MS (ISP) m/z=402.3 [(M+H)+], mp 74.5° C., was prepared in accordance with the general method of example 1 from 3-(5-cyclopropyltetrazol-1-yl)-5-(4-methylphenyl)-benzoic acid (intermediate 5) (96.1 mg, 0.30 mmol) and commercially available 2-cyclopropylpropan-2-amine (24.8 mg, 0.25 mmol).

Example 36

N-(2-Cyclopropylpropan-2-yl)-3-(5-ethyltetrazol-1-yl)-5-(4-methylphenyl)-benzamide

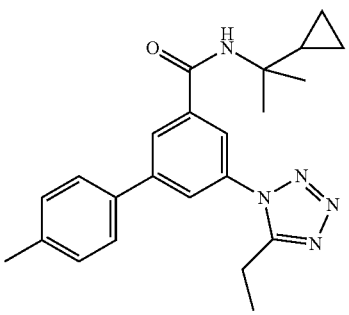 [SMILES: CCc1nnnn1-c1cc(C(=O)NC(C)(C)C2CC2)cc(-c2ccc(C)cc2)c1]

The title compound, white foam (90 mg, 92%), MS (ISP) m/z=390.3 [(M+H)+], mp 59.5° C., was prepared in accordance with the general method of example 1 from 3-(5-ethyltetrazol-1-yl)-5-(4-methylphenyl)benzoic acid (intermediate 6) (92.5 mg, 0.30 mmol) and commercially available 2-cyclopropylpropan-2-amine (24.8 mg, 0.25 mmol).

Example 37

3-(4-Chloro-3-fluorophenyl)-N-(2-methylbutan-2-yl)-5-(tetrazol-1-yl)-benzamide

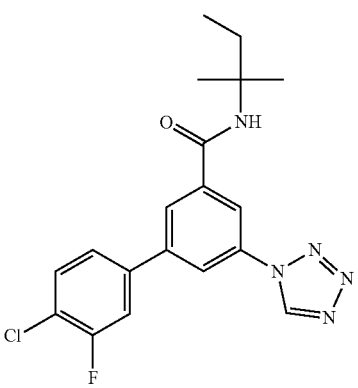 [SMILES: CCC(C)(C)NC(=O)c1cc(-c2ccc(Cl)c(F)c2)cc(-n2cnnn2)c1]

The title compound, white foam (57 mg, 59%), MS (ISP) m/z=388.2 [(M+H)+], was prepared in accordance with the general method of example 7 from 3-iodo-N-tert-pentyl-5-(1H-tetrazol-1-yl)-benzamide (intermediate 3) (96.3 mg, 0.25 mmol) and commercially available 4-chloro-3-fluorophenylboronic acid (56.7 mg, 325 μmol).

Example 38

3-(3,4-Dichlorophenyl)-N-(2-methylbutan-2-yl)-5-(tetrazol-1-yl)-benzamide

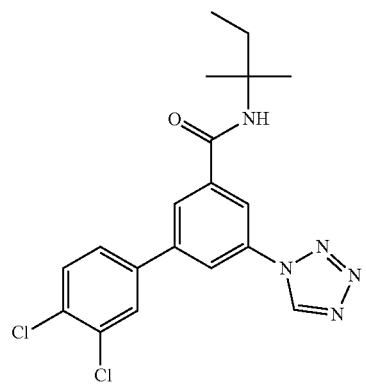 [SMILES: CCC(C)(C)NC(=O)c1cc(-c2ccc(Cl)c(Cl)c2)cc(-n2cnnn2)c1]

The title compound, white solid (59 mg, 58%), MS (ISP) m/z=404.2 [(M+H)$^+$], mp 206° C., was prepared in accordance with the general method of example 7 from 3-iodo-N-tert-pentyl-5-(1H-tetrazol-1-yl)-benzamide (intermediate 3) (96.3 mg, 0.25 mmol) and commercially available 3,4-dichloro-phenylboronic acid (62.0 mg, 325 μmol).

Example 39

3-(3,4-Difluorophenyl)-N-(2-methylbutan-2-yl)-5-(tetrazol-1-yl)-benzamide

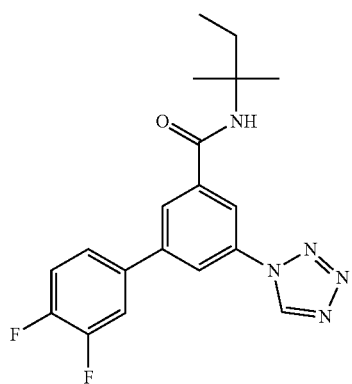

The title compound, white solid (25 mg, 27%), MS (ISP) m/z=372.2 [(M+H)$^+$], mp 189° C., was prepared in accordance with the general method of example 7 from 3-iodo-N-tert-pentyl-5-(1H-tetrazol-1-yl)-benzamide (intermediate 3) (96.3 mg, 0.25 mmol) and commercially available 3,4-difluoro-phenylboronic acid (51.3 mg, 325 μmol).

Example 40

3-(3-Chloro-4-fluorophenyl)-N-(2-methylbutan-2-yl)-5-(tetrazol-1-yl)-benzamide

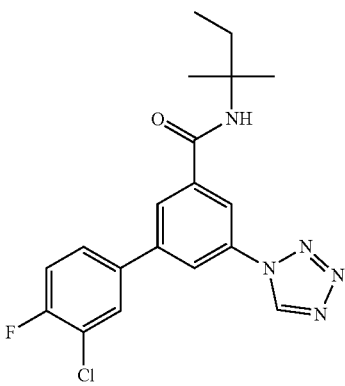 [SMILES: CCC(C)(C)NC(=O)c1cc(-c2ccc(F)c(Cl)c2)cc(-n2cnnn2)c1]

The title compound, white solid (56 mg, 58%), MS (ISP) m/z=388.2 [(M+H)$^+$], mp 205° C., was prepared in accordance with the general method of example 7 from 3-iodo-N-tert-pentyl-5-(1H-tetrazol-1-yl)-benzamide (intermediate 3) (96.3 mg, 0.25 mmol) and commercially available 3-chloro-4-fluoro-phenylboronic acid (56.7 mg, 325 μmol).

Example 41

3-(4-Chlorophenyl)-5-(tetrazol-1-yl)-N-(1,1,1-trifluoro-2-methylpropan-2-yl)-benzamide

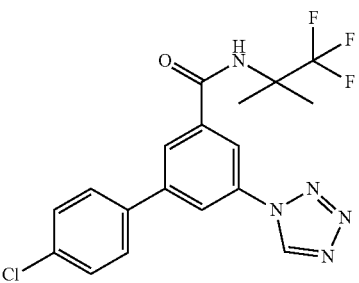 [SMILES: CC(C)(NC(=O)c1cc(-c2ccc(Cl)cc2)cc(-n2cnnn2)c1)C(F)(F)F]

The title compound, white solid (62 mg, 61%), MS (ISP) m/z=410.2 [(M+H)$^+$], mp 187° C., was prepared in accordance with the general method of example 1 from 3-(4-chlorophenyl)-5-(tetrazol-1-yl)-benzoic acid [CAS No. 1138323-00-8] (75.2 mg, 0.25 mmol) and commercially available 1,1,1-trifluoro-2-methylpropan-2-amine (38.9 mg, 0.3 mmol).

Example 42

3-(4-Chlorophenyl)-N-(2-methylbutan-2-yl)-5-(5-propan-2-yltetrazol-1-yl)-benzamide

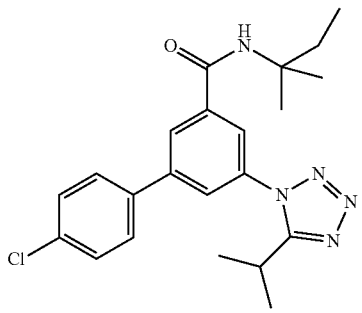 [SMILES: CCC(C)(C)NC(=O)c1cc(-c2ccc(Cl)cc2)cc(-n2nnnc2C(C)C)c1]

The title compound, white foam (80 mg, 78%), MS (ISP) m/z=412.2 [(M+H)$^+$], mp 85° C., was prepared in accordance with the general method of example 1 from 3-(4-chlorophenyl)-5-(5-propan-2-yltetrazol-1-yl)benzoic acid (intermediate 7) (103 mg, 0.30 mmol) and commercially available 2-methylbutan-2-amine (21.8 mg, 29.2 µl, 0.25 mmol).

Example 43

N-tert-Butyl-3-(4-chlorophenyl)-5-(5-propan-2-yltetrazol-1-yl)-benzamide

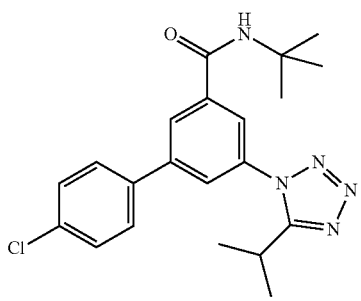 [SMILES: CC(C)c1nnnn1-c1cc(C(=O)NC(C)(C)C)cc(-c2ccc(Cl)cc2)c1]

The title compound, white foam (90 mg, 91%), MS (ISP) m/z=398.3 [(M+H)$^+$], mp 90° C., was prepared in accordance with the general method of example 1 from 3-(4-chlorophenyl)-5-(5-propan-2-yltetrazol-1-yl)benzoic acid (intermediate 7) (103 mg, 0.30 mmol) and commercially available 2-methylpropan-2-amine (18.6 mg, 26.7 µl, 0.25 mmol).

Example 44

3-(4-Chlorophenyl)-N-(2-cyclopropylpropan-2-yl)-5-(5-propan-2-yltetrazol-1-yl)-benzamide

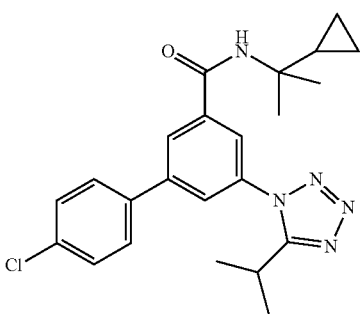 [SMILES: CC(C)c1nnnn1-c1cc(C(=O)NC(C)(C)C2CC2)cc(-c2ccc(Cl)cc2)c1]

The title compound, white foam (100 mg, 94%), MS (ISP) m/z=424.2 [(M+H)$^+$], mp 83° C., was prepared in accordance with the general method of example 1 from 3-(4-chlorophenyl)-5-(5-propan-2-yltetrazol-1-yl)benzoic acid (intermediate 7) (103 mg, 0.30 mmol) and commercially available 2-cyclopropylpropan-2-amine (24.8 mg, 0.25 mmol).

Example 45

(RS)-3-(4-Chlorophenyl)-N-(3-methyl-1,1-dioxothiolan-3-yl)-5-(5-propan-2-yltetrazol-1-yl)benzamide

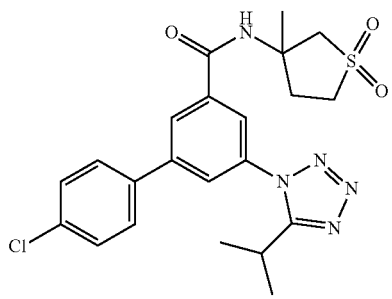 [SMILES: CC(C)c1nnnn1-c1cc(C(=O)NC2(C)CCS(=O)(=O)C2)cc(-c2ccc(Cl)cc2)c1]

The title compound, white foam (110 mg, 93%), MS (ISP) m/z=474.2 [(M+H)$^+$], mp 73° C., was prepared in accordance with the general method of example 1 from 3-(4-chlorophenyl)-5-(5-propan-2-yltetrazol-1-yl)benzoic acid (intermediate 7) (103 mg, 0.30 mmol) and commercially available (RS)-3-amino-3-methyltetrahydrothiophene 1,1-dioxide hydrochloride (46.4 mg, 0.25 mmol).

Example 46

N-(2-Methylbutan-2-yl)-3-(5-propan-2-yltetrazol-1-yl)-5-[4-(trifluoro-methyl)-phenyl]-benzamide

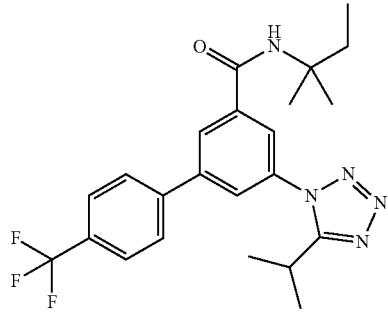 [SMILES: CCC(C)(C)NC(=O)c1cc(-c2ccc(C(F)(F)F)cc2)cc(-n2nnnc2C(C)C)c1]

The title compound, white foam (100 mg, 90%), MS (ISP) m/z=446.3 [(M+H)$^+$], mp 89° C., was prepared in accordance with the general method of example 1 from 3-(5-propan-2-yltetrazol-1-yl)-5-[4-(trifluoromethyl)-phenyl]-benzoic acid (intermediate 8) (113 mg, 0.30 mmol) and commercially available 2-methylbutan-2-amine (21.8 mg, 29.2 µl, 0.25 mmol).

Example 47

N-tert-Butyl-3-(5-propan-2-yltetrazol-1-yl)-5-[4-(trifluoromethyl)-phenyl]-benzamide

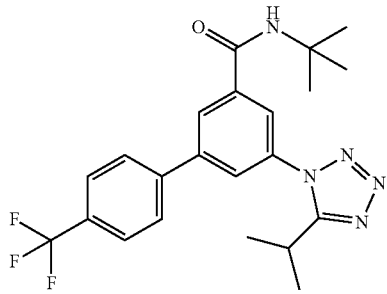 [SMILES: CC(C)c1nnnn1-c1cc(C(=O)NC(C)(C)C)cc(-c2ccc(C(F)(F)F)cc2)c1]

The title compound, white foam (70 mg, 65%), MS (ISP) m/z=432.3 [(M+H)+], mp 92° C., was prepared in accordance with the general method of example 1 from 3-(5-propan-2-yltetrazol-1-yl)-5-[4-(trifluoromethyl)-phenyl]-benzoic acid (intermediate 8) (113 mg, 0.30 mmol) and commercially available 2-methylpropan-2-amine (18.6 mg, 26.7 µl, 0.25 mmol).

Example 48

N-(2-Cyclopropylpropan-2-yl)-3-(5-propan-2-yltetrazol-1-yl)-5-[4-(trifluoromethyl)phenyl]benzamide

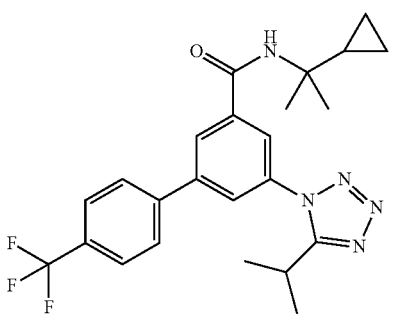 [SMILES: CC(C)c1nnnn1-c1cc(C(=O)NC(C)(C)C2CC2)cc(-c2ccc(C(F)(F)F)cc2)c1]

The title compound, white foam (110 mg, 96%), MS (ISP) m/z=458.3 [(M+H)+], mp 90° C., was prepared in accordance with the general method of example 1 from 3-(5-propan-2-yltetrazol-1-yl)-5-[4-(trifluoromethyl)-phenyl]-benzoic acid (intermediate 8) (113 mg, 0.30 mmol) and commercially available 2-cyclopropylpropan-2-amine (24.8 mg, 0.25 mmol).

Example 49

(RS)—N-(3-methyl-1,1-dioxothiolan-3-yl)-3-(5-propan-2-yltetrazol-1-yl)-5-[4-(trifluoromethyl)phenyl]benzamide

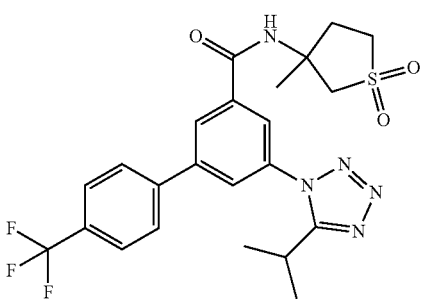 [SMILES: CC(C)c1nnnn1-c1cc(C(=O)NC2(C)CCS(=O)(=O)C2)cc(-c2ccc(C(F)(F)F)cc2)c1]

The title compound, white foam (120 mg, 95%), MS (ISP) m/z=508.3 [(M+H)+], mp 117° C., was prepared in accordance with the general method of example 1 from 3-(5-propan-2-yltetrazol-1-yl)-5-[4-(trifluoromethyl)-phenyl]-benzoic acid (intermediate 8) (113 mg, 0.30 mmol) and commercially available (RS)-3-amino-3-methyltetrahydrothiophene 1,1-dioxide hydrochloride (46.4 mg, 0.25 mmol).

Example 50

3-(4-Chlorophenyl)-N-(1-hydroxy-2-methylpropan-2-yl)-5-(5-propan-2-yltetrazol-1-yl)-benzamide

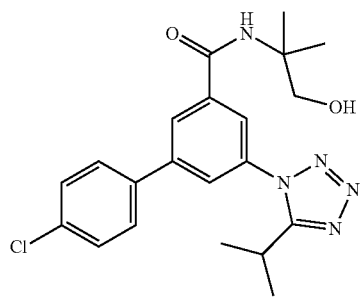 [SMILES: CC(C)c1nnnn1-c1cc(C(=O)NC(C)(C)CO)cc(-c2ccc(Cl)cc2)c1]

The title compound, colorless oil (40 mg, 39%), MS (ISP) m/z=414.3 [(M+H)+], was prepared in accordance with the general method of example 1 from 3-(4-chlorophenyl)-5-(5-propan-2-yltetrazol-1-yl)benzoic acid (intermediate 7) (103 mg, 0.30 mmol) and commercially available 2-amino-2-methylpropan-1-ol (22.3 mg, 24.0 µl, 0.25 mmol).

Example 51

N-(1-Hydroxy-2-methylpropan-2-yl)-3-(5-propan-2-yltetrazol-1-yl)-5-[4-(trifluoromethyl)-phenyl]-benzamide

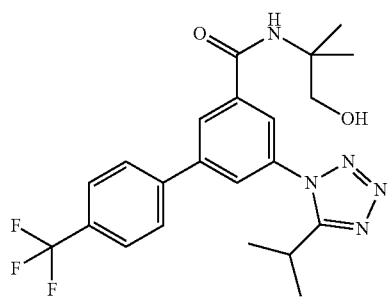 [SMILES: CC(C)c1nnnn1-c1cc(C(=O)NC(C)(C)CO)cc(-c2ccc(C(F)(F)F)cc2)c1]

The title compound, colorless liquid (90 mg, 81%), MS (ISP) m/z=448.3 [(M+H)+], was prepared in accordance with the general method of example 1 from 3-(5-propan-2-yltetrazol-1-yl)-5-[4-(trifluoromethyl)-phenyl]-benzoic acid (intermediate 8) (113 mg, 0.30 mmol) and commercially available 2-amino-2-methylpropan-1-ol (22.3 mg, 24.0 µl, 0.25 mmol).

Example 52

3-(4-Chlorophenyl)-5-(5-propan-2-yltetrazol-1-yl)-N-(1,1,1-trifluoro-2-methylpropan-2-yl)-benzamide

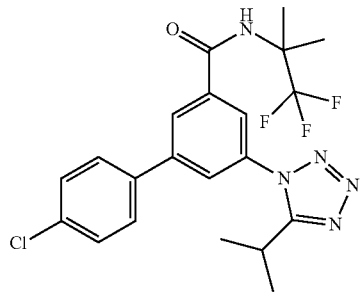 [SMILES: CC(C)c1nnnn1-c1cc(C(=O)NC(C)(C)C(F)(F)F)cc(-c2ccc(Cl)cc2)c1]

The title compound, white foam (100 mg, 89%), MS (ISP) m/z=452.3 [(M+H)$^+$], mp 90° C., was prepared in accordance with the general method of example 1 from 3-(4-chlorophenyl)-5-(5-propan-2-yltetrazol-1-yl)benzoic acid (intermediate 7) (85.7 mg, 0.25 mmol) and commercially available 1,1,1-trifluoro-2-methylpropan-2-amine (38.9 mg, 0.30 mmol).

Example 53

3-(5-Propan-2-yltetrazol-1-yl)-5-[4-(trifluoromethyl)-phenyl]-N-(1,1,1-trifluoro-2-methylpropan-2-yl)-benzamide

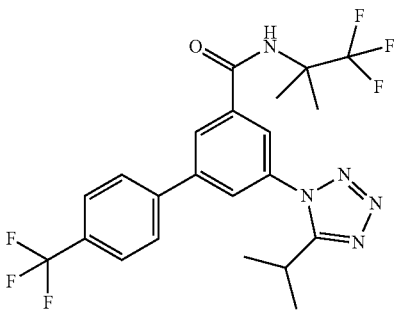 [SMILES: CC(C)c1nnnn1-c1cc(C(=O)NC(C)(C)C(F)(F)F)cc(-c2ccc(C(F)(F)F)cc2)c1]

The title compound, white foam (100 mg, 82%), MS (ISP) m/z=486.3 [(M+H)$^+$], mp 91° C., was prepared in accordance with the general method of example 1 from 3-(5-propan-2-yltetrazol-1-yl)-5-[4-(trifluoromethyl)-phenyl]-benzoic acid (intermediate 8) (94.1 mg, 0.25 mmol) and commercially available 1,1,1-trifluoro-2-methylpropan-2-amine (38.9 mg, 0.30 mmol).

Example 54

3-(4-Chlorophenyl)-5-(5-cyclopropyltetrazol-1-yl)-N-(1,1,1-trifluoro-2-methylpropan-2-yl)-benzamide

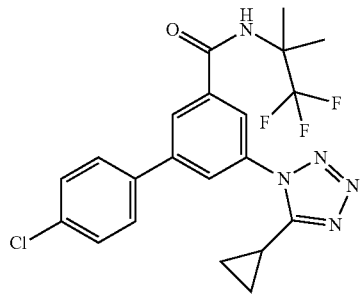 [SMILES: CC(C)(NC(=O)c1cc(-c2ccc(Cl)cc2)cc(-n2nnnc2C2CC2)c1)C(F)(F)F]

The title compound, white foam (100 mg, 89%), MS (ISP) m/z=450.2 [(M+H)$^+$], mp 91.5° C., was prepared in accordance with the general method of example 1 from 3-(4-chlorophenyl)-5-(5-cyclopropyltetrazol-1-yl)-benzoic acid (intermediate 9) (85.2 mg, 0.25 mmol) and commercially available 1,1,1-trifluoro-2-methylpropan-2-amine (38.9 mg, 0.30 mmol).

Example 55

3-(4-Chlorophenyl)-5-(5-cyclopropyltetrazol-1-yl)-N-(2-methylbutan-2-yl)-benzamide

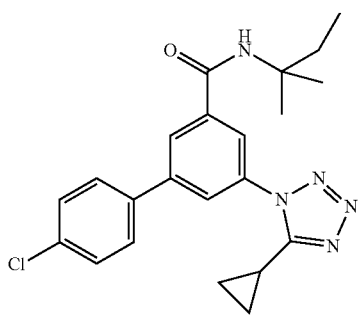 [SMILES: CCC(C)(C)NC(=O)c1cc(-c2ccc(Cl)cc2)cc(-n2nnnc2C2CC2)c1]

The title compound, white foam (80 mg, 78%), MS (ISP) m/z=410.3 [(M+H)$^+$], mp 78° C., was prepared in accordance with the general method of example 1 from 3-(4-chlorophenyl)-5-(5-cyclopropyltetrazol-1-yl)-benzoic acid (intermediate 9) (102 mg, 0.30 mmol) and commercially available 2-methylbutan-2-amine (21.8 mg, 29.2 µl, 0.25 mmol).

Example 56

N-tert-Butyl-3-(4-chlorophenyl)-5-(5-cyclopropyltetrazol-1-yl)-benzamide

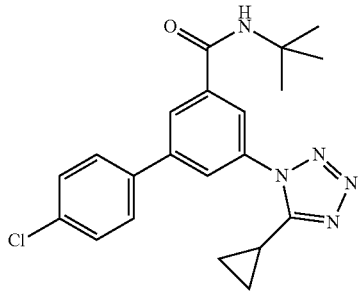 [SMILES: CC(C)(C)NC(=O)c1cc(-c2ccc(Cl)cc2)cc(-n2nnnc2C2CC2)c1]

The title compound, white foam (95 mg, 96%), MS (ISP) m/z=396.2 [(M+H)$^+$], mp 90° C., was prepared in accordance with the general method of example 1 from 3-(4-chlorophenyl)-5-(5-cyclopropyltetrazol-1-yl)-benzoic acid (intermediate 9) (102 mg, 0.30 mmol) and commercially available 2-methylpropan-2-amine (18.6 mg, 26.7 µl, 0.25 mmol).

Example 57

(RS)-3-(4-Chlorophenyl)-5-(5-cyclopropyltetrazol-1-yl)-N-(3-methyl-1,1-dioxothiolan-3-yl)-benzamide

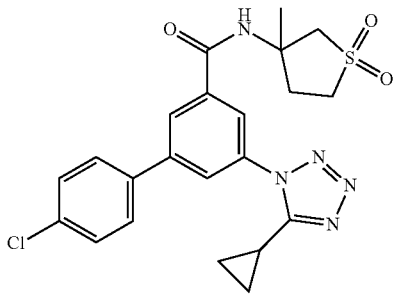 [SMILES: CC1(NC(=O)c2cc(-c3ccc(Cl)cc3)cc(-n3nnnc3C3CC3)c2)CCS(=O)(=O)C1]

The title compound, white foam (110 mg, 93%), MS (ISP) m/z=472.2 [(M+H)$^+$], mp 126° C., was prepared in accordance with the general method of example 1 from 3-(4-chlorophenyl)-5-(5-cyclopropyltetrazol-1-yl)-benzoic acid (intermediate 9) (102 mg, 0.30 mmol) and commercially available (RS)-3-amino-3-methyltetrahydrothiophene 1,1-dioxide hydrochloride (46.4 mg, 0.25 mmol).

Example 58

3-(4-Chlorophenyl)-5-(5-cyclopropyltetrazol-1-yl)-N-(1-hydroxy-2-methylpropan-2-yl)-benzamide

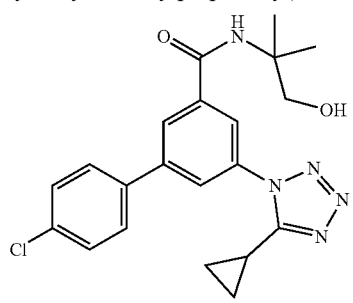

The title compound, white foam (50 mg, 49%), MS (ISP) m/z=412.2 [(M+H)$^+$], mp 110° C., was prepared in accordance with the general method of example 1 from 3-(4-chlorophenyl)-5-(5-cyclopropyltetrazol-1-yl)-benzoic acid (intermediate 9) (102 mg, 0.30 mmol) and commercially available 2-amino-2-methylpropan-1-ol (22.3 mg, 24.0 µl, 0.25 mmol).

Example 59

3-(4-Fluorophenyl)-5-(5-propan-2-yltetrazol-1-yl)-N-(1,1,1-trifluoro-2-methylpropan-2-yl)-benzamide

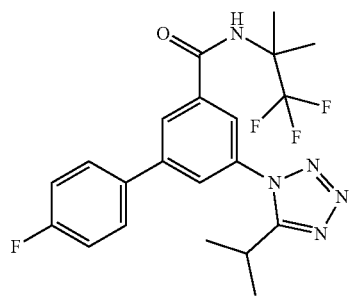 [SMILES: CC(C)c1nnnn1-c1cc(C(=O)NC(C)(C)C(F)(F)F)cc(-c2ccc(F)cc2)c1]

The title compound, white foam (100 mg, 92%), MS (ISP) m/z=436.2 [(M+H)$^+$], mp 80° C., was prepared in accordance with the general method of example 1 from 3-(4-fluorophenyl)-5-(5-propan-2-yltetrazol-1-yl)-benzoic acid (intermediate 10) (81.6 mg, 0.25 mmol) and commercially available 1,1,1-trifluoro-2-methylpropan-2-amine (38.9 mg, 0.30 mmol).

Example 60

3-(4-Fluorophenyl)-N-(2-methylbutan-2-yl)-5-(5-propan-2-yltetrazol-1-yl)-benzamide

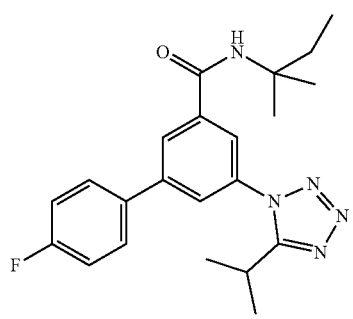

The title compound, white foam (90 mg, 91%), MS (ISP) m/z=396.3 [(M+H)$^+$], mp 69° C., was prepared in accordance with the general method of example 1 from 3-(4-fluorophenyl)-5-(5-propan-2-yltetrazol-1-yl)-benzoic acid (intermediate 10) (97.9 mg, 0.30 mmol) and commercially available 2-methylbutan-2-amine (21.8 mg, 29.2 µl, 0.25 mmol).

Example 61

N-tert-Butyl-3-(4-fluorophenyl)-5-(5-propan-2-yltetrazol-1-yl)-benzamide

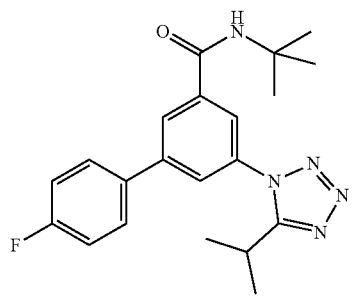 [SMILES: CC(C)c1nnnn1-c1cc(C(=O)NC(C)(C)C)cc(-c2ccc(F)cc2)c1]

The title compound, white foam (70 mg, 73%), MS (ISP) m/z=382.2 [(M+H)$^+$], mp 85° C., was prepared in accordance with the general method of example 1 from 3-(4-fluorophenyl)-5-(5-propan-2-yltetrazol-1-yl)-benzoic acid (intermediate 10) (97.9 mg, 0.30 mmol) and commercially available 2-methylpropan-2-amine (18.6 mg, 26.7 µl, 0.25 mmol).

Example 62

3-(4-Fluorophenyl)-N-(1-hydroxy-2-methylpropan-2-yl)-5-(5-propan-2-yltetrazol-1-yl)-benzamide

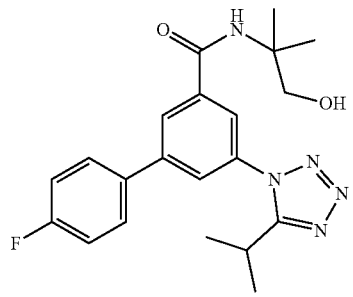 [SMILES: CC(C)c1nnnn1-c1cc(C(=O)NC(C)(C)CO)cc(-c2ccc(F)cc2)c1]

The title compound, white foam (70 mg, 70%), MS (ISP) m/z=398.3 [(M+H)⁺], mp 86.5° C., was prepared in accordance with the general method of example 1 from 3-(4-fluorophenyl)-5-(5-propan-2-yltetrazol-1-yl)-benzoic acid (intermediate 10) (97.9 mg, 0.30 mmol) and commercially available 2-amino-2-methylpropan-1-ol (22.3 mg, 24.0 µl, 0.25 mmol).

Example 63

(RS)-3-(4-Fluorophenyl)-N-(3-methyl-1,1-dioxothiolan-3-yl)-5-(5-propan-2-yltetrazol-1-yl)-benzamide

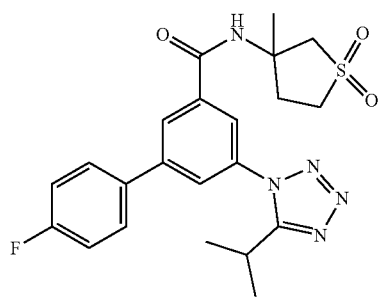 [SMILES: CC(C)c1nnnn1-c1cc(C(=O)NC2(C)CCS(=O)(=O)C2)cc(-c2ccc(F)cc2)c1]

The title compound, white foam (110 mg, 96%), MS (ISP) m/z=458.2 [(M+H)⁺], mp 112.5° C., was prepared in accordance with the general method of example 1 from 3-(4-fluorophenyl)-5-(5-propan-2-yltetrazol-1-yl)-benzoic acid (intermediate 10) (97.9 mg, 0.30 mmol) and commercially available (RS)-3-amino-3-methyltetrahydrothiophene 1,1-dioxide hydrochloride (46.4 mg, 0.25 mmol).

Example 64

3-(4-Chlorophenyl)-N-(1-hydroxy-2-methylpropan-2-yl)-5-(5-methyl-tetrazol-1-yl)-benzamide

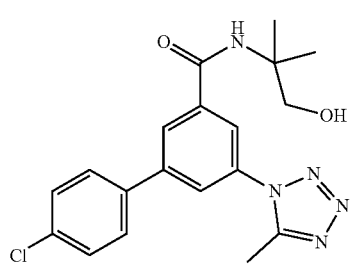 [SMILES: Cc1nnnn1-c1cc(C(=O)NC(C)(C)CO)cc(-c2ccc(Cl)cc2)c1]

The title compound, white solid (60 mg, 62%), MS (ISP) m/z=386.2 [(M+H)⁺], mp 193° C., was prepared in accordance with the general method of example 1 from 3-(4-chlorophenyl)-5-(5-methyltetrazol-1-yl)-benzoic acid (intermediate 13) (86.5 mg, 0.275 mmol) and commercially available 2-amino-2-methylpropan-1-ol (22.3 mg, 24.0 µl, 0.25 mmol).

Example 65

(RS)-3-(4-Chlorophenyl)-N-(3-methyl-1,1-dioxothiolan-3-yl)-5-(5-methyltetrazol-1-yl)-benzamide

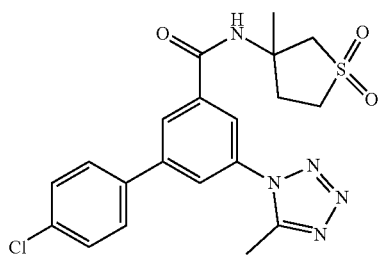 [SMILES: Cc1nnnn1-c1cc(C(=O)NC2(C)CCS(=O)(=O)C2)cc(-c2ccc(Cl)cc2)c1]

The title compound, white foam (90 mg, 81%), MS (ISP) m/z=446.2 [(M+H)⁺], mp 155.5° C., was prepared in accordance with the general method of example 1 from 3-(4-chlorophenyl)-5-(5-methyltetrazol-1-yl)-benzoic acid (intermediate 13) (86.5 mg, 0.275 mmol) and commercially available (RS)-3-amino-3-methyltetrahydrothiophene 1,1-dioxide hydrochloride (46.4 mg, 0.25 mmol).

Example 66

3-(4-Chlorophenyl)-N-(2-methylbutan-2-yl)-5-(5-methyltetrazol-1-yl)-benzamide

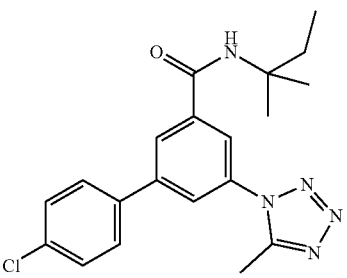 [SMILES: CCC(C)(C)NC(=O)c1cc(-c2ccc(Cl)cc2)cc(-n2nnnc2C)c1]

The title compound, white foam (90 mg, 94%), MS (ISP) m/z=384.2 [(M+H)⁺], mp 80.5° C., was prepared in accordance with the general method of example 1 from 3-(4-chlorophenyl)-5-(5-methyltetrazol-1-yl)-benzoic acid (intermediate 13) (86.5 mg, 0.275 mmol) and commercially available 2-methylbutan-2-amine (21.8 mg, 29.2 µl, 0.25 mmol).

Example 67

N-tert-Butyl-3-(4-chlorophenyl)-5-(5-methyltetrazol-1-yl)-benzamide

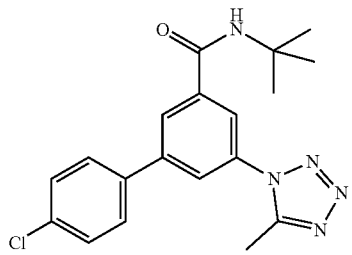 [SMILES: Cc1nnnn1-c1cc(C(=O)NC(C)(C)C)cc(-c2ccc(Cl)cc2)c1]

The title compound, white foam (40 mg, 43%), MS (ISP) m/z=370.2 [(M+H)$^+$], mp 98° C., was prepared in accordance with the general method of example 1 from 3-(4-chlorophenyl)-5-(5-methyltetrazol-1-yl)-benzoic acid (intermediate 13) (86.5 mg, 0.275 mmol) and commercially available 2-methylpropan-2-amine (18.6 mg, 26.7 µl, 0.25 mmol).

Example 68

3-(5-Cyclopropyltetrazol-1-yl)-5-(4-fluorophenyl)-N-(2-methylbutan-2-yl)-benzamide

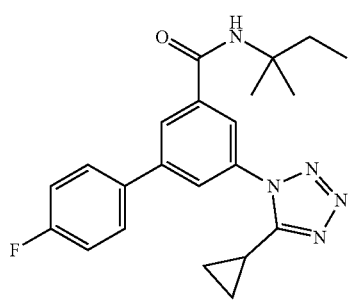 [SMILES: CCC(C)(C)NC(=O)c1cc(-c2ccc(F)cc2)cc(-n2nnnc2C2CC2)c1]

The title compound, white foam (103 mg, 96%), MS (ISP) m/z=394.3 [(M+H)$^+$], mp 74° C., was prepared in accordance with the general method of example 1 from 3-(5-cyclopropyl-tetrazol-1-yl)-5-(4-fluorophenyl)-benzoic acid (intermediate 11) (97.3 mg, 0.30 mmol) and commercially available 2-methylbutan-2-amine (21.8 mg, 29.2 µl, 0.25 mmol).

Example 69

N-tert-Butyl-3-(5-cyclopropyltetrazol-1-yl)-5-(4-fluorophenyl)-benzamide

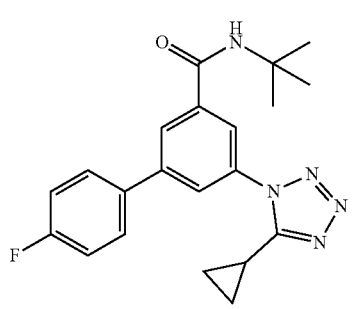 [SMILES: CC(C)(C)NC(=O)c1cc(-c2ccc(F)cc2)cc(-n2nnnc2C2CC2)c1]

The title compound, white foam (30 mg, 32%), MS (ISP) m/z=380.3 [(M+H)$^+$], mp 82° C., was prepared in accordance with the general method of example 1 from 3-(5-cyclopropyl-tetrazol-1-yl)-5-(4-fluorophenyl)-benzoic acid (intermediate 11) (97.3 mg, 0.30 mmol) and commercially available 2-methylpropan-2-amine (18.6 mg, 26.7 µl, 0.25 mmol).

Example 70

3-(4-Chlorophenyl)-5-(5-methyltetrazol-1-yl)-N-(1,1,1-trifluoro-2-methylpropan-2-yl)-benzamide

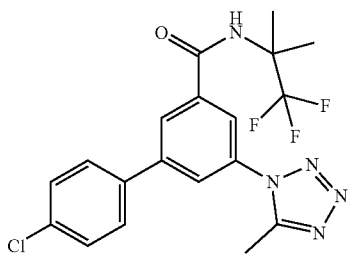 [SMILES: Cc1nnnn1-c1cc(C(=O)NC(C)(C)C(F)(F)F)cc(-c2ccc(Cl)cc2)c1]

The title compound, white foam (90 mg, 85%), MS (ISP) m/z=424.2 [(M+H)$^+$], mp 96° C., was prepared in accordance with the general method of example 1 from 3-(4-chlorophenyl)-5-(5-methyltetrazol-1-yl)-benzoic acid (intermediate 13) (78.7 mg, 0.25 mmol) and commercially available 1,1,1-trifluoro-2-methylpropan-2-amine (38.9 mg, 0.30 mmol).

Example 71

3-(5-Cyclopropyltetrazol-1-yl)-5-(4-fluorophenyl)-N-(1-hydroxy-2-methylpropan-2-yl)-benzamide

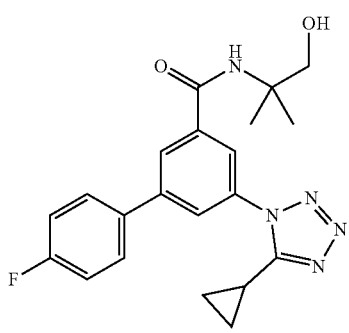 [SMILES: CC(C)(CO)NC(=O)c1cc(-c2ccc(F)cc2)cc(-n2nnnc2C2CC2)c1]

The title compound, white foam (80 mg, 81%), MS (ISP) m/z=396.2 [(M+H)$^+$], mp 80° C., was prepared in accordance with the general method of example 1 from 3-(5-cyclopropyl-tetrazol-1-yl)-5-(4-fluorophenyl)-benzoic acid (intermediate 11) (97.3 mg, 0.30 mmol) and commercially available 2-amino-2-methylpropan-1-ol (22.3 mg, 24.0 µl, 0.25 mmol).

Example 72

N-(2-Cyclopropylpropan-2-yl)-3-(5-cyclopropyltetrazol-1-yl)-5-(4-fluorophenyl)-benzamide

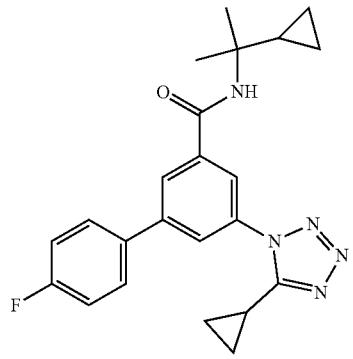 [SMILES: CC(C)(NC(=O)c1cc(-c2ccc(F)cc2)cc(-n2nnnc2C2CC2)c1)C1CC1]

The title compound, white foam (90 mg, 89%), MS (ISP) m/z=406.3 [(M+H)⁺], mp 73° C., was prepared in accordance with the general method of example 1 from 3-(5-cyclopropyl-tetrazol-1-yl)-5-(4-fluorophenyl)-benzoic acid (intermediate 11) (97.3 mg, 0.30 mmol) and commercially available 2-cyclopropylpropan-2-amine hydrochloride (33.9 mg, 0.25 mmol).

Example 73

3-(5-Cyclopropyltetrazol-1-yl)-5-(4-fluorophenyl)-N-(1,1,1-trifluoro-2-methylpropan-2-yl)-benzamide

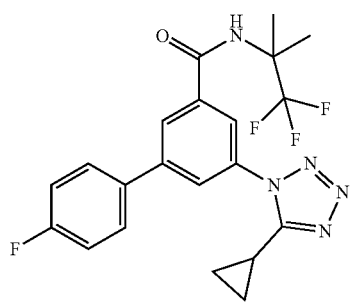 [SMILES: CC(C)(NC(=O)c1cc(-c2ccc(F)cc2)cc(-n2nnnc2C2CC2)c1)C(F)(F)F]

The title compound, white foam (30 mg, 28%), MS (ISP) m/z=434.3 [(M+H)⁺], mp 81° C., was prepared in accordance with the general method of example 1 from 3-(5-cyclopropyl-tetrazol-1-yl)-5-(4-fluorophenyl)-benzoic acid (intermediate 11) (81.1 mg, 0.25 mmol) and commercially available 1,1,1-trifluoro-2-methylpropan-2-amine (38.9 mg, 0.30 mmol).

Example 74

3-(4-Chlorophenyl)-N-(2-methylbutan-2-yl)-5-[5-(trifluoromethyl)-tetrazol-1-yl]-benzamide

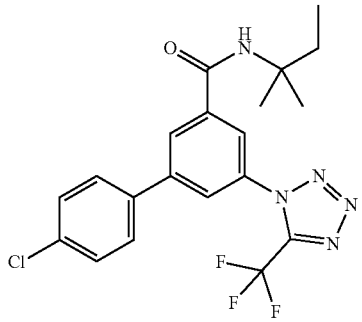 [SMILES: CCC(C)(C)NC(=O)c1cc(-c2ccc(Cl)cc2)cc(-n2nnnc2C(F)(F)F)c1]

The title compound, white solid (80 mg, 73%), MS (ISP) m/z=438.2 [(M+H)⁺], mp 185° C., was prepared in accordance with the general method of example 1 from 3-(4-chlorophenyl)-5-[5-(trifluoromethyl)-tetrazol-1-yl]-benzoic acid (intermediate 14) (101 mg, 0.275 mmol) and commercially available 2-methylbutan-2-amine (21.8 mg, 29.2 μl, 0.25 mmol).

Example 75

N-tert-Butyl-3-(4-chlorophenyl)-5-[5-(trifluoromethyl)-tetrazol-1-yl]-benzamide

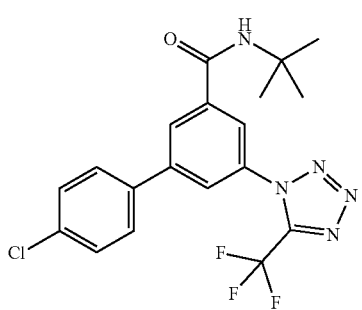 [SMILES: CC(C)(C)NC(=O)c1cc(-c2ccc(Cl)cc2)cc(-n2nnnc2C(F)(F)F)c1]

The title compound, white solid (90 mg, 85%), MS (ISP) m/z=424.3 [(M+H)⁺], mp 186° C., was prepared in accordance with the general method of example 1 from 3-(4-chlorophenyl)-5-[5-(trifluoromethyl)-tetrazol-1-yl]-benzoic acid (intermediate 14) (101 mg, 0.275 mmol) and commercially available 2-methylpropan-2-amine (18.6 mg, 26.7 μl, 0.25 mmol).

Example 76

3-(4-Chlorophenyl)-N-(1-hydroxy-2-methylpropan-2-yl)-5-[5-(trifluoromethyl)-tetrazol-1-yl]-benzamide

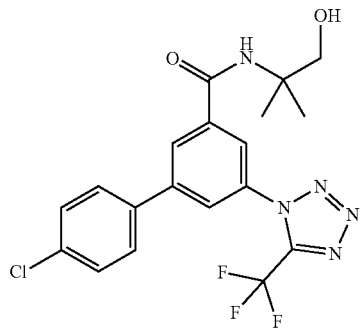 [SMILES: CC(C)(CO)NC(=O)c1cc(-c2ccc(Cl)cc2)cc(-n2nnnc2C(F)(F)F)c1]

The title compound, white foam (80 mg, 73%), MS (ISP) m/z=440.2 [(M+H)⁺], mp 89° C., was prepared in accordance with the general method of example 1 from 3-(4-chlorophenyl)-5-[5-(trifluoromethyl)-tetrazol-1-yl]-benzoic acid (intermediate 14) (101 mg, 0.275 mmol) and commercially available 2-amino-2-methylpropan-1-ol (22.3 mg, 24.0 µl, 0.25 mmol).

Example 77

(RS)-3-(5-Cyclopropyltetrazol-1-yl)-5-(4-fluorophenyl)-N-(3-methyl-1,1-dioxothiolan-3-yl)-benzamide

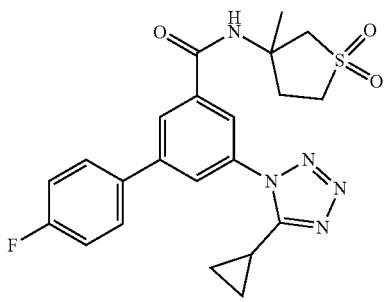 [SMILES: CC1(NC(=O)c2cc(-c3ccc(F)cc3)cc(-n3nnnc3C3CC3)c2)CCS(=O)(=O)C1]

The title compound, white foam (110 mg, 97%), MS (ISP) m/z=456.3 [(M+H)⁺], mp 120° C., was prepared in accordance with the general method of example 1 from 3-(5-cyclopropyl-tetrazol-1-yl)-5-(4-fluorophenyl)-benzoic acid (intermediate 11) (97.3 mg, 0.30 mmol) and commercially available (RS)-3-amino-3-methyltetrahydrothiophene 1,1-dioxide hydrochloride (46.4 mg, 0.25 mmol).

Example 78

3-(4-Fluorophenyl)-N-(2-methylbutan-2-yl)-5-(5-methyltetrazol-1-yl)-benzamide

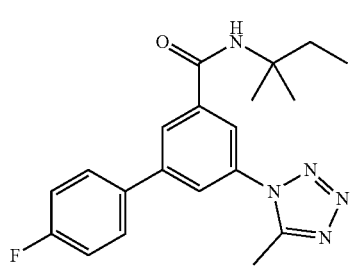 [SMILES: CCC(C)(C)NC(=O)c1cc(-c2ccc(F)cc2)cc(-n2nnnc2C)c1]

The title compound, white foam (80 mg, 87%), MS (ISP) m/z=368.3 [(M+H)⁺], mp 83° C., was prepared in accordance with the general method of example 1 from 3-(4-fluorophenyl)-5-(5-methyltetrazol-1-yl)-benzoic acid (intermediate 12) (89.5 mg, 0.30 mmol) and commercially available 2-methylbutan-2-amine (21.8 mg, 29.2 µl, 0.25 mmol).

Example 79

3-(4-Chlorophenyl)-N-(1,1,1-trifluoro-2-methylpropan-2-yl)-5-[5-(trifluoromethyl)tetrazol-1-yl]-benzamide

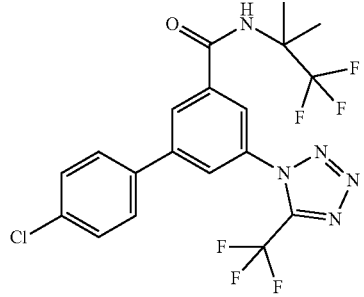 [SMILES: CC(C)(NC(=O)c1cc(-c2ccc(Cl)cc2)cc(-n2nnnc2C(F)(F)F)c1)C(F)(F)F]

The title compound, white solid (100 mg, 84%), MS (ISP) m/z=478.2 [(M+H)⁺], mp 166.5° C., was prepared in accordance with the general method of example 1 from 3-(4-chlorophenyl)-5-[5-(trifluoromethyl)-tetrazol-1-yl]-benzoic acid (intermediate 14) (92.2 mg, 0.25 mmol) and commercially available 1,1,1-trifluoro-2-methylpropan-2-amine (38.9 mg, 0.30 mmol).

Example 80

N-tert-Butyl-3-(4-fluorophenyl)-5-(5-methyltetrazol-1-yl)-benzamide

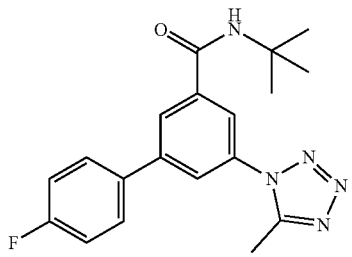 [SMILES: Cc1nnnn1-c1cc(C(=O)NC(C)(C)C)cc(-c2ccc(F)cc2)c1]

The title compound, white foam (84 mg, %), MS (ISP) m/z=354.2 [(M+H)⁺], mp 80° C., was prepared in accordance with the general method of example 1 from 3-(4-fluorophenyl)-5-(5-methyltetrazol-1-yl)-benzoic acid (intermediate 12) (89.5 mg, 0.30 mmol) and commercially available 2-methylpropan-2-amine (18.6 mg, 26.7 µl, 0.25 mmol).

Example 81

3-(4-Chlorophenyl)-N-(2-cyclopropylpropan-2-yl)-5-(5-cyclopropyl-tetrazol-1-yl)-benzamide

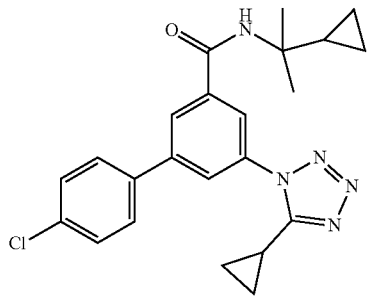 [SMILES: CC(C)(NC(=O)c1cc(-c2ccc(Cl)cc2)cc(-n2nnnc2C2CC2)c1)C1CC1]

The title compound, white foam (90 mg, 85%), MS (ISP) m/z=422.2 [(M+H)$^+$], mp 95° C., was prepared in accordance with the general method of example 1 from 3-(4-chlorophenyl)-5-(5-cyclopropyltetrazol-1-yl)-benzoic acid (intermediate 9) (102 mg, 0.30 mmol) and commercially available 2-cyclopropylpropan-2-amine hydrochloride (33.9 mg, 0.25 mmol).

Example 82

N-(2-Cyclopropylpropan-2-yl)-3-(4-fluorophenyl)-5-(5-propan-2-yltetrazol-1-yl)-benzamide

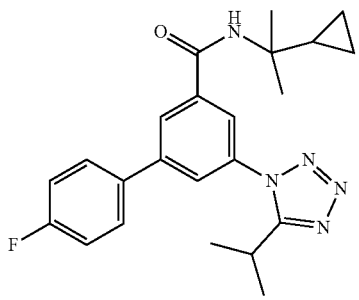 [SMILES: CC(C)c1nnnn1-c1cc(C(=O)NC(C)(C)C2CC2)cc(-c2ccc(F)cc2)c1]

The title compound, white foam (100 mg, 98%), MS (ISP) m/z=408.3 [(M+H)$^+$], mp 75° C., was prepared in accordance with the general method of example 1 from 3-(4-fluorophenyl)-5-(5-propan-2-yltetrazol-1-yl)-benzoic acid (intermediate 10) (97.9 mg, 0.30 mmol) and commercially available 2-cyclopropylpropan-2-amine hydrochloride (33.9 mg, 0.25 mmol).

Example 83

3-(4-Chlorophenyl)-N-(2-cyclopropylpropan-2-yl)-5-(5-methyltetrazol-1-yl)-benzamide

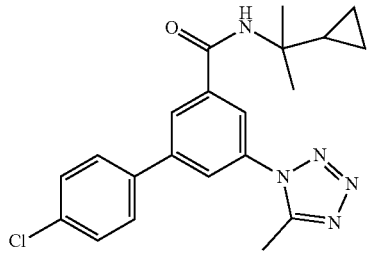 [SMILES: Cc1nnnn1-c1cc(C(=O)NC(C)(C)C2CC2)cc(-c2ccc(Cl)cc2)c1]

The title compound, white solid (90 mg, 91%), MS (ISP) m/z=396.2 [(M+H)$^+$], mp 85° C., was prepared in accordance with the general method of example 1 from 3-(4-chlorophenyl)-5-(5-methyltetrazol-1-yl)-benzoic acid (intermediate 13) (94.4 mg, 0.30 mmol) and commercially available 2-cyclopropylpropan-2-amine hydrochloride (33.9 mg, 0.25 mmol).

Example 84

3-(4-Fluorophenyl)-N-(1-hydroxy-2-methylpropan-2-yl)-5-(5-methyltetrazol-1-yl)-benzamide

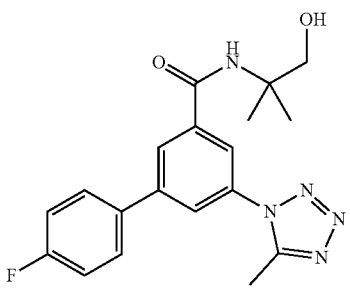 [SMILES: Cc1nnnn1-c1cc(C(=O)NC(C)(C)CO)cc(-c2ccc(F)cc2)c1]

The title compound, white foam (50 mg, 54%), MS (ISP) m/z=370.2 [(M+H)$^+$], mp 85° C., was prepared in accordance with the general method of example 1 from 3-(4-fluorophenyl)-5-(5-methyltetrazol-1-yl)-benzoic acid (intermediate 12) (89.5 mg, 0.30 mmol) and commercially available 2-amino-2-methylpropan-1-ol (22.3 mg, 24.0 µl, 0.25 mmol).

Example 85

N-(2-Cyclopropylpropan-2-yl)-3-(4-fluorophenyl)-5-(5-methyltetrazol-1-yl)-benzamide

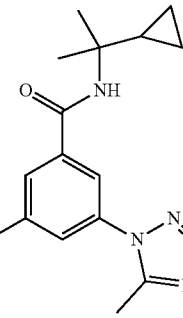

The title compound, white foam (94.3 mg, 99%), MS (ISP) m/z=380.2 [(M+H)$^+$], mp 78° C., was prepared in accordance with the general method of example 1 from 3-(4-fluorophenyl)-5-(5-methyltetrazol-1-yl)-benzoic acid (intermediate 12) (89.5 mg, 0.30 mmol) and commercially available 2-cyclopropylpropan-2-amine hydrochloride (33.9 mg, 0.25 mmol).

Example 86

3-(4-Fluorophenyl)-5-(5-methyltetrazol-1-yl)-N-(1,1,1-trifluoro-2-methylpropan-2-yl)-benzamide

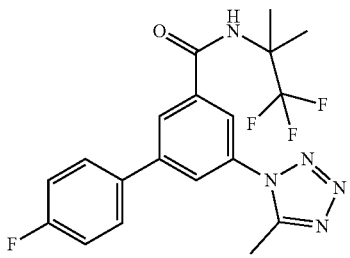 [SMILES: Cc1nnnn1-c1cc(C(=O)NC(C)(C)C(F)(F)F)cc(-c2ccc(F)cc2)c1]

The title compound, white foam (90 mg, 88%), MS (ISP) m/z=408.2 [(M+H)⁺], mp 86° C., was prepared in accordance with the general method of example 1 from 3-(4-fluorophenyl)-5-(5-methyltetrazol-1-yl)-benzoic acid (intermediate 12) (74.6 mg, 0.25 mmol) and commercially available 1,1,1-trifluoro-2-methylpropan-2-amine (38.9 mg, 0.30 mmol).

Example 87

(RS)-3-(4-Fluorophenyl)-N-(3-methyl-1,1-dioxothiolan-3-yl)-5-(5-methyltetrazol-1-yl)-benzamide

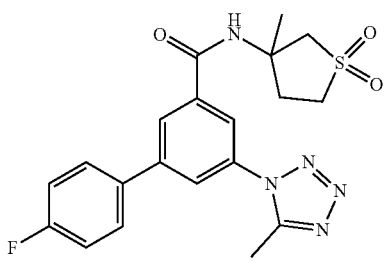 [SMILES: Cc1nnnn1-c1cc(C(=O)NC2(C)CCS(=O)(=O)C2)cc(-c2ccc(F)cc2)c1]

The title compound, white foam (100 mg, 93%), MS (ISP) m/z=430.2 [(M+H)⁺], mp 117° C., was prepared in accordance with the general method of example 1 from 3-(4-fluorophenyl)-5-(5-methyltetrazol-1-yl)-benzoic acid (intermediate 12) (89.5 mg, 0.30 mmol) and commercially available (RS)-3-amino-3-methyltetrahydrothiophene 1,1-dioxide hydrochloride (46.4 mg, 0.25 mmol).

Example 88

3-(5-tert-Butyltetrazol-1-yl)-5-(4-chlorophenyl)-N-(1-hydroxy-2-methylpropan-2-yl)-benzamide

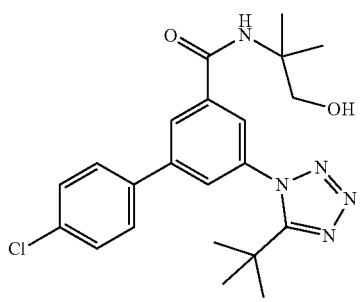 [SMILES: CC(C)(CO)NC(=O)c1cc(-c2ccc(Cl)cc2)cc(-n2nnnc2C(C)(C)C)c1]

The title compound, white foam (100 mg, 94%), MS (ISP) m/z=428.2 [(M+H)⁺], mp 112° C., was prepared in accordance with the general method of example 1 from 3-(5-tert-butyl-tetrazol-1-yl)-5-(4-chlorophenyl)-benzoic acid (intermediate 15) (98.1 mg, 0.30 mmol) and commercially available 2-amino-2-methylpropan-1-ol (22.3 mg, 24.0 µl, 0.25 mmol).

Example 89

(RS)-3-(5-tert-Butyltetrazol-1-yl)-5-(4-chlorophenyl)-N-(3-methyl-, 1-dioxothiolan-3-yl)benzamide

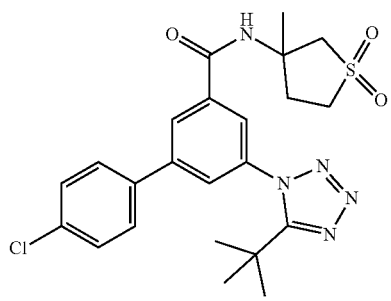 [SMILES: CC1(NC(=O)c2cc(-c3ccc(Cl)cc3)cc(-n3nnnc3C(C)(C)C)c2)CCS(=O)(=O)C1]

The title compound, white solid (80 mg, 66%), MS (ISP) m/z=488.2 [(M+H)⁺], mp 187° C., was prepared in accordance with the general method of example 1 from 3-(5-tert-butyl-tetrazol-1-yl)-5-(4-chlorophenyl)-benzoic acid (intermediate 15) (98.1 mg, 0.30 mmol) and commercially available (RS)-3-amino-3-methyltetrahydrothiophene 1,1-dioxide hydrochloride (46.4 mg, 0.25 mmol).

Example 90

3-(5-tert-Butyltetrazol-1-yl)-5-(4-chlorophenyl)-N-(2-methylbutan-2-yl)-benzamide

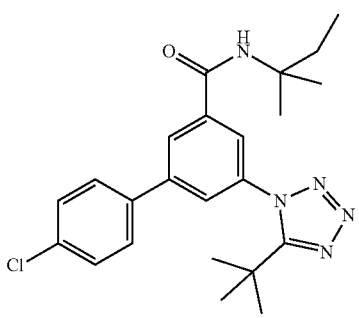 [SMILES: CCC(C)(C)NC(=O)c1cc(-c2ccc(Cl)cc2)cc(-n2nnnc2C(C)(C)C)c1]

The title compound, white foam (100 mg, 94%), MS (ISP) m/z=426.3 [(M+H)⁺], mp 119° C., was prepared in accordance with the general method of example 1 from 3-(5-tert-butyl-tetrazol-1-yl)-5-(4-chlorophenyl)-benzoic acid (intermediate 15) (98.1 mg, 0.30 mmol) and commercially available 2-methylbutan-2-amine (21.8 mg, 29.2 µl, 0.25 mmol).

Example 91

N-tert-Butyl-3-(5-tert-butyltetrazol-1-yl)-5-(4-chlorophenyl)-benzamide

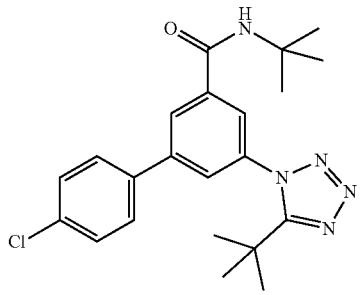 [SMILES: CC(C)(C)NC(=O)c1cc(-c2ccc(Cl)cc2)cc(-n2nnnc2C(C)(C)C)c1]

The title compound, white solid (70 mg, 68%), MS (ISP) m/z=412.3 [(M+H)+], mp 230.5° C., was prepared in accordance with the general method of example 1 from 3-(5-tert-butyl-tetrazol-1-yl)-5-(4-chlorophenyl)-benzoic acid (intermediate 15) (98.1 mg, 0.30 mmol) and commercially available 2-methylpropan-2-amine (18.6 mg, 26.7 µl, 0.25 mmol).

Example 92

3-(5-tert-Butyltetrazol-1-yl)-5-(4-chlorophenyl)-N-(2-cyclopropylpropan-2-yl)-benzamide

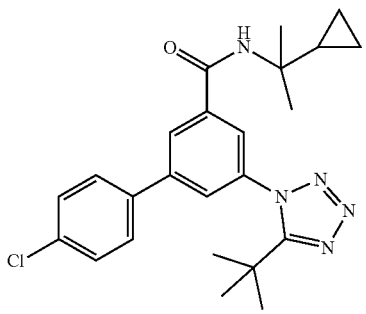 [SMILES: CC(C)(C)c1nnnn1-c1cc(C(=O)NC(C)(C)C2CC2)cc(-c2ccc(Cl)cc2)c1]

The title compound, white foam (100 mg, 91%), MS (ISP) m/z=438.2 [(M+H)+], mp 101° C., was prepared in accordance with the general method of example 1 from 3-(5-tert-butyl-tetrazol-1-yl)-5-(4-chlorophenyl)-benzoic acid (intermediate 15) (98.1 mg, 0.30 mmol) and commercially available 2-cyclopropylpropan-2-amine hydrochloride (33.9 mg, 0.25 mmol).

Example 93

3-(5-tert-Butyltetrazol-1-yl)-5-(4-chlorophenyl)-N-(1,1,1-trifluoro-2-methylpropan-2-yl)-benzamide

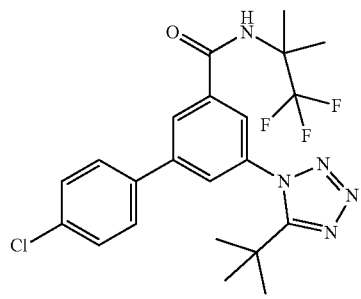 [SMILES: CC(C)(C)c1nnnn1-c1cc(C(=O)NC(C)(C)C(F)(F)F)cc(-c2ccc(Cl)cc2)c1]

The title compound, white solid (110 mg, 94%), MS (ISP) m/z=466.2 [(M+H)+], mp 218.5° C., was prepared in accordance with the general method of example 1 from 3-(5-tert-butyl-tetrazol-1-yl)-5-(4-chlorophenyl)-benzoic acid (intermediate 15) (89.2 mg, 0.25 mmol) and commercially available 1,1,1-trifluoro-2-methylpropan-2-amine (38.9 mg, 0.30 mmol).

Example 94

3-(5-tert-Butyltetrazol-1-yl)-5-(4-fluorophenyl)-N-(1-hydroxy-2-methylpropan-2-yl)-benzamide

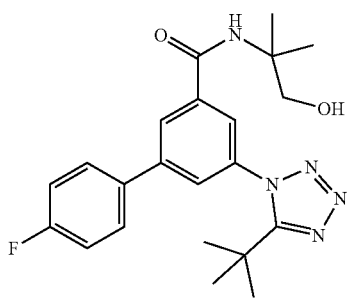 [SMILES: CC(C)(CO)NC(=O)c1cc(-c2ccc(F)cc2)cc(-n2nnnc2C(C)(C)C)c1]

The title compound, white solid (100 mg, 97%), MS (ISP) m/z=412.3 [(M+H)+], mp 212° C., was prepared in accordance with the general method of example 1 from 3-(5-tert-butyl-tetrazol-1-yl)-5-(4-fluorophenyl)-benzoic acid (intermediate 16) (102 mg, 0.30 mmol) and commercially available 2-amino-2-methylpropan-1-ol (22.3 mg, 24.0 µl, 0.25 mmol).

Example 95

(RS)-3-(5-tert-Butyltetrazol-1-yl)-5-(4-fluorophenyl)-N-(3-methyl-,1-dioxothiolan-3-yl)-benzamide The title compound, white solid (100 mg, 85%), MS (ISP) m/z=472.2 [(M+H)+], mp 258.5° C., was prepared in accordance with the general method of example 1 from 3-(5-tert-butyl-tetrazol-1-yl)-5-(4-fluorophenyl)-benzoic acid (intermediate 16) (102 mg, 0.30 mmol) and commercially available (RS)-3-amino-3-methyltetrahydrothiophene 1,1-dioxide hydrochloride (46.4 mg, 0.25 mmol).

Example 96

3-(5-tert-Butyltetrazol-1-yl)-5-(4-fluorophenyl)-N-(1,1,1-trifluoro-2-methylpropan-2-yl)-benzamide

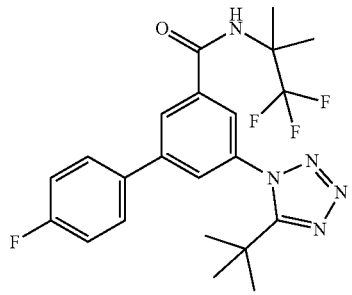 [SMILES: CC(C)(C)c1nnnn1-c1cc(C(=O)NC(C)(C)C(F)(F)F)cc(-c2ccc(F)cc2)c1]

The title compound, white solid (110 mg, 98%), MS (ISP) m/z=450.2 [(M+H)+], mp 224.5° C., was prepared in accordance with the general method of example 1 from 3-(5-tert-butyl-tetrazol-1-yl)-5-(4-fluorophenyl)-benzoic acid (intermediate 16) (85.1 mg, 0.25 mmol) and commercially available 1,1,1-trifluoro-2-methylpropan-2-amine (38.9 mg, 0.30 mmol).

Example 97

3-(5-tert-Butyltetrazol-1-yl)-5-(4-fluorophenyl)-N-(2-methylbutan-2-yl)-benzamide

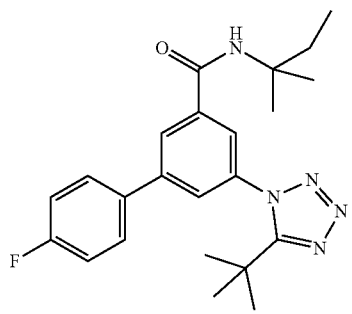 [SMILES: CCC(C)(C)NC(=O)c1cc(-c2ccc(F)cc2)cc(-n2nnnc2C(C)(C)C)c1]

The title compound, white solid (90 mg, 88%), MS (ISP) m/z=410.3 [(M+H)+], mp 199° C., was prepared in accordance with the general method of example 1 from 3-(5-tert-butyl-tetrazol-1-yl)-5-(4-fluorophenyl)-benzoic acid (intermediate 16) (102 mg, 0.30 mmol) and commercially available 2-methylbutan-2-amine (21.8 mg, 29.2 µl, 0.25 mmol).

Example 98

N-tert-Butyl-3-(5-tert-butyltetrazol-1-yl)-5-(4-fluorophenyl)-benzamide

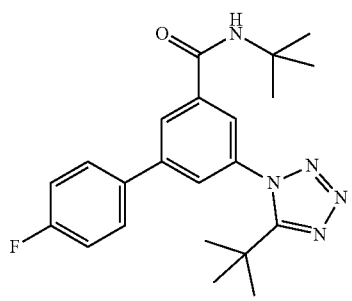 [SMILES: CC(C)(C)NC(=O)c1cc(-c2ccc(F)cc2)cc(-n2nnnc2C(C)(C)C)c1]

The title compound, white solid (98 mg, 99%), MS (ISP) m/z=396.2 [(M+H)+], mp 223.5° C., was prepared in accordance with the general method of example 1 from 3-(5-tert-butyl-tetrazol-1-yl)-5-(4-fluorophenyl)-benzoic acid (intermediate 16) (102 mg, 0.30 mmol) and commercially available 2-methylpropan-2-amine (18.6 mg, 26.7 µl, 0.25 mmol).

Example 99

3-(5-tert-Butyltetrazol-1-yl)-N-(2-cyclopropylpropan-2-yl)-5-(4-fluorophenyl)-benzamide

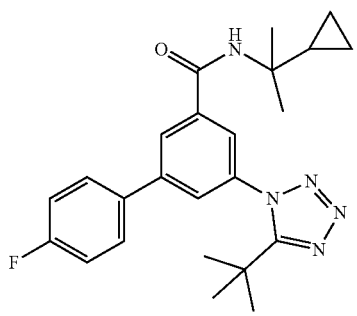 [SMILES: CC(C)(C)c1nnnn1-c1cc(C(=O)NC(C)(C)C2CC2)cc(-c2ccc(F)cc2)c1]

The title compound, white solid (100 mg, 95%), MS (ISP) m/z=422.3 [(M+H)+], mp 201° C., was prepared in accordance with the general method of example 1 from 3-(5-tert-butyl-tetrazol-1-yl)-5-(4-fluorophenyl)-benzoic acid (intermediate 16) (102 mg, 0.30 mmol) and commercially available 2-cyclopropylpropan-2-amine hydrochloride (33.9 mg, 0.25 mmol).

Example 100

3-(5-tert-Butyltetrazol-1-yl)-N-(2-cyanopropan-2-yl)-5-(4-fluorophenyl)-benzamide

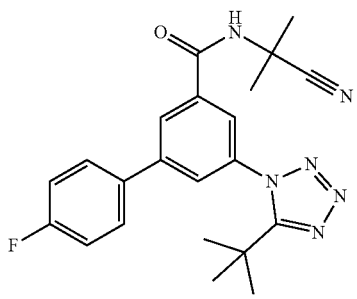 [SMILES: CC(C)(C#N)NC(=O)c1cc(-c2ccc(F)cc2)cc(-n2nnnc2C(C)(C)C)c1]

The title compound, off-white foam (30 mg, 30%), MS (ISP) m/z=407.2 [(M+H)+], mp 115° C., was prepared in accordance with the general method of example 1 from 3-(5-tert-butyl-tetrazol-1-yl)-5-(4-fluorophenyl)-benzoic acid (intermediate 16) (102 mg, 0.30 mmol) and commercially available 2-amino-2-methyl-propanenitrile (21.0 mg, 0.25 mmol).

Example 101

3-(4-Chlorophenyl)-N-(2-cyanopropan-2-yl)-5-(5-propan-2-yltetrazol-1-yl)-benzamide

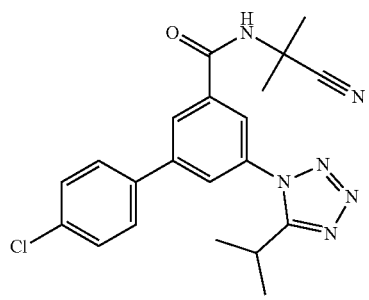 [SMILES: CC(C)c1nnnn1-c1cc(C(=O)NC(C)(C)C#N)cc(-c2ccc(Cl)cc2)c1]

The title compound, off-white foam (30 mg, 29%), MS (ISP) m/z=409.2 [(M+H)+], mp 107° C., was prepared in accordance with the general method of example 1 from 3-(4-chlorophenyl)-5-(5-propan-2-yltetrazol-1-yl)-benzoic acid (intermediate 7) (103 mg, 0.30 mmol) and commercially available 2-amino-2-methyl-propanenitrile (21.0 mg, 0.25 mmol).

Example 102

N-tert-Butyl-3-(5-tert-butyltetrazol-1-yl)-5-(4-methylphenyl)-benzamide

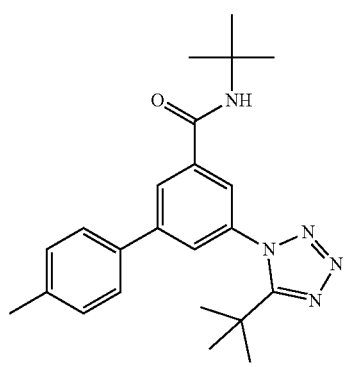 [SMILES: Cc1ccc(-c2cc(C(=O)NC(C)(C)C)cc(-n3nnnc3C(C)(C)C)c2)cc1]

The title compound, white solid (98 mg, 100%), MS (ISP) m/z=392.3 [(M+H)+], mp 222° C., was prepared in accordance with the general method of example 7 from 3-bromo-N-tert-butyl-5-(5-tert-butyltetrazol-1-yl)-benzamide (intermediate 17) (95.1 mg, 0.25 mmol) and commercially available 4-methylphenylboronic acid (44.2 mg, 325 μmol).

Example 103

N-tert-Butyl-3-(5-tert-butyltetrazol-1-yl)-5-(4-fluoro-3-methylphenyl)-benzamide

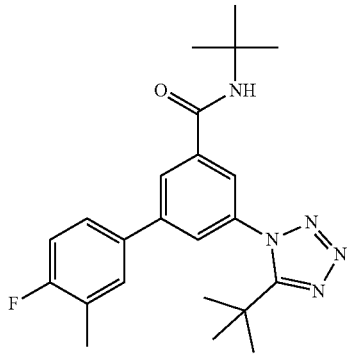 [SMILES: Cc1cc(-c2cc(C(=O)NC(C)(C)C)cc(-n3nnnc3C(C)(C)C)c2)ccc1F]

The title compound, white foam (90 mg, 88%), MS (ISP) m/z=410.3 [(M+H)+], mp 190.5° C., was prepared in accordance with the general method of example 7 from 3-bromo-N-tert-butyl-5-(5-tert-butyltetrazol-1-yl)-benzamide (intermediate 17) (95.1 mg, 0.25 mmol) and commercially available 4-fluoro-3-methyl-phenylboronic acid (50.0 mg, 325 μmol).

Example 104

N-tert-Butyl-3-(5-tert-butyltetrazol-1-yl)-5-[4-(trifluoromethyl)-phenyl]-benzamide

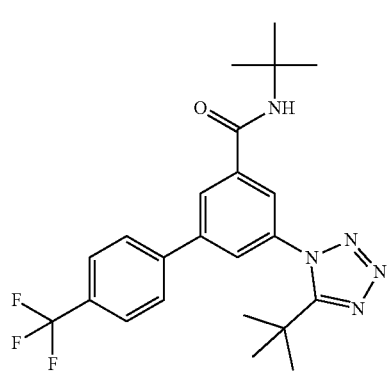 [SMILES: CC(C)(C)NC(=O)c1cc(-c2ccc(C(F)(F)F)cc2)cc(-n2nnnc2C(C)(C)C)c1]

The title compound, white solid (100 mg, 90%), MS (ISP) m/z=446.3 [(M+H)+], mp 241° C., was prepared in accordance with the general method of example 7 from 3-bromo-N-tert-butyl-5-(5-tert-butyltetrazol-1-yl)-benzamide (intermediate 17) (95.1 mg, 0.25 mmol) and commercially available 4-trifluoromethyl-phenylboronic acid (61.7 mg, 325 μmol).

Example 105

N-tert-Butyl-3-(5-tert-butyltetrazol-1-yl)-5-(4-chloro-3-fluorophenyl)-benzamide

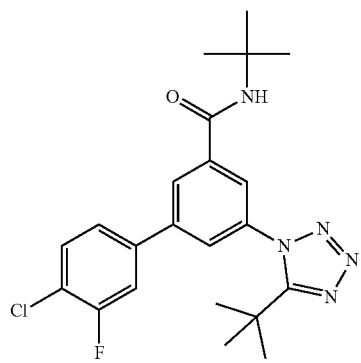 [SMILES: CC(C)(C)NC(=O)c1cc(-c2ccc(Cl)c(F)c2)cc(-n2nnnc2C(C)(C)C)c1]

The title compound, white solid (70 mg, 65%), MS (ISP) m/z=430.2 [(M+H)⁺], mp 240.5° C., was prepared in accordance with the general method of example 7 from 3-bromo-N-tert-butyl-5-(5-tert-butyltetrazol-1-yl)-benzamide (intermediate 17) (95.1 mg, 0.25 mmol) and commercially available 4-chloro-3-fluoro-phenylboronic acid (56.7 mg, 325 μmol).

Example 106

N-tert-Butyl-3-(5-tert-butyltetrazol-1-yl)-5-(3,4-difluorophenyl)-benzamide

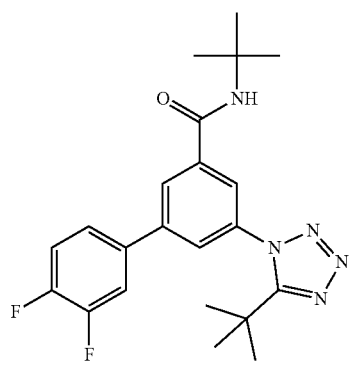

The title compound, white solid (100 mg, 97%), MS (ISP) m/z=414.3 [(M+H)⁺], mp 225.5° C., was prepared in accordance with the general method of example 7 from 3-bromo-N-tert-butyl-5-(5-tert-butyltetrazol-1-yl)-benzamide (intermediate 17) (95.1 mg, 0.25 mmol) and commercially available 3,4-difluoro-phenylboronic acid (51.3 mg, 325 μmol).

Example 107

N-tert-Butyl-3-(5-tert-butyltetrazol-1-yl)-5-(4-cyclopropylphenyl)-benzamide

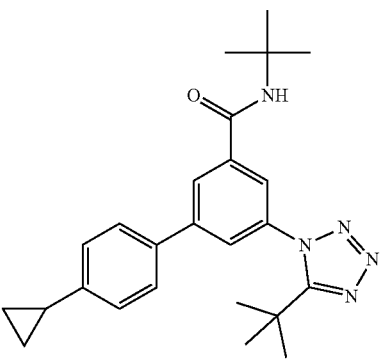 [SMILES: CC(C)(C)NC(=O)c1cc(-c2ccc(C3CC3)cc2)cc(-n2nnnc2C(C)(C)C)c1]

The title compound, white foam (100 mg, 96%), MS (ISP) m/z=418.3 [(M+H)⁺], mp 115° C., was prepared in accordance with the general method of example 7 from 3-bromo-N-tert-butyl-5-(5-tert-butyltetrazol-1-yl)-benzamide (intermediate 17) (95.1 mg, 0.25 mmol) and commercially available 4-cyclopropyl-phenylboronic acid (52.6 mg, 325 μmol).

Example 108

N-tert-Butyl-3-(5-tert-butyltetrazol-1-yl)-5-(3-fluoro-4-methylphenyl)-benzamide

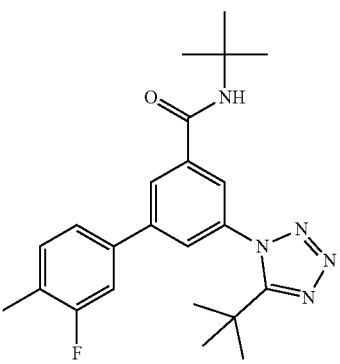 [SMILES: Cc1ccc(-c2cc(C(=O)NC(C)(C)C)cc(-n3nnnc3C(C)(C)C)c2)cc1F]

The title compound, white solid (100 mg, 98%), MS (ISP) m/z=410.3 [(M+H)⁺], mp 227.5° C., was prepared in accordance with the general method of example 7 from 3-bromo-N-tert-butyl-5-(5-tert-butyltetrazol-1-yl)-benzamide (intermediate 17) (95.1 mg, 0.25 mmol) and commercially available 3-fluoro-4-methyl-phenylboronic acid (50.0 mg, 325 μmol).

Example 109

3-(5-tert-Butyltetrazol-1-yl)-N-(2-cyclopropylpropan-2-yl)-5-(4-methylphenyl)-benzamide

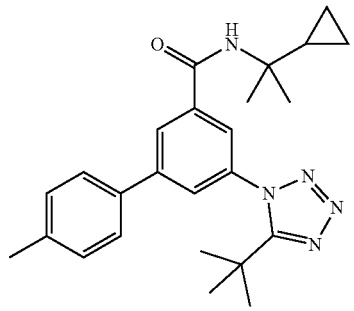 [SMILES: Cc1ccc(-c2cc(C(=O)NC(C)(C)C3CC3)cc(-n3nnnc3C(C)(C)C)c2)cc1]

The title compound, white foam (100 mg, 96%), MS (ISP) m/z=418.3 [(M+H)+], mp 91.5° C., was prepared in accordance with the general method of example 7 from 3-bromo-5-(5-tert-butyltetrazol-1-yl)-N-(2-cyclopropylpropan-2-yl)-benzamide (intermediate 18) (102 mg, 0.25 mmol) and commercially available 4-methylphenylboronic acid (44.2 mg, 325 µmol).

Example 110

3-(5-tert-Butyltetrazol-1-yl)-N-(2-cyclopropylpropan-2-yl)-5-(4-fluoro-3-methylphenyl)-benzamide

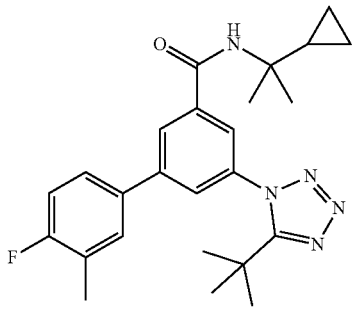 [SMILES: Cc1cc(-c2cc(C(=O)NC(C)(C)C3CC3)cc(-n3nnnc3C(C)(C)C)c2)ccc1F]

The title compound, white foam (100 mg, 92%), MS (ISP) m/z=436.3 [(M+H)+], mp 88° C., was prepared in accordance with the general method of example 7 from 3-bromo-5-(5-tert-butyltetrazol-1-yl)-N-(2-cyclopropylpropan-2-yl)-benzamide (intermediate 18) (102 mg, 0.25 mmol) and commercially available 4-fluoro-3-methyl-phenylboronic acid (50.0 mg, 325 µmol).

Example 111

3-(5-tert-Butyltetrazol-1-yl)-N-(2-cyclopropylpropan-2-yl)-5-[4-(trifluoromethyl)-phenyl]-benzamide

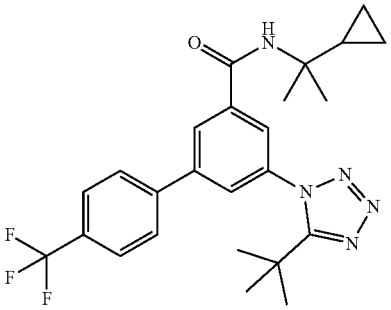 [SMILES: CC(C)(C)c1nnnn1-c1cc(C(=O)NC(C)(C)C2CC2)cc(-c2ccc(C(F)(F)F)cc2)c1]

The title compound, white foam (110 mg, 93%), MS (ISP) m/z=472.3 [(M+H)+], mp 95.5° C., was prepared in accordance with the general method of example 7 from 3-bromo-5-(5-tert-butyltetrazol-1-yl)-N-(2-cyclopropylpropan-2-yl)-benzamide (intermediate 18) (102 mg, 0.25 mmol) and commercially available 4-trifluoromethyl-phenylboronic acid (61.7 mg, 325 µmol).

Example 112

3-(5-tert-Butyltetrazol-1-yl)-5-(4-chloro-3-fluorophenyl)-N-(2-cyclopropylpropan-2-yl)-benzamide

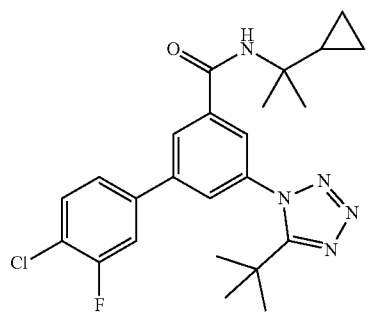 [SMILES: CC(C)(C)c1nnnn1-c1cc(C(=O)NC(C)(C)C2CC2)cc(-c2ccc(Cl)c(F)c2)c1]

The title compound, white foam (90 mg, 79%), MS (ISP) m/z=456.2 [(M+H)+], mp 106.5° C., was prepared in accordance with the general method of example 7 from 3-bromo-5-(5-tert-butyltetrazol-1-yl)-N-(2-cyclopropylpropan-2-yl)-benzamide (intermediate 18) (102 mg, 0.25 mmol) and commercially available 4-chloro-3-fluoro-phenylboronic acid (56.7 mg, 325 µmol).

Example 113

3-(5-tert-Butyltetrazol-1-yl)-N-(2-cyclopropylpropan-2-yl)-5-(3,4-difluorophenyl)-benzamide

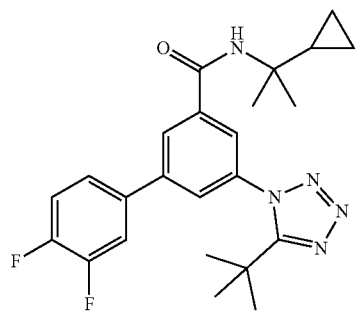

The title compound, white foam (110 mg, 100%), MS (ISP) m/z=440.3 [(M+H)+], mp 90° C., was prepared in accordance with the general method of example 7 from 3-bromo-5-(5-tert-butyltetrazol-1-yl)-N-(2-cyclopropylpropan-2-yl)-benzamide (intermediate 18) (102 mg, 0.25 mmol) and commercially available 3,4-difluoro-phenylboronic acid (51.3 mg, 325 µmol).

Example 114

3-(5-tert-Butyltetrazol-1-yl)-5-(4-cyclopropylphenyl)-N-(2-cyclopropylpropan-2-yl)-benzamide

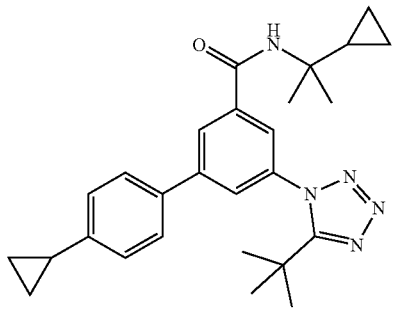 [SMILES: CC(C)(C)c1nnnn1-c1cc(C(=O)NC(C)(C)C2CC2)cc(-c2ccc(C3CC3)cc2)c1]

The title compound, white foam (110 mg, 99%), MS (ISP) m/z=444.3 [(M+H)$^+$], mp 95° C., was prepared in accordance with the general method of example 7 from 3-bromo-5-(5-tert-butyltetrazol-1-yl)-N-(2-cyclopropylpropan-2-yl)-benzamide (intermediate 18) (102 mg, 0.25 mmol) and commercially available 4-cyclopropyl-phenylboronic acid (52.6 mg, 325 μmol).

Example 115

3-(5-tert-Butyltetrazol-1-yl)-N-(2-cyclopropylpropan-2-yl)-5-(3-fluoro-4-methylphenyl)-benzamide

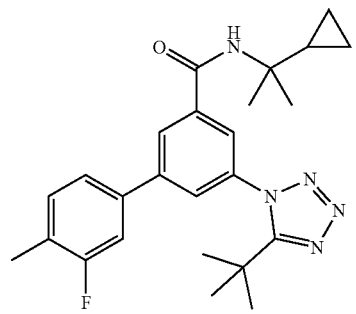 [SMILES: Cc1ccc(-c2cc(C(=O)NC(C)(C)C3CC3)cc(-n3nnnc3C(C)(C)C)c2)cc1F]

The title compound, white foam (100 mg, 92%), MS (ISP) m/z=436.3 [(M+H)$^+$], mp 92° C., was prepared in accordance with the general method of example 7 from 3-bromo-5-(5-tert-butyltetrazol-1-yl)-N-(2-cyclopropylpropan-2-yl)-benzamide (intermediate 18) (102 mg, 0.25 mmol) and commercially available 3-fluoro-4-methyl-phenylboronic acid (50.0 mg, 325 μmol).

Example 116

3-(5-tert-Butyltetrazol-1-yl)-5-[4-(trifluoromethyl)-phenyl]-N-(1,1,1-trifluoro-2-methylpropan-2-yl)-benzamide

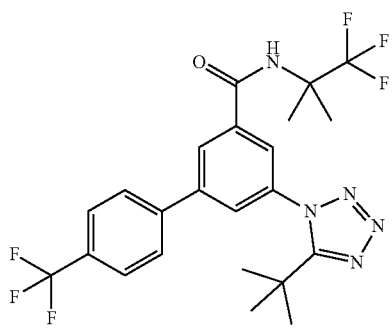 [SMILES: CC(C)(C)c1nnnn1-c1cc(C(=O)NC(C)(C)C(F)(F)F)cc(-c2ccc(C(F)(F)F)cc2)c1]

The title compound, white foam (120 mg, 96%), MS (ISP) m/z=500.2 [(M+H)$^+$], mp 108° C., was prepared in accordance with the general method of example 7 from 3-bromo-5-(5-tert-butyltetrazol-1-yl)-N-(1,1,1-trifluoro-2-methylpropan-2-yl)-benzamide (intermediate 19) (109 mg, 0.25 mmol) and commercially available 4-trifluoromethyl-phenylboronic acid (61.7 mg, 325 μmol).

Example 117

3-(5-tert-Butyltetrazol-1-yl)-5-(4-methylphenyl)-N-(1,1,1-trifluoro-2-methylpropan-2-yl)-benzamide

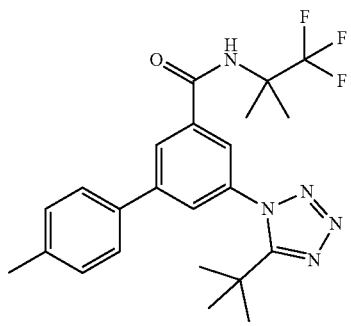 [SMILES: Cc1ccc(-c2cc(C(=O)NC(C)(C)C(F)(F)F)cc(-n3nnnc3C(C)(C)C)c2)cc1]

The title compound, white solid (100 mg, 90%), MS (ISP) m/z=446.2 [(M+H)$^+$], mp 223.5° C., was prepared in accordance with the general method of example 7 from 3-bromo-5-(5-tert-butyltetrazol-1-yl)-N-(1,1,1-trifluoro-2-methylpropan-2-yl)-benzamide (intermediate 19) (109 mg, 0.25 mmol) and commercially available 4-methylphenylboronic acid (44.2 mg, 325 μmol).

Example 118

3-(5-tert-Butyltetrazol-1-yl)-5-(4-fluoro-3-methylphenyl)-N-(1,1,1-trifluoro-2-methylpropan-2-yl)-benzamide

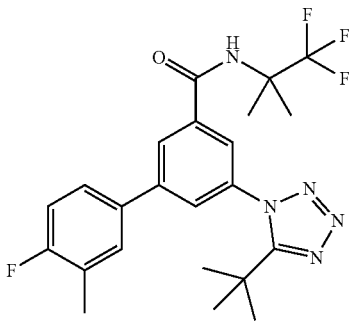

The title compound, white solid (110 mg, 95%), MS (ISP) m/z=464.2 [(M+H)$^+$], mp 203° C., was prepared in accordance with the general method of example 7 from 3-bromo-5-(5-tert-butyltetrazol-1-yl)-N-(1,1,1-trifluoro-2-methylpropan-2-yl)-benzamide (intermediate 19) (109 mg, 0.25 mmol) and commercially available 4-fluoro-3-methyl-phenylboronic acid (50.0 mg, 325 μmol).

Example 119

3-(5-tert-Butyltetrazol-1-yl)-5-(4-chloro-3-fluoro-phenyl)-N-(1,1,1-trifluoro-2-methylpropan-2-yl)-benzamide

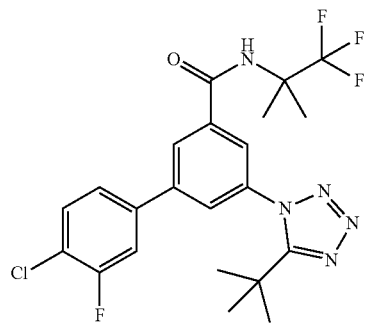 [SMILES: CC(C)(C)c1nnnn1-c1cc(C(=O)NC(C)(C)C(F)(F)F)cc(-c2ccc(Cl)c(F)c2)c1]

The title compound, white solid (90 mg, 74%), MS (ISP) m/z=484.2 [(M+H)⁺], mp 222° C., was prepared in accordance with the general method of example 7 from 3-bromo-5-(5-tert-butyltetrazol-1-yl)-N-(1,1,1-trifluoro-2-methylpropan-2-yl)-benzamide (intermediate 19) (109 mg, 0.25 mmol) and commercially available 4-chloro-3-fluoro-phenylboronic acid (56.7 mg, 325 μmol).

Example 120

3-(5-tert-Butyltetrazol-1-yl)-N-(2-cyanopropan-2-yl)-5-[4-(trifluoromethyl)-phenyl]benzamide

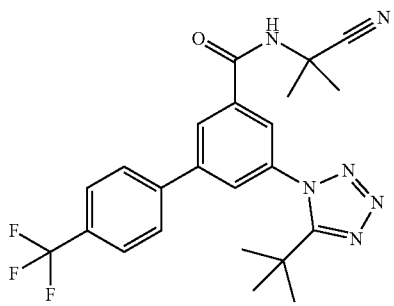 [SMILES: CC(C)(C#N)NC(=O)c1cc(-c2ccc(C(F)(F)F)cc2)cc(-n2nnnc2C(C)(C)C)c1]

The title compound, white solid (68 mg, 60%), MS (ISP) m/z=457.2 [(M+H)⁺], mp 276.5° C., was prepared in accordance with the general method of example 7 from 3-bromo-5-(5-tert-butyltetrazol-1-yl)-N-(2-cyanopropan-2-yl)-benzamide (intermediate 20) (97.8 mg, 0.25 mmol) and commercially available 4-trifluoromethyl-phenylboronic acid (61.7 mg, 325 μmol).

Example 121

3-(5-tert-Butyltetrazol-1-yl)-5-(4-chloro-3-fluoro-phenyl)-N-(2-cyanopropan-2-yl)-benzamide

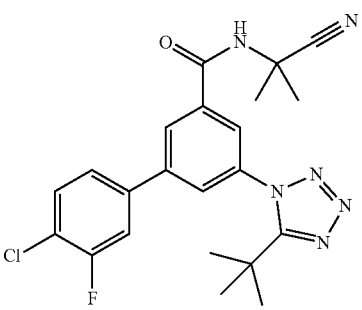 [SMILES: CC(C)(C#N)NC(=O)c1cc(-c2ccc(Cl)c(F)c2)cc(-n2nnnc2C(C)(C)C)c1]

The title compound, white solid (60 mg, 54%), MS (ISP) m/z=441.2 [(M+H)⁺], mp 261.5° C., was prepared in accordance with the general method of example 7 from 3-bromo-5-(5-tert-butyltetrazol-1-yl)-N-(2-cyanopropan-2-yl)-benzamide (intermediate 20) (97.8 mg, 0.25 mmol) and commercially available 4-chloro-3-fluoro-phenylboronic acid (56.7 mg, 325 μmol).

Example 122

3-(5-tert-Butyltetrazol-1-yl)-5-(3,4-difluorophenyl)-N-(1,1,1-trifluoro-2-methylpropan-2-yl)-benzamide

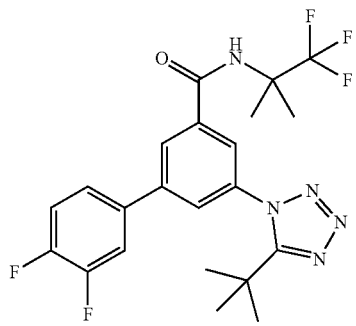

The title compound, white solid (110 mg, 94%), MS (ISP) m/z=468.2 [(M+H)⁺], mp 221.5° C., was prepared in accordance with the general method of example 7 from 3-bromo-5-(5-tert-butyltetrazol-1-yl)-N-(1,1,1-trifluoro-2-methylpropan-2-yl)-benzamide (intermediate 19) (109 mg, 0.25 mmol) and commercially available 3,4-difluoro-phenylboronic acid (51.3 mg, 325 μmol).

Example 123

3-(5-tert-Butyltetrazol-1-yl)-N-(2-cyanopropan-2-yl)-5-(3,4-difluorophenyl)-benzamide

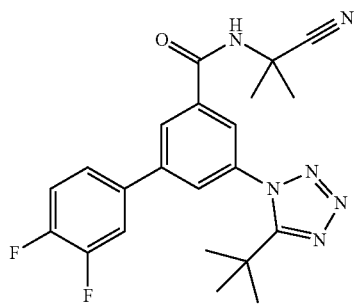

The title compound, white solid (77 mg, 73%), MS (ISP) m/z=425.2 [(M+H)$^+$], mp 263.5° C., was prepared in accordance with the general method of example 7 from 3-bromo-5-(5-tert-butyltetrazol-1-yl)-N-(2-cyanopropan-2-yl)-benzamide (intermediate 20) (97.8 mg, 0.25 mmol) and commercially available 3,4-difluoro-phenylboronic acid (51.3 mg, 325 μmol).

The invention claimed is:

1. A compound according to formula IA-7:

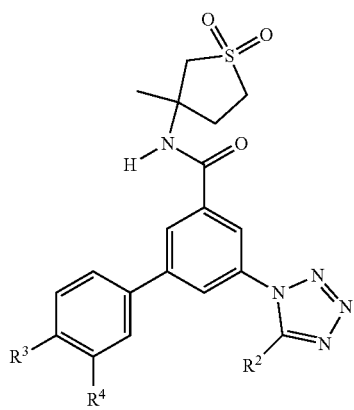

IA-7 or a pharmaceutically acceptable salt thereof, wherein

R$^2$ is hydrogen, methyl, ethyl, isopropyl, tertbutyl, cyclopropyl or CF$_3$;

R$^3$ is Cl, F, CF$_3$, methyl, methoxy, isopropyl or cyclopropyl; and

R$^4$ is hydrogen, methyl, F or Cl.

2. A compound of claim 1, or a pharmaceutically acceptable salt thereof, selected from the group consisting of:
(RS)-3-(4-Fluorophenyl)-N-(3-methyl-1,1-dioxothiolan-3-yl)-5-(tetrazol-1-yl)-benzamide;
(RS)-3-(4-Chlorophenyl)-N-(3-methyl-1,1-dioxothiolan-3-yl)-5-(tetrazol-1-yl)-benzamide (RS)—N-(3-methyl-1,1-dioxothiolan-3-yl)-3-(4-methylphenyl)-5-(5-propan-2-yltetrazol-1-yl)-benzamide;
(RS)—N-(3-Methyl-1,1-dioxothiolan-3-yl)-3-(4-methylphenyl)-5-(5-methyltetrazol-1-yl)-benzamide;
(RS)-3-(5-Cyclopropyltetrazol-1-yl)-N-(3-methyl-1,1-dioxothiolan-3-yl)-5-(4-methylphenyl)-benzamide;
(RS)-3-(5-Ethyltetrazol-1-yl)-N-(3-methyl-1,1-dioxothiolan-3-yl)-5-(4-methylphenyl)-benzamide;
(RS)-3-(4-Chlorophenyl)-N-(3-methyl-1,1-dioxothiolan-3-yl)-5-(5-propan-2-yltetrazol-1-yl)benzamide;
(RS)—N-(3-methyl-1,1-dioxothiolan-3-yl)-3-(5-propan-2-yltetrazol-1-yl)-5 44-(trifluoromethyl)phenyl]benzamide;
(RS)-3-(4-Chlorophenyl)-5-(5-cyclopropyltetrazol-1-yl)-N-(3-methyl-1,1-dioxothiolan-3-yl)-benzamide;
(RS)-3-(4-Fluorophenyl)-N-(3-methyl-1,1-dioxothiolan-3-yl)-5-(5-propan-2-yltetrazol-1-yl)-benzamide;
(RS)-3-(4-Chlorophenyl)-N-(3-methyl-1,1-dioxothiolan-3-yl)-5-(5-methyltetrazol-1-yl)-benzamide;
(RS)-3-(5-Cyclopropyltetrazol-1-yl)-5-(4-fluorophenyl)-N-(3-methyl-1,1-dioxothiolan-3-yl)-benzamide;
(RS)-3-(4-Fluorophenyl)-N-(3-methyl-1,1-dioxothiolan-3-yl)-5-(5-methyltetrazol-1-yl)-benzamide;
(RS)-3-(5-tert-Butyltetrazol-1-yl)-5-(4-chlorophenyl)-N-(3-methyl-1,1-dioxothiolan-3-yl)benzamide; and
(RS)-3-(5-tert-Butyltetrazol-1-yl)-5-(4-fluorophenyl)-N-(3-methyl-1,1-dioxothiolan-3-yl)-benzamide
of formula I according to claim 1, wherein R$^{1'}$ and R$^1$ may form together a 1,1-dioxo-tetrahydrothiophen-3-yl ring.

3. A pharmaceutical composition comprising a compound of formula I as claimed in claim 1, or a pharmaceutically acceptable salt thereof, and one or more pharmaceutically acceptable excipients.

4. A method for the treatment of schizophrenia, bipolar disorder, obsessive-compulsive disorder or autism spectrum disorder which method comprises administering an effective amount of a compound of formula I as claimed in claim 1, or a pharmaceutically acceptable salt thereof.

* * * * *

UNITED STATES PATENT AND TRADEMARK OFFICE
CERTIFICATE OF CORRECTION

PATENT NO. : 10,577,332 B2
APPLICATION NO. : 15/569349
DATED : March 3, 2020
INVENTOR(S) : Marius Hoener et al.

Page 1 of 1

It is certified that error appears in the above-identified patent and that said Letters Patent is hereby corrected as shown below:

In the Claims

Column 140, Lines 21-23, please delete:
"(RS)-N-(3-methyl-1,1-dioxothiolan-3-yl)-3-(5-propan-2-yltetrazol-1-yl)-5 44-(trifluoromethyl)phenyl]benzamide;"
And insert:
--(RS)-N-(3-methyl-1,1-dioxothiolan-3-yl)-3-(5-propan-2-yltetrazol-1-yl)-5-[4-(trifluoromethyl)phenyl]benzamide;--

Column 140, Line 38, please delete:
"(3-methyl-1,1-dioxothiolan-3-yl)-benzamide"
And insert:
--(3-methyl-1,1-dioxothiolan-3-yl)-benzamide.--

Column 140, Lines 39-41, please delete:
"of formula I according to claim 1, wherein R1' and R1 may form together a 1,1-dioxo-tetrahydro-thiophen-3-yl ring."

Signed and Sealed this
Twentieth Day of October, 2020

Andrei Iancu
*Director of the United States Patent and Trademark Office*